US007285382B2

(12) United States Patent
de Sauvage et al.

(10) Patent No.: US 7,285,382 B2
(45) Date of Patent: Oct. 23, 2007

(54) COMPOSITIONS AND METHODS FOR TREATMENT OF CANCER

(75) Inventors: Frederic de Sauvage, Foster City, CA (US); Audrey Goddard, San Francisco, CA (US); Austin L. Gurney, Belmont, CA (US); Jo-Anne S. Hongo, Redwood City, CA (US); Victoria Smith, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 581 days.

(21) Appl. No.: 10/182,033

(22) PCT Filed: Jan. 25, 2001

(86) PCT No.: PCT/US01/02622

§ 371 (c)(1),
(2), (4) Date: Oct. 24, 2002

(87) PCT Pub. No.: WO03/013808

PCT Pub. Date: Feb. 20, 2003

(65) Prior Publication Data

US 2003/0215457 A1    Nov. 20, 2003

Related U.S. Application Data

(60) Provisional application No. 60/195,761, filed on Apr. 10, 2000, provisional application No. 60/177,951, filed on Jan. 25, 2000.

(51) Int. Cl.
*C12Q 1/70* (2006.01)
(52) U.S. Cl. ........................................ 435/5
(58) Field of Classification Search .................. None
See application file for complete search history.

(56) References Cited

U.S. PATENT DOCUMENTS

| 5,677,171 | A | 10/1997 | Hudziak et al. |
| 5,693,465 | A | 12/1997 | Manning et al. |
| 5,720,937 | A | 2/1998 | Hudziak et al. |
| 5,720,954 | A | 2/1998 | Hudziak et al. |
| 5,725,856 | A | 3/1998 | Hudziak et al. |
| 5,770,195 | A | 6/1998 | Hudziak et al. |
| 5,772,997 | A | 6/1998 | Hudziak et al. |
| 6,649,342 | B1 | 11/2003 | Mack et al. |
| 6,750,013 | B2 | 6/2004 | Gish et al. |
| 6,762,020 | B1 * | 7/2004 | Mack et al. ............... 435/6 |
| 6,780,586 | B1 | 8/2004 | Mack et al. |
| 2002/0006616 | A1 | 1/2002 | Gish et al. |
| 2004/0141983 | A1 | 7/2004 | Law et al. |

FOREIGN PATENT DOCUMENTS

| CA | 2132500 | 3/1996 |
| DE | 19813839 | 9/1999 |
| EP | 474727 | 7/1997 |
| EP | 1033401 | 9/2000 |
| WO | PCT/US 89/00051 | 1/1989 |
| WO | WO 89/06692 | 7/1989 |
| WO | PCT/US 90/02697 | 5/1990 |
| WO | WO 90/14357 | 11/1990 |
| WO | WO 96/27011 | 9/1996 |
| WO | PCT/US 97/18385 | 10/1997 |
| WO | WO 98/17797 | 4/1998 |
| WO | WO 98/50555 | 11/1998 |
| WO | PCT/US 98/26266 | 12/1998 |
| WO | PCT/US 99/06673 | 3/1999 |
| WO | WO 99/31140 | 6/1999 |
| WO | WO 99/48527 | 9/1999 |
| WO | WO 2000/22130 | 4/2000 |
| WO | 00/55629 | 9/2000 |
| WO | WO 2000/55174 | 9/2000 |
| WO | WO 2000/58336 | 10/2000 |
| WO | WO 2000/60076 | 10/2000 |
| WO | WO 2001/18022 | 3/2001 |
| WO | WO02/16939 | * 2/2002 |
| WO | WO02/059377 | * 8/2002 |
| WO | 2004/067564 | 8/2004 |

OTHER PUBLICATIONS

Altschul and Gish, "Local Alignment Statistics" *Methods in Enzymology* 266:460-480 (1996).
Altschul et al., "Gapped Blast and PSI-Blast: A New Generation of Protein Database Search Programs" *Nucleic Acids Research*. 25(17):3389-3402 (1997).
Blattner, F.R. et al., "The Complete Genome Sequence of *Escherichia coli* K-12" *EMBL Database* (Acc. No. AE000299; XP-002175108) (Jan. 29, 1997).
Carter et al., "Humanization of an Anti-p185$^{HER2}$ Antibody For Human Cancer Therapy" *Proc. Natl. Acad. Sci. USA* 89:4285-4289 (May 1992).
Dehesh, K., "Cuphea Hookeriana Thioesterase FatB1-1 mRNA, complete cds" *EMBL Database* (Acc. No. AFO62400; XP-002175109) (Nov. 12, 1998).
El-Tanani, M.K.K. and C.D. Green, "Interaction Between Estradiol and cAMP in the Regulation of Specific Gene Expression" *Mol. & Cellular Endocrinology* 124(1-2):71-77 (1996).
El-Tanani, Mohammed K.K. and C.D. Green, "Interaction Between Estradiol and Growth Factors in the Regulation of Specific Gene Expression in MCF-7 Human Breast Cancer Cells," *Journal of Steroid Biochem. and Mol. Bio.* 60(5-6):269-276 (1997).
Fendly, B.M. et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

(Continued)

*Primary Examiner*—Christopher H. Yaen
(74) *Attorney, Agent, or Firm*—Dierdre L. Conley; Ginger R. Dreger; Heller Ehrman LLP

(57) ABSTRACT

The present invention concerns compositions and methods for the treatment of disorders characterized by the overexpression of an LIV-1. More specifically, the compositions include DNA and amino acid sequences of an LIV-1, antibodies to an LIV-1, and methods for the treatment of a mammal susceptible to or diagnosed with cancer wherein an LIV-1 is overexpressed.

3 Claims, 26 Drawing Sheets

OTHER PUBLICATIONS

Freund, Y.R. and Blair, P.B., "Depression of Natural Killer Activity and Mitogen Responsiveness in Mice Treated with Pristane" *J. Immunol.* 129:2826-2830 (1982).

Green, C. et al., "*Homo sapiens* Estrogen Regulated LIV-1 Protein (LIV-1) mRNA, complete cds" *NCBI Database* (Acc. No. U41060, Version 2; GI: 12711792) (XP002175107 Feb. 8, 2001).

Green, C. et al., "Human Breast Cancer, Estrogen Regulated LIV-1 Protein (LIV-1) mRNA, partial cds" *NCBI Database* (Acc. No. U41060, version 1; GI: 1256000) (XP002175106 Apr. 6, 1996).

Hattori, M. et al., "*Homo sapiens* genomic DNA, chromosome 18q12 clone: RP11-701C9, Working Draft Sequence, 15 unordered pieces" *EMBL Database* (Acc. No. AP001158) (Feb. 15, 2000).

Hongo, J.S. et al., "Development and Characterization of Murine Monoclonal Antibodies to the Latency-Associated Peptide of Transforming Growth Factor β1" *Hybridoma* 14:253-260 (1995).

Jones et al., "Replacing the Complentarity-Determining Regions in a Human Antibody with Those From a Mouse." *Nature.* 321:522-525 (May 29, 1986).

Knowlden, J.M. et al., "Use of Reverse Transcription-Polymerase Chain Reaction Methodology to Detect Estrogen-regulated Gene Expression in Small Breast Cancer Specimens" *Clin. Cancer Res.* 3(11):2165-2172 (1997).

Kohler and Milstein., "Continuous Cultures of Fused Cells Secreting Antibody of Predefined Specificity." *Nature.* 256:495-497 (Aug. 7, 1975).

Kononen, J. et al., "Tissue microarrays for high-throughput molecular profiling of tumor specimens" *Nature Medicine* 4:844-847 (1998).

Lu and Gillett., "An Optimized Protocol for In Situ Hybridization Using PCR-Generated 33P-Labeled Riboprobes." *Cell Vision.* 1(2):169-176 (1994).

Manning, D.L. et al., "Differential Expression of Oestrogen Regulated Genes in Breast Cancer" *Acta Oncologica* 34(5):641-646 (1995).

Manning, D.L. et al., "Oestrogen-regulated Genes in Breast Cancer: Association of pLIV1 With Lymph Node Involvement" *European J. Cancer* 30A(5): 675-678 (1994).

Manning, D.L. et al., "The Role of Four Oestrogen-responsive Genes, pLIV1, pS2, pSYD3 and pSYD8, in Predicting Reponsiveness to Endocrine Therapy in Primary Breast Cancer" *European J. Cancer* 29A(10):1462-1468 (1993).

McClelland, R.A. et al., "Effects of short-tern antiestrogen treatment of primary breast cancer on estrogen receptor mRNA and protein expression and on extrogen-regulated genes" *Breast Cancer Res. and Treatment* 41(1):31-41 (1996).

McClelland, R.A. et al., "Oestrogen-regulated genes in breast cancer: associated of pLIV1 with response to endocrine therapy" *British J. Cancer* 77(10):1653-1656 (1998).

Nakamura, G.R. et al., "Strain specificity and binding affinity requirements of neutralizing monoclonal antibodies to the C4 domain of gp120 from human immunodeficiency virus type 1" *Journal of Virology* 67(10):6179-6191 (Oct. 1993).

Renz, M.E. et al., "Structural requirements for adhesion of soluble recombinant murine vascular cell adhesion molecule-1 to α4β1" *Journal of Cell Biology* 125(6):1395-1406 (Jun. 1994).

Riechmann et al., "Reshaping Human Antibodies for Therapy" *Nature* 332:323-327 (Mar. 24, 1988).

Taylor, K.M. et al., "LIV-1 Breast Cancer Protein Belongs to a New Family of Histidine-rich Transmembrane Proteins with Potential to Control Intracellular Zn++" *Clinical & Experimental Metastasis* (XP-001013451) 17(9):758 (1999).

Taylor, K.M. et al., "The LIV-1 Gene, Implicated in Metastatic Breast Cancer, Codes for a Histidine-rich Transmembrane Protein" *British Journal of Cancer* (XP001013344) 80(Supp. 2) :pp. 24 (Jul. 1999).

Taylor, K.M., "LIV-1 Breast Cancer Protein Belongs to New Family of Histidine-rich Membrane Proteins with Potential to Control Intracellular Zn++ Homeostas" *IUBMB Life* 49(4):249-253 (Apr. 2000).

Verhoeyen et al. "Reshaping Human Antibodies: Grafting an Antilysozyme Activity" *Science* 239:1534-1536 (Mar. 25, 1988).

* cited by examiner

```
CTCGTGCCGA ATTCGGCACG AGACCGCGTG TTCGCGCCTG GTAGAGATTT   50
CTCGAAGACA CCAGTGGGCC CGTGTGGAAC CAAACCTGCG CGCGTGGCCG  100
GGCCGTGGGA CAACGAGGCC GCGGAGACGA AGGCGCAATG GCGAGGAAGT  150
TATCTGTAAT CTTGATCCTG ACCTTTGCCC TCTCTGTCAC AAATCCCCTT  200
CATGAACTAA AAGCAGCTGC TTTCCCCCAG ACCACTGAGA AAATTAGTCC  250
GAATTGGGAA TCTGGCATTA ATGTTGACTT GGCAATTTCC ACACGGCAAT  300
ATCATCTACA ACAGCTTTTC TACCGCTATG GAGAAAATAA TTCTTTGTCA  350
GTTGAAGGGT TCAGAAAATT ACTTCAAAAT ATAGGCATAG ATAAGATTAA  400
AAGAATCCAT ATACACCATG ACCACGACCA TCACTCAGAC CACGAGCATC  450
ACTCAGACCA TGAGCGTCAC TCAGACCATG AGCATCACTC AGACCACGAG  500
CATCACTCTG ACCATAATCA TGCTGCTTCT GGTAAAAATA AGCGAAAAGC  550
TCTTTGCCCA GACCATGACT CAGATAGTTC AGGTAAAGAT CCTAGAAACA  600
GCCAGGGGAA AGGAGCTCAC CGACCAGAAC ATGCCAGTGG TAGAAGGAAT  650
GTCAAGGACA GTGTTAGTGC TAGTGAAGTG ACCTCAACTG TGTACAACAC  700
TGTCTCTGAA GGAACTCACT TTCTAGAGAC AATAGAGACT CCAAGACCTG  750
GAAAACTCTT CCCCAAAGAT GTAAGCAGCT CCACTCCACC CAGTGTCACA  800
TCAAAGAGCC GGGTGAGCCG GCTGGCTGGT AGGAAAACAA ATGAATCTGT  850
GAGTGAGCCC CGAAAAGGCT TTATGTATTC CAGAAACACA AATGAAAATC  900
CTCAGGAGTG TTTCAATGCA TCAAAGCTAC TGACATCTCA TGGCATGGGC  950
ATCCAGGTTC CGCTGAATGC AACAGAGTTC AACTATCTCT GTCCAGCCAT 1000
CATCAACCAA ATTGATGCTA GATCTTGTCT GATTCATACA AGTGAAAAGA 1050
AGGCTGAAAT CCCTCCAAAG ACCTATTCAT TACAAATAGC CTGGGTTGGT 1100
GGTTTTATAG CCATTTCCAT CATCAGTTTC CTGTCTCTGC TGGGGGTTAT 1150
CTTAGTGCCT CTCATGAATC GGGTGTTTTT CAAATTTCTC CTGAGTTTCC 1200
TTGTGGCACT GGCCGTTGGG ACTTTGAGTG GTGATGCTTT TTTACACCTT 1250
CTTCCACATT CTCATGCAAG TCACCACCAT AGTCATAGCC ATGAAGAACC 1300
AGCAATGGAA ATGAAAAGAG GACCACTTTT CAGTCATCTG TCTTCTCAAA 1350
ACATAGAAGA AAGTGCCTAT TTTGATTCCA CGTGGAAGGG TCTAACAGCT 1400
CTAGGAGGCC TGTATTTCAT GTTTCTTGTT GAACATGTCC TCACATTGAT 1450
CAAACAATTT AAAGATAAGA AGAAAAAGAA TCAGAAGAAA CCTGAAAATG 1500
ATGATGATGT GGAGATTAAG AAGCAGTTGT CCAAGTATGA ATCTCAACTT 1550
TCAACAAATG AGGAGAAAGT AGATACAGAT GATCGAACTG AAGGCTATTT 1600
ACGAGCAGAC TCACAAGAGC CCTCCCACTT TGATTCTCAG CAGCCTGCAG 1650
TCTTGGAAGA AGAAGAGGTC ATGATAGCTC ATGCTCATCC ACAGGAAGTC 1700
TACAATGAAT ATGTACCCAG AGGGTGCAAG AATAAATGCC ATTCACATTT 1750
CCACGATACA CTCGGCCAGT CAGACGATCT CATTCACCAC CATCATGACT 1800
ACCATCATAT TCTCCATCAT CACCACCACC AAAACCACCA TCCTCACAGT 1850
CACAGCCAGC GCTACTCTCG GGAGGAGCTG AAAGATGCCG GCGTCGCCAC 1900
TTTGGCCTGG ATGGTGATAA TGGGTGATGG CCTGCACAAT TTCAGCGATG 1950
GCCTAGCAAT TGGTGCTGCT TTTACTGAAG GCTTATCAAG TGGTTTAAGT 2000
ACTTCTGTTG CTGTGTTCTG TCATGAGTTG CCTCATGAAT TAGGTGACTT 2050
TGCTGTTCTA CTAAAGGCTG GCATGACCGT TAAGCAGGCT GTCCTTTATA 2100
```

FIG._1A-1

```
ATGCATTGTC AGCCATGCTG GCGTATCTTG GAATGGCAAC AGGAATTTTC 2150
ATTGGTCATT ATGCTGAAAA TGTTTCTATG TGGATATTTG CACTTACTGC 2200
TGGCTTATTC ATGTATGTTG CTCTGGTTGA TATGGTACCT GAAATGCTGC 2250
ACAATGATGC TAGTGACCAT GGATGTAGCC GCTGGGGGTA TTTCTTTTTA 2300
CAGAATGCTG GGATGCTTTT GGGTTTTGGA ATTATGTTAC TTATTCCATA 2350
TTTGAACATA AAATCGTGTT CGTATAAATT TCTAGTTAAG GTTTAAATGC 2400
TAGAGTAGCT TAAAAAGTTG TCATAGTTTC AGTAGGTCAT AGGGAGATGA 2450
GTTTGTATGC TGTACTATGC AGCGTTTAAA GTTAGTGGGT TTTGTGATTT 2500
TTGTATTGAA TATTGCTGTC TGTTACAAAG TCAGTTAAAG GTACGTTTTA 2550
ATATTTAAGT TATTCTATCT TGGAGATAAA ATCTGTATGT GCAATTCACC 2600
GGTATTACCA GTTTATTATG TAAACAAGAG ATTTGGCATG ACATGTTCTG 2650
TATGTTTCAG GGAAAAATGT CTTTAATGCT TTTTCAAGAA CTAACACAGT 2700
TATTCCTATA CTGGATTTTA GGTCTCTGAA GAACTGCTGG TGTTTAGGAA 2750
TAAGAATGTG CATGAAGCCT AAAATACCAA GAAAGCTTAT ACTGAATTTA 2800
AGCAAAGAAA TAAAGGAGAA AAGAGAAGAA TCTGAGAATT GGGGAGGCAT 2850
AGATTCTTAT AAAAATCACA AAATTTGTTG TAAATTAGAG GGGAGAAATT 2900
TAGAATTAAG TATAAAAGG CAGAATTAGT ATAGAGTACA TTCATTAAAC 2950
ATTTTTGTCA GGATTATTTC CCGTAAAAAC GTAGTGAGCA CTCTCATATA 3000
CTAATTAGTG TACATTTAAC TTTGTATAAT ACAGAAATCT AAATATATTT 3050
AATGAATTCA AGCAATATAC ACTTGACCAA GAAATTGGAA TTTCAAAATG 3100
TTCGTGCGGG TTATATACCA GATGAGTACA GTGAGTAGTT TATGTATCAC 3150
CAGACTGGGT TATTGCCAAG TTATATATCA CCAAAAGCTG TATGACTGGA 3200
TGTTCTGGTT ACCTGGTTTA CAAAATTATC AGAGTAGTAA AACTTTGATA 3250
TATATGAGGA TATTAAAACT ACACTAAGTA TCATTTGATT CGATTCAGAA 3300
AGTACTTTGA TATCTCTCAG TGCTTCAGTG CTATCATTGT GAGCAATTGT 3350
CTTTATATAC GGTACTGTAG CCATACTAGG CCTGTCTGTG GCATTCTCTA 3400
GATGTTTCTT TTTTACACAA TAAATTCCTT ATATCAGCTT GAAAAAAAAA 3450
AAAAAAAAAA A 3461   (SEQ ID NO:1)
```

FIG._1A-2

```
Met Ala Arg Lys Leu Ser Val Ile Leu Ile Leu Thr Phe Ala Leu
 1               5                  10                  15

Ser Val Thr Asn Pro Leu His Glu Leu Lys Ala Ala Ala Phe Pro
                 20              25                      30

Gln Thr Thr Glu Lys Ile Ser Pro Asn Trp Glu Ser Gly Ile Asn
                 35              40                      45

Val Asp Leu Ala Ile Ser Thr Arg Gln Tyr His Leu Gln Gln Leu
                 50              55                      60

Phe Tyr Arg Tyr Gly Glu Asn Asn Ser Leu Ser Val Glu Gly Phe
                 65              70                      75

Arg Lys Leu Leu Gln Asn Ile Gly Ile Asp Lys Ile Lys Arg Ile
                 80              85                      90

His Ile His His Asp His Asp His His Ser Asp His Glu His His
                 95             100                     105

Ser Asp His Glu Arg His Ser Asp His Glu His His Ser Asp His
                110             115                     120

Glu His His Ser Asp His Asn His Ala Ala Ser Gly Lys Asn Lys
                125             130                     135

Arg Lys Ala Leu Cys Pro Asp His Asp Ser Asp Ser Ser Gly Lys
                140             145                     150

Asp Pro Arg Asn Ser Gln Gly Lys Gly Ala His Arg Pro Glu His
                155             160                     165

Ala Ser Gly Arg Arg Asn Val Lys Asp Ser Val Ser Ala Ser Glu
                170             175                     180

Val Thr Ser Thr Val Tyr Asn Thr Val Ser Glu Gly Thr His Phe
                185             190                     195

Leu Glu Thr Ile Glu Thr Pro Arg Pro Gly Lys Leu Phe Pro Lys
                200             205                     210

Asp Val Ser Ser Ser Thr Pro Pro Ser Val Thr Ser Lys Ser Arg
                215             220                     225

Val Ser Arg Leu Ala Gly Arg Lys Thr Asn Glu Ser Val Ser Glu
                230             235                     240

Pro Arg Lys Gly Phe Met Tyr Ser Arg Asn Thr Asn Glu Asn Pro
                245             250                     255
```

FIG._1B-1

```
Gln Glu Cys Phe Asn Ala Ser Lys Leu Leu Thr Ser His Gly Met
            260                 265                 270

Gly Ile Gln Val Pro Leu Asn Ala Thr Glu Phe Asn Tyr Leu Cys
            275                 280                 285

Pro Ala Ile Ile Asn Gln Ile Asp Ala Arg Ser Cys Leu Ile His
            290                 295                 300

Thr Ser Glu Lys Lys Ala Glu Ile Pro Pro Lys Thr Tyr Ser Leu
            305                 310                 315

Gln Ile Ala Trp Val Gly Gly Phe Ile Ala Ile Ser Ile Ile Ser
            320                 325                 330

Phe Leu Ser Leu Leu Gly Val Ile Leu Val Pro Leu Met Asn Arg
            335                 340                 345

Val Phe Phe Lys Phe Leu Leu Ser Phe Leu Val Ala Leu Ala Val
            350                 355                 360

Gly Thr Leu Ser Gly Asp Ala Phe Leu His Leu Leu Pro His Ser
            365                 370                 375

His Ala Ser His His Ser His Ser His Glu Glu Pro Ala Met
            380                 385                 390

Glu Met Lys Arg Gly Pro Leu Phe Ser His Leu Ser Ser Gln Asn
            395                 400                 405

Ile Glu Glu Ser Ala Tyr Phe Asp Ser Thr Trp Lys Gly Leu Thr
            410                 415                 420

Ala Leu Gly Gly Leu Tyr Phe Met Phe Leu Val Glu His Val Leu
            425                 430                 435

Thr Leu Ile Lys Gln Phe Lys Asp Lys Lys Lys Asn Gln Lys
            440                 445                 450

Lys Pro Glu Asn Asp Asp Val Glu Ile Lys Lys Gln Leu Ser
            455                 460                 465

Lys Tyr Glu Ser Gln Leu Ser Thr Asn Glu Glu Lys Val Asp Thr
            470                 475                 480

Asp Asp Arg Thr Glu Gly Tyr Leu Arg Ala Asp Ser Gln Glu Pro
            485                 490                 495

Ser His Phe Asp Ser Gln Gln Pro Ala Val Leu Glu Glu Glu
            500                 505                 510
```

FIG._1B-2

```
Val Met Ile Ala His Ala His Pro Gln Glu Val Tyr Asn Glu Tyr
            515             520             525

Val Pro Arg Gly Cys Lys Asn Lys Cys His Ser His Phe His Asp
            530             535             540

Thr Leu Gly Gln Ser Asp Asp Leu Ile His His His Asp Tyr
            545             550             555

His His Ile Leu His His His His Gln Asn His His Pro His
            560             565             570

Ser His Ser Gln Arg Tyr Ser Arg Glu Glu Leu Lys Asp Ala Gly
            575             580             585

Val Ala Thr Leu Ala Trp Met Val Ile Met Gly Asp Gly Leu His
            590             595             600

Asn Phe Ser Asp Gly Leu Ala Ile Gly Ala Ala Phe Thr Glu Gly
            605             610             615

Leu Ser Ser Gly Leu Ser Thr Ser Val Ala Val Phe Cys His Glu
            620             625             630

Leu Pro His Glu Leu Gly Asp Phe Ala Val Leu Leu Lys Ala Gly
            635             640             645

Met Thr Val Lys Gln Ala Val Leu Tyr Asn Ala Leu Ser Ala Met
            650             655             660

Leu Ala Tyr Leu Gly Met Ala Thr Gly Ile Phe Ile Gly His Tyr
            665             670             675

Ala Glu Asn Val Ser Met Trp Ile Phe Ala Leu Thr Ala Gly Leu
            680             685             690

Phe Met Tyr Val Ala Leu Val Asp Met Val Pro Glu Met Leu His
            695             700             705

Asn Asp Ala Ser Asp His Gly Cys Ser Arg Trp Gly Tyr Phe Phe
            710             715             720

Leu Gln Asn Ala Gly Met Leu Leu Gly Phe Gly Ile Met Leu Leu
            725             730             735

Ile Pro Tyr Leu Asn Ile Lys Ser Cys Ser Tyr Lys Phe Leu Val
            740             745             750

Lys Val   (SEQ ID NO:2)
```

FIG._1B-3

```
TTTTTTTTTG  ATATAAGGAA  TTTATTGTGT  AAAAAAGAAA  CATCTAGAGA   50

ATGCCACAGA  CAGGCCTAGT  ATGGCTACAG  TACCGTATAT  AAAAGACAAT  100

TGCTCACAAT  GATAGCACTG  AAGCACTGAG  AGATATCAAA  GTACTTTCTG  150

AATCGAATCA  AATGATACTT  AGTGTAGTTT  TAATATCCTC  ATATATATCA  200

AAGTTTTACT  ACTCTGATAA  TTTTGTAAAC  CAGGGTAACC  AGGANCATCC  250

AGTCATACAG  CTTTTGGGTG  ATATATAACT  TGGGCAATAA  CCCAGTCTGG  300

GTGATACNTA  AANCTACTCA  CTGTACTCAT  CTGGGTATAT  ACCCGCACGG  350

ANCATTTTGG  AAATTCCCAA  TTTCTTGGGT  CAGGTGATAT  A           391
```

(SEQ ID NO:5)

```
ss.DNA164647          1 CCGGCCCGTGTGGAACCAAACCTGCGCGCCTGGCCGTGGGCCGTGGGACAACGAGGCC
ss.DNA164647         60 GCGGAGACGAAGGCGCAATGGCGAGGAAGTTATCTGTAATCTTGATCCTTGACCTTTGCCC
ss.DNA164647        120 TCTCTGTCACACAAATCCCCCTTCATGAACTAAAAGCAGCTGCTTTCCCCCAGAGACCACTGAGA
ss.DNA164647        180 AAATTAGTCCGAATTGGGAATCTGGCATTAATGTTGACTTGGCAATTTCCACACGGCAAT
ss.DNA164647        240 ATCATCTACAACAGCTTTTCTACCGCTATGGAGAAAATAAGATTAAAAGAATCCATATACACCATG
ss.DNA164647        300 TCAGAAAATTACTTCAAAAATATATAGGCATAGATAAGGCGTCACTCAGACCATG
ss.DNA164647        360 ACCACGACCATCACTCAGACCACGAGCATCACTCTGACCATGATCATCACTCCACCATAATCATG
ss.DNA164647        420 AGCATCACTCAGACCACCAGAGCATCACTCTGACCATGATCATCACTCCACCATAATCATG
ss.DNA164647        480 CTGCTTCTGGTAAAATAAGCGAAAAGCTCTTTGCCCAGACCATGACTCAGATAGTTCAG
ss.DNA164647        540 GTAAAGATCCTAGAAACAGCCAGGGGAAAGGAGCTCACCGACCAGAACATGCCAGTGGTA
ss.DNA164647        600 GAAGGAATGTCAAGGACAGTGTTAGTGCTAGTGCTAAGTGACCTCAACTGTGTACAACACTG
ss.DNA164647        660 TCTCTGAAGGAACTCACTTTCTAGAGACAATAGAGACTCCAAGACCTGGAAAACTCTTCC
ss.DNA164647        720 CCAAAGATGTAAGCAGCTCCACTCCACCCAGTGTCACATCAAAGAGCCGGGTGAGCCGGC
```

```
ss.DNA164647      780         790         800         810         820         830
             TGGCTGGTAGGAAAACAAATGAATCTGTGAGTGAGCCCCGAAAAAGGCTTTATGTATTCCA ss.DNA164647      840         850         860         870         880         890
             GAAACACAAATGAAAATCCTCAGGAGTGTTTCAATGCATCAAAGCTACTGACATCTCATG ss.DNA164647      900         910         920         930         940         950
             GCATGGGCATCCAGGTTCCGCTGAATGCAACAGAGTTCAACTATCTCTGTCCAGCCATCA ss.DNA164647      960         970         980         990        1000        1010
             TCAACCAAATGATGCTAGATCTTGTCTGATTCATACAAGTGAAAAGAAGGCTGAAATCC ss.DNA164647     1020        1030        1040        1050        1060        1070
             CTCCAAAGACCTATTCATTACAAATAGCCTGGGTTGGTGGTTTTATAGCCATTTCCATCA ss.DNA164647     1080        1090        1100        1110        1120        1130
             TCAGTTTCCTGTCTCTGCTGGGGTTATCTTAGTGCCCTCTCATGAATCGGGTGTTTTTCA ss.DNA164647     1140        1150        1160        1170        1180        1190
             AATTTCTCCTGAGTTCCTTGTGGCACTGGCCGTTGGGACTTTGAGTGGTGATGCTTTTT ss.DNA164647     1200        1210        1220        1230        1240        1250
             TACACCTTCTTCCACATTCTCATGCAAGTCACCACCATAGTCATAGCCATGAAGAACCAG ss.DNA164647     1260        1270        1280        1290        1300        1310
             CAATGGAAATGAAAAGAGGACCACTTTTCAGTCATCTGTCTTCTCAAAACATAGAAGAAA ss.DNA164647     1320        1330        1340        1350        1360        1370
             GTGCCCTATTTGATTCCACGTGGAAGGGTCTAACAGCTCTAGGAGGCCTGTATTTCATGT ss.DNA164647     1380        1390        1400        1410        1420        1430
             TTCTTGTTGAACATGTCCTCACATTGATCAAACAATTAAAGATAAGAAGAAAAAGAATC ss.DNA164647     1440        1450        1460        1470        1480        1490
             AGAAGAAACCTGAAAATGATGATGTGGAGATTAAGAAGCAGTTGTCCAAGTATGAAT ss.DNA164647     1500        1510        1520        1530        1540        1550
             CTCAACTTTCAACAAATGAGGAGAAAGTAGATACAGATGATCGAACTGAAGGCTATTTAC
```

FIG. 2A-2

```
ss.DNA164647  1560       1570       1580       1590       1600       1610
              GAGCAGAGACTTCACAAGAGCCCTCCCACTTTGATTCTTCAGCAGCCTGCAGTCTTGGAAGAAG ss.DNA164647  1620       1630       1640       1650       1660       1670
              AAGAGGTCATGATAGCTCATGCTCATCCACAGGAAGTCTACAATGAATATGTACCCAGAG ss.DNA164647  1680       1690       1700       1710       1720       1730
              GGTGCAAGAATAAATGCCATTCACATTTCCACGATACACTCGGCCAGTCAGACGATCTCA ss.DNA164647  1740       1750       1760       1770       1780       1790
              TTCACCACCATCATGACTACCATCATATTCTCCATCATCACCACCAAAACCACCATC ss.DNA164647  1800       1810       1820       1830       1840       1850
              CTCACAGTCACAGCCAGCGCTACTCTCGGGAGGAGCTGAAAGATGCCGGGCGTCGCCACTT ss.DNA164647  1860       1870       1880       1890       1900       1910
              TGGCCTGGATGGTGATAAATGGGTGATGGCCTGCACAATTTCAGCGATGGCCTAGCAATTG ss.DNA164647  1920       1930       1940       1950       1960       1970
              GTGCTGCTGCTTTTACTGAAGGCTTATCAAGTGGTTTAAGTACTTCTGTGTGCTGTTCTGTC ss.DNA164647  1980       1990       2000       2010       2020       2030
              ATGAGTTGCCTCATGAATTAGGTGACTTTGCTGTGTTCTACTAAAGGCTGACATGACCGTTA ss.DNA164647  2040       2050       2060       2070       2080       2090
              AGCAGGCTGTCCTTTATAATGCATTGTCAGCCATGCTGGCGTATCTTGGAATGGCAACAG ss.DNA164647  2100       2110       2120       2130       2140       2150
              GAATTTTCATTGGTCATTATGCTGAAAAATGTTTCTATGTGGATATTTGCACTTACTGCTG ss.DNA164647  2160       2170       2180       2190       2200       2210
              GCTTATTCATGTATGTTGCTCTCGGTTGATATGGTACCTGAAATGCTGCACAATGATGCTA ss.DNA164647  2220       2230       2240       2250       2260       2270
              GTGACCATGGATGTAGCCGCTGGGGGTATTCTTTTTACAGAATGCTGGGATGCTTTTGG ss.DNA164647  2280       2290       2300       2310       2320       2330
              GTTTTGGAATTATGTTACTTATTTCCATATTTGAACATAAAATCGTGTTTCGTATAAATT
```

FIG._2A-3

```
ss.DNA164647   2340      2350      2360      2370      2380      2390
               TCTAGTTAAGGTTTAAATGCTAGAGTAGCTTAAAAAGTTGTCATAGTTTCAGTAGGTCAT ss.DNA164647   2400      2410      2420      2430      2440      2450
               AGGGAGATGAGTTTGTTATGCTGTACTATGCAGCCGTTTAAAGTTAGTGGGTTTTGTGATTT ss.DNA164647   2460      2470      2480      2490      2500      2510
               TTGTATTGAATATTGCTGTCTGTTACAAAGTCAGTTAAAGGTACGTTTAATATTTAAGT ss.DNA164647   2520      2530      2540      2550      2560      2570
               TATTCTCTATCTTGGAGATAAAAATCTGTATGTGCAATTCACCGGTATTACCAGTTTATTATG ss.DNA164647   2580      2590      2600      2610      2620      2630
               TAAACAAGAGATTTGGCATGACATGTTCTGTATGTTTCAGGGAAAAATGTCTTTAATGCT ss.DNA164647   2640      2650      2660      2670      2680      2690
               TTTTCAAGAACTAACACAGTTATTCCTATACTGGATTTTAGGTCTCTGAAGAACTGCTGG ss.DNA164647   2700      2710      2720      2730      2740      2750
               TGTTTAGGAATAAGAATGTGCATGAAGCCTAAAATACCAAGAAAGCTTATACTGAATTTA ss.DNA164647   2760      2770
               AGCAAAAAAAAAAAAAAAAA
```

FIG. 2A-4

Met Ala Arg Lys Leu Ser Val Ile Leu Ile Leu Thr Phe Ala Leu
1               5                   10                  15

Ser Val Thr Asn Pro Leu His Glu Leu Lys Ala Ala Ala Phe Pro
                20                  25                  30

Gln Thr Thr Glu Lys Ile Ser Pro Asn Trp Glu Ser Gly Ile Asn
                35                  40                  45

Val Asp Leu Ala Ile Ser Thr Arg Gln Tyr His Leu Gln Gln Leu
                50                  55                  60

Phe Tyr Arg Tyr Gly Glu Asn Asn Ser Leu Ser Val Glu Gly Phe
                65                  70                  75

Arg Lys Leu Leu Gln Asn Ile Gly Ile Asp Lys Ile Lys Arg Ile
                80                  85                  90

His Ile His His Asp His Asp His His Ser Asp His Glu His His
                95                  100                 105

Ser Asp His Glu Arg His Ser Asp His Glu His His Ser Asp His
                110                 115                 120

Glu His His Ser Asp His Asp His His Ser His His Asn His Ala
                125                 130                 135

Ala Ser Gly Lys Asn Lys Arg Lys Ala Leu Cys Pro Asp His Asp
                140                 145                 150

Ser Asp Ser Ser Gly Lys Asp Pro Arg Asn Ser Gln Gly Lys Gly
                155                 160                 165

Ala His Arg Pro Glu His Ala Ser Gly Arg Arg Asn Val Lys Asp
                170                 175                 180

Ser Val Ser Ala Ser Glu Val Thr Ser Thr Val Tyr Asn Thr Val
                185                 190                 195

Ser Glu Gly Thr His Phe Leu Glu Thr Ile Glu Thr Pro Arg Pro
                200                 205                 210

Gly Lys Leu Phe Pro Lys Asp Val Ser Ser Thr Pro Pro Ser
                215                 220                 225

Val Thr Ser Lys Ser Arg Val Ser Arg Leu Ala Gly Arg Lys Thr
                230                 235                 240

Asn Glu Ser Val Ser Glu Pro Arg Lys Gly Phe Met Tyr Ser Arg
                245                 250                 255

FIG._2B-1

```
Asn Thr Asn Glu Asn Pro Gln Glu Cys Phe Asn Ala Ser Lys Leu
                    260             265                 270
Leu Thr Ser His Gly Met Gly Ile Gln Val Pro Leu Asn Ala Thr
                275             280                 285
Glu Phe Asn Tyr Leu Cys Pro Ala Ile Ile Asn Gln Ile Asp Ala
                290             295                 300
Arg Ser Cys Leu Ile His Thr Ser Glu Lys Lys Ala Glu Ile Pro
                305             310                 315
Pro Lys Thr Tyr Ser Leu Gln Ile Ala Trp Val Gly Gly Phe Ile
                320             325                 330
Ala Ile Ser Ile Ile Ser Phe Leu Ser Leu Leu Gly Val Ile Leu
                335             340                 345
Val Pro Leu Met Asn Arg Val Phe Phe Lys Phe Leu Leu Ser Phe
                350             355                 360
Leu Val Ala Leu Ala Val Gly Thr Leu Ser Gly Asp Ala Phe Leu
                365             370                 375
His Leu Leu Pro His Ser His Ala Ser His His Ser His Ser
                380             385                 390
His Glu Glu Pro Ala Met Glu Met Lys Arg Gly Pro Leu Phe Ser
                395             400                 405
His Leu Ser Ser Gln Asn Ile Glu Glu Ser Ala Tyr Phe Asp Ser
                410             415                 420
Thr Trp Lys Gly Leu Thr Ala Leu Gly Gly Leu Tyr Phe Met Phe
                425             430                 435
Leu Val Glu His Val Leu Thr Leu Ile Lys Gln Phe Lys Asp Lys
                440             445                 450
Lys Lys Lys Asn Gln Lys Lys Pro Glu Asn Asp Asp Asp Val Glu
                455             460                 465
Ile Lys Lys Gln Leu Ser Lys Tyr Glu Ser Gln Leu Ser Thr Asn
                470             475                 480
Glu Glu Lys Val Asp Thr Asp Asp Arg Thr Glu Gly Tyr Leu Arg
                485             490                 495
Ala Asp Ser Gln Glu Pro Ser His Phe Asp Ser Gln Gln Pro Ala
                500             505                 510
```

FIG._2B-2

```
Val Leu Glu Glu Glu Val Met Ile Ala His Ala His Pro Gln
            515             520             525
Glu Val Tyr Asn Glu Tyr Val Pro Arg Gly Cys Lys Asn Lys Cys
            530             535             540
His Ser His Phe His Asp Thr Leu Gly Gln Ser Asp Asp Leu Ile
            545             550             555
His His His His Asp Tyr His His Ile Leu His His His His His
            560             565             570
Gln Asn His His Pro His Ser His Ser Gln Arg Tyr Ser Arg Glu
            575             580             585
Glu Leu Lys Asp Ala Gly Val Ala Thr Leu Ala Trp Met Val Ile
            590             595             600
Met Gly Asp Gly Leu His Asn Phe Ser Asp Gly Leu Ala Ile Gly
            605             610             615
Ala Ala Phe Thr Glu Gly Leu Ser Ser Gly Leu Ser Thr Ser Val
            620             625             630
Ala Val Phe Cys His Glu Leu Pro His Glu Leu Gly Asp Phe Ala
            635             640             645
Val Leu Leu Lys Ala Asp Met Thr Val Lys Gln Ala Val Leu Tyr
            650             655             660
Asn Ala Leu Ser Ala Met Leu Ala Tyr Leu Gly Met Ala Thr Gly
            665             670             675
Ile Phe Ile Gly His Tyr Ala Glu Asn Val Ser Met Trp Ile Phe
            680             685             690
Ala Leu Thr Ala Gly Leu Phe Met Tyr Val Ala Leu Val Asp Met
            695             700             705
Val Pro Glu Met Leu His Asn Asp Ala Ser Asp His Gly Cys Ser
            710             715             720
Arg Trp Gly Tyr Phe Phe Leu Gln Asn Ala Gly Met Leu Leu Gly
            725             730             735
Phe Gly Ile Met Leu Leu Ile Ser Ile Phe Glu His Lys Ile Val
            740             745             750
Phe Arg Ile Asn Phe        (SEQ ID NO:4)
            755
```

FIG. 2B-3

```
ss.u41060          CTCGTGCCGAATTCGGCACGAGACCGCGTGTTCGCGCCTGGTAGAGATTTCTCGAAGACA
                             10        20        30        40        50        60 ss.DNA164647       CCGGCCGTGTGGAACCAAACCTGCGCCGCCGTGGCCGGGCCGTGGACAACGAGGCC
                   * * * * * * * * * * * * * * * * * * * * * * * * * * * * *
                            10        20        30        40        50 ss.u41060          CCAGTGGGCCCGTGTGGAACCAAACCTGCGCGCCGTGGCCGTGGCCGGGACAACGAGGCC
                            70        80        90       100       110       120 ss.DNA164647       GCGGAGACGAAGGCGCAATGGCGAGGAAGTTATCTGTAATCTTGATCCTTGACCTTTGCCC
                   * * * * * * * * * * * * * * * * * * * * * * * * * * * * *
                            60        70        80        90       100       110 ss.u41060          GCGGGAGACGAAGGCGCAATGGCGAGGAAGTTATCTGTAATCTTGATCCTTGACCTTTGCCC
                           130       140       150       160       170       180 ss.DNA164647       TCTCTGTCACAAATCCCCTTCATGAACTAAAAGCAGCTGCTTTCCCCCAGACCACTGAGA
                   * * * * * * * * * * * * * * * * * * * * * * * * * * * * *
                           120       130       140       150       160       170 ss.u41060          TCTCTGTCACAAATCCCCTTCATGAACTAAAAGCAGCTGCTTTCCCCCAGACCACTGAGA
                           190       200       210       220       230       240 ss.DNA164647       AAATTAGTCCGAATTGGGAATCTGGCATTAATGTTGACTTGCAATTTCCACACGGCAAT
                   * * * * * * * * * * * * * * * * * * * * * * * * * * * * *
                           180       190       200       210       220       230 ss.u41060          AAATTAGTCCGAATTGGGAATCTGGCATTAATGTTGACTTGCAATTTCCACACGGCAAT
                           250       260       270       280       290       300 ss.DNA164647       ATCATCTACAACAGCTTTTCTACCGCTATGGAGAAAATAATTCTTTGTCAGTTGAAGGGT
                   * * * * * * * * * * * * * * * * * * * * * * * * * * * * *
                           240       250       260       270       280       290 ss.u41060          ATCATCTACAACAGCTTTTCTACCGCTATGGAGAAAATAATTCTTTGTCAGTTGAAGGGT
                           310       320       330       340       350       360 ss.DNA164647       TCAGAAAATTACTTCAAAATATAGGCATAGATAAGATTAAAAGAATCCATATACACCATG
                   * * * * * * * * * * * * * * * * * * * * * * * * * * * * *
                           300       310       320       330       340       350 ss.u41060          TCAGAAAATTACTTCAAAATATAGGCATAGATAAGATTAAAAGAATCCATATACACCATG
                           370       380       390       400       410       420
```

FIG._3A-1

```
ss.DNA164647    ACCACGACCATCACTCAGACCATCACTCAGACCACGAGCATCACTGAGCATCACTCAGACCATGAGCGTCACTCAGACCATG
                   360       370       380       390       400       410
ss.u41060       ACCACGACCATCACTCAGACCACGAGCATCACTGAGCGTCACTCAGACCATG
                   430       440       450       460       470       480 ss.DNA164647    AGCATCACTCAGACCACGAGCATCACTGAGCATCACTCTGACCATGATCATCACTCCCACCATAATCATG
                   420       430       440       450       460       470
ss.u41060       AGCATCACTCAGACCACGAGCATCACTGAGCATCACTCTG----------ACCATAATCATG
                   490       500       510             520 ss.DNA164647    CTGCTTCTGGTAAAAATAAGCGAAAAAGCTCTTTGCCCAGAGACCATGACTCAGATAGTTCAG
                   480       490       500       510       520       530
ss.u41060       CTGCTTCTGGTAAAAATAAGCGAAAAAGCTCTTTGCCCAGAGACCATGACTCAGATAGTTCAG
                   530       540       550       560       570       580 ss.DNA164647    GTAAAGATCCTAGAAACAGCCAGTGTTAGTGCTAGTGAAGTGACCTCAACTGTGTACAACACTG
                   540       550       560       570       580       590
ss.u41060       GTAAAGATCCTAGAAACAGCCAGTGTTAGTGCTAGTGAAGTGACCTCAACTGTGTACAACACTG
                   590       600       610       620       630       640 ss.DNA164647    GAAGGAATGTCAAGGACAGTGTTAGTGCTAGTGAAGTGACCTCAACTGTGTACAACACTG
                   600       610       620       630       640       650
ss.u41060       GAAGGAATGTCAAGGACAGTGTTAGTGCTAGTGAAGTGACCTCAACTGTGTACAACACTG
                   650       660       670       680       690       700 ss.DNA164647    TCTCTGAAGGAACTCACTTTCTAGAGACAATAGAGACTCCAAGACCTGGAAAACTCTTCC
                   660       670       680       690       700       710
ss.u41060       TCTCTGAAGGAACTCACTTTCTAGAGACAATAGAGACTCCAAGACCTGGAAAACTCTTCC
                   710       720       730       740       750       760
```

*FIG._3A-2*

```
ss.DNA164647    CCAAAGATGTAAGCAGCTCCACTCCACCCAGTGTCACATCAAAGAGCCGGGTGAGCCGGC
                    720       730       740       750       760       770
                ************************************************************
ss.u41060       CCAAAGATGTAAGCAGCTCCACTCCACCCAGTGTCACATCAAAGAGCCGGGTGAGCCGGC
                    770       780       790       800       810       820 ss.DNA164647    TGGCTGGTAGGAAAACAAATGAATCTGTGAGTGAGCCCCGAAAAGGCTTTATGTATTCCA
                    780       790       800       810       820       830
                ************************************************************
ss.u41060       TGGCTGGTAGGAAAACAAATGAATCTGTGAGTGAGCCCCGAAAAGGCTTTATGTATTCCA
                    830       840       850       860       870       880 ss.DNA164647    GAAACACAAATGAAAAATCCTCAGGAGTGTTTCAATGCATCAAAGCTACTGACATCTCATG
                    840       850       860       870       880       890
                ************************************************************
ss.u41060       GAAACACAAATGAAAAATCCTCAGGAGTGTTTCAATGCATCAAAGCTACTGACATCTCATG
                    890       900       910       920       930       940 ss.DNA164647    GCATGGGCATCCAGGTTCCGCTAGATCTTGTCTGATTCATACAAGTTCAACTATCTCTGTCCAGCCATCA
                    900       910       920       930       940       950
                ************************************************************
ss.u41060       GCATGGGCATCCAGGTTCCGCTAGATCTTGTCTGATTCATACAAGTTCAACTATCTCTGTCCAGCCATCA
                    950       960       970       980       990      1000 ss.DNA164647    TCAACCAAATTGATGCTAGATGCTAGAATCATTACAAATAGCCTGGTTGGTTTTATACAAGTGAAAAGAAGGCTGAAATCC
                    960       970       980       990      1000      1010
                ************************************************************
ss.u41060       TCAACCAAATTGATGCTAGATGCTAGAATCATTACAAATAGCCTGGTTGGTTTTATACAAGTGAAAAGAAGGCTGAAATCC
                   1010      1020      1030      1040      1050      1060 ss.DNA164647    CTCCAAAGACCTATTCATTACAAATAGCCTGGGTTGGTGGTTTTTATAGCCATTTCCATCA
                   1020      1030      1040      1050      1060      1070
                ************************************************************
ss.u41060       CTCCAAAGACCTATTCATTACAAATAGCCTGGGTTGGTGGTTTTTATAGCCATTTCCATCA
                   1070      1080      1090      1100      1110      1120
```

FIG._3A-3

```
ss.DNA164647    1080      1090      1100      1110      1120      1130
                TCAGTTTCCTGTCTCTGCTCTGGGGGTTATCTTAGTGCCTCTCATGAATCGGGTGTTTTCA
                ************************************************************
ss.u41060       TCAGTTTCCTGTCTCTGCTCTGGGGGTTATCTTAGTGCCTCTCATGAATCGGGTGTTTTCA
                1130      1140      1150      1160      1170      1180 ss.DNA164647    1140      1150      1160      1170      1180      1190
                AATTTCTCCTGAGTTTCCTTGTGGCACTGGCCGTTGGGACTTTGAGTGGTGATGCTTTTT
                ************************************************************
ss.u41060       AATTTCTCCTGAGTTTCCTTGTGGCACTGGCCGTTGGGACTTTGAGTGGTGATGCTTTTT
                1190      1200      1210      1220      1230      1240 ss.DNA164647    1200      1210      1220      1230      1240      1250
                TACACCTTCTTCCACATTCTCATGCAAGTCACCACCATAGTCATAGCCATGAAGAACCAG
                ************************************************************
ss.u41060       TACACCTTCTTCCACATTCTCATGCAAGTCACCACCATAGTCATAGCCATGAAGAACCAG
                1250      1260      1270      1280      1290      1300 ss.DNA164647    1260      1270      1280      1290      1300      1310
                CAATGGAAATGAAAAGAGGACCACTTTTCAGTCATCTGTCTTCTCAAAACATAGAAGAAA
                ************************************************************
ss.u41060       CAATGGAAATGAAAAGAGGACCACTTTTCAGTCATCTGTCTTCTCAAAACATAGAAGAAA
                1310      1320      1330      1340      1350      1360 ss.DNA164647    1320      1330      1340      1350      1360      1370
                GTGCCTATTTTGATTCCACGTGGAAGGGTCTAACAGCTCTAGGAGGCCTGTATTTCATGT
                ************************************************************
ss.u41060       GTGCCTATTTTGATTCCACGTGGAAGGGTCTAACAGCTCTAGGAGGCCTGTATTTCATGT
                1370      1380      1390      1400      1410      1420 ss.DNA164647    1380      1390      1400      1410      1420      1430
                TTCTTGTTGAACATGTCCTCACATTGATCAAACAATTTAAAGATAAGAAGAAAAAGAATC
                ************************************************************
ss.u41060       TTCTTGTTGAACATGTCCTCACATTGATCAAACAATTTAAAGATAAGAAGAAAAAGAATC
                1430      1440      1450      1460      1470      1480
```

FIG._3A-4

```
ss.DNA164647  AGAAGAAACCTGAAAAATGATGATGTGAGATTAAGAAGCAGTTGTCCAAGTATGAAT
              1440      1450      1460      1470      1480      1490
              **********************************************************
ss.u41060     AGAAGAAACCTGAAAAATGATGATGTGAGATTAAGAAGCAGTTGTCCAAGTATGAAT
              1490      1500      1510      1520      1530      1540 ss.DNA164647  CTCAACTTTCAACAAATGAGGAGAAAGTAGATACAGATGATGATCGAACTGAAGGCTATTTAC
              1500      1510      1520      1530      1540      1550
              **********************************************************
ss.u41060     CTCAACTTTCAACAAATGAGGAGAGAAAGTAGATACAGATGATGATCGAACTGAAGGCTATTTAC
              1550      1560      1570      1580      1590      1600 ss.DNA164647  GAGCAGACTCACAAGAGCCCCTCCCACTTTGATTCTCAGCAGCCTGCAGTCTTGGAAGAAG
              1560      1570      1580      1590      1600      1610
              **********************************************************
ss.u41060     GAGCAGACTCACAAGAGCCCCTCCCACTTTGATTCTCAGCAGCCTGCAGTCTTGGAAGAAG
              1610      1620      1630      1640      1650      1660 ss.DNA164647  AAGAGGTCATGATAGCTCATGCTCATCCACAGGAAGTCTACAATGAATATGTACCCAGAG
              1620      1630      1640      1650      1660      1670
              **********************************************************
ss.u41060     AAGAGGTCATGATAGCTCATGCTCATCCACAGGAAGTCTACAATGAATATGTACCCAGAG
              1670      1680      1690      1700      1710      1720 ss.DNA164647  GGTGCAAGAATAAATGCCATTCACATTTCCACGATACACTCGGCCAGTCAGACGATCTCA
              1680      1690      1700      1710      1720      1730
              **********************************************************
ss.u41060     GGTGCAAGAATAAATGCCATTCACATTTCCACGATACACTCGGCCAGTCAGACGATCTCA
              1730      1740      1750      1760      1770      1780 ss.DNA164647  TTCACCACCATCATGACTACCATCATTCTCCATCATCACCACCAAAACCACCATC
              1740      1750      1760      1770      1780      1790
              **********************************************************
ss.u41060     TTCACCACCATCATGACTACCATCATTCTCCATCATCACCACCAAAACCACCATC
              1790      1800      1810      1820      1830      1840
```

FIG._3A-5

```
                     1800        1810        1820        1830        1840        1850
ss.DNA164647    CTCACAGTCACAGCCAGCGCTACTCTCGGGAGGAGCTGAAAGATGCCGGCGTCGCCACTT
                ************************************************************
ss.u41060       CTCACAGTCACAGCCAGCGCTACTCTCGGGAGGAGCTGAAAGATGCCGGCGTCGCCACTT
                     1850        1860        1870        1880        1890        1900

1860        1870        1880        1890        1900        1910
ss.DNA164647    TGGCCTGGATGGTGATAATGGGTGATGGCCTGCACAATTTCAGCGATGGCCTAGCAATTG
                ************************************************************
ss.u41060       TGGCCTGGATGGTGATAATGGGTGATGGCCTGCACAATTTCAGCGATGGCCTAGCAATTG
                     1910        1920        1930        1940        1950        1960

1920        1930        1940        1950        1960        1970
ss.DNA164647    GTGCTGCTTTTACTGAAGGCTTATCAAGTGGTTTAAGTACTTCTGTTGCTGTTGTTCTGTC
                ************************************************************
ss.u41060       GTGCTGCTTTTACTGAAGGCTTATCAAGTGGTTTAAGTACTTCTGTTGCTGTTGTTCTGTC
                     1970        1980        1990        2000        2010        2020

1980        1990        2000        2010        2020        2030
ss.DNA164647    ATGAGTTGCCTCATGAATTAGGTGACTTTGCTGTCTTCTACTAAAGGCTGACATGACCGTTA
                ************************************************************
ss.u41060       ATGAGTTGCCTCATGAATTAGGTGACTTTGCTGTCTTCTACTAAAGGCTGACATGACCGTTA
                     2030        2040        2050        2060        2070        2080

2040        2050        2060        2070        2080        2090
ss.DNA164647    AGCAGGCTGTCCTTTATAATGCATTGTCAGCCATGCTGGCGTATCTTGGAATGGCAACAG
                ************************************************************
ss.u41060       AGCAGGCTGTCCTTTATAATGCATTGTCAGCCATGCTGGCGTATCTTGGAATGGCAACAG
                     2090        2100        2110        2120        2130        2140

2100        2110        2120        2130        2140        2150
ss.DNA164647    GAATTTCATTGGTCATTATGCTGAAAATGTTTCTATGTGGATATTTGCACTTACTGCTG
                ************************************************************
ss.u41060       GAATTTCATTGGTCATTATGCTGAAAATGTTTCTATGTGGATATTTGCACTTACTGCTG
                     2150        2160        2170        2180        2190        2200
```

*FIG._3A-6*

```
ss.DNA164647  2160      2170      2180      2190      2200      2210
              GCTTATTCATGTATGTTGCTCTGGTTGATATGGTACCTGAAATGCTGCACAATGATGCTA
              ************************************************************
ss.u41060     GCTTATTCATGTATGTTGCTCTGGTTGATATGGTACCTGAAATGCTGCACAATGATGCTA
              2210      2220      2230      2240      2250      2260 ss.DNA164647  2220      2230      2240      2250      2260      2270
              GTGACCATGGATGTAGCCGCTGGGGGTATTCTTTTTACAGAATGCTGGGATGCTTTTGG
              ***********************************************************
ss.u41060     GTGACCATGGATGTAGCCGCTGGGGGTATTCTTTTTACAGAATGCTGGGATGCTTTTGG
              2270      2280      2290      2300      2310      2320 ss.DNA164647  2280      2290      2300      2310      2320      2330
              GTTTTGGAATTATGTTACTTATTTCCATATATTGAACATAAAAATCGTGTTTCGTATAAATT
              **********************           *******************   *******
ss.u41060     GTTTTGGAATTATGTTACTTA-TTCCATATATTGAACATAAAAATCGTG-TTCGTATAAATT
              2330      2340      2350      2360      2370      2380 ss.DNA164647  2340      2350      2360      2370      2380      2390
              TCTAGTTAAGGTTTAAAATGCTAGAGTAGCTTAAAAAGTTGTCATAGTTTCAGTAGGTCAT
              ************************************************************
ss.u41060     TCTAGTTAAGGTTTAAAATGCTAGAGTAGCTTAAAAAGTTGTCATAGTTTCAGTAGGTCAT
              2390      2400      2410      2420      2430      2440 ss.DNA164647  2400      2410      2420      2430      2440      2450
              AGGGAGAGATGAGTTTGTCTGTGTACTATGCAGCCGTTTAAAGTTAGTGGGTTTTGTGATTT
              ************************************************************
ss.u41060     AGGGAGAGATGAGTTTGTCTGTGTACTATGCAGCCGTTTAAAGTTAGTGGGTTTTGTGATTT
              2450      2460      2470      2480      2490      2500 ss.DNA164647  2460      2470      2480      2490      2500      2510
              TTGTATTGAATATTGCTGTCTGTTACAAAGTCAGTTACGTTTTAATATTTAAGT
              ******************************************************
ss.u41060     TTGTATTGAATATTGCTGTCTGTTACAAAGTCAGTTACGTTTTAATATTTAAGT
              2510      2520      2530      2540      2550      2560
```

FIG._3A-7

```
ss.DNA164647   2520      2530      2540      2550      2560      2570
               TATTCTATCTTGGAGATAAAATCTGTATGTGCAATTCACCGGTATTACCAGTTTATTATG
               ************************************************************
ss.u41060      TATTCTATCTTGGAGATAAAATCTGTATGTGCAATTCACCGGTATTACCAGTTTATTATG
               2570      2580      2590      2600      2610      2620 ss.DNA164647   2580      2590      2600      2610      2620      2630
               TAAACAAGAGATTTGGCATGACATGTTCTGTATGTTTCAGGGAAAAAATGTCTTTAATGCT
               ************************************************************
ss.u41060      TAAACAAGAGATTTGGCATGACATGTTCTGTATGTTTCAGGGAAAAAATGTCTTTAATGCT
               2630      2640      2650      2660      2670      2680 ss.DNA164647   2640      2650      2660      2670      2680      2690
               TTTTCAAGAACTAACACACAGTTATTCCTATACTGGATTTTAGGTCTCTGAAGAACTGCTGG
               ************************************************************
ss.u41060      TTTTCAAGAACTAACACACAGTTATTCCTATACTGGATTTTAGGTCTCTGAAGAACTGCTGG
               2690      2700      2710      2720      2730      2740 ss.DNA164647   2700      2710      2720      2730      2740      2750
               TGTTTAGGAATAAGAATGTGCATGAAGCCTAAAATACCAAGAAAGCTTATACTGAATTTA
               ************************************************************
ss.u41060      TGTTTAGGAATAAGAATGTGCATGAAGCCTAAAATACCAAGAAAGCTTATACTGAATTTA
               2750      2760      2770      2780      2790      2800 ss.DNA164647   2760      2770
               AGCAAAAAAAAAAAAAAAAAA   (SEQ ID NO:3)
               *******  ****  *  ***
ss.u41060      AGCAAAATAAAGGAGAAAAAGAGAAAAAGAGAATCTGAGAATTGGGGAGGCATAGATTCTTAT
               2810      2820      2830      2840      2850      2860 ss.u41060      AAAAATCACAAAATTTGTTGTAAATTAGAGGGGAGAAATTTAGAATTAAGTATAAAAAGG
               2870      2880      2890      2900      2910      2920
```

FIG._3A-8

```
ss.u41060  CAGAATTAGTAGTATAGAGTACATTCATTAAACATTTTGTCAGGATTATTCCCGTAAAAAC
               2930      2940      2950      2960      2970      2980 ss.u41060  GTAGTGAGCACTCTCATATACTAATTAGTGTACATTTAACTTTGTATAAATACAGAAATCT
               2990      3000      3010      3020      3030      3040 ss.u41060  AAATATATTTAATGAATTCAAGCAATATACACTTGACCAAGAAATTGGAATTTCAAAATG
               3050      3060      3070      3080      3090      3100 ss.u41060  TTCGTGCGGGTTATATACCAGATGAGTAGTAGTTTATGTATCACCAGACTGGGT
               3110      3120      3130      3140      3150      3160 ss.u41060  TATTGCCAAGTTATATATCACCAAAAGCTGTATGACTGGATGTTCTGGTTACCTGGTTTA
               3170      3180      3190      3200      3210      3220 ss.u41060  CAAAATTATCAGAGTAGTAAAACTTTGATATATATGAGGATATTAAAACTACACTAAGTA
               3230      3240      3250      3260      3270      3280 ss.u41060  TCATTTGATTCGATTCAGAAAGTACTTTGATATCTCTCAGTGCTTCAGTGCTATCATTGT
               3290      3300      3310      3320      3330      3340 ss.u41060  GAGCAATTGTCTTTATATACGGTACTGTAGCCATACTAGGCCTGTCTGTGGCATTCTCTA
               3350      3360      3370      3380      3390      3400 ss.u41060  GATGTTTCTTTTTTACACAATAAATTCCTTATATCAGCTTGAAAAAAAAAAAAAAAAA
               3410      3420      3430      3440      3450      3460

A  (SEQ ID NO:1)
```

FIG._3A-9

```
pl.164647   MARKLSVILILTFALSVTNPLHELKAAAFPQTTEKISPNWESGINVDLAISTRQYHLQQL   60
            ************************************************************
pl.H00961   MARKLSVILILTFALSVTNPLHELKAAAFPQTTEKISPNWESGINVDLAISTRQYHLQQL   60 pl.164647   FYRYGENNSLSVEGFRKLLQNIGIDKIKRIHIHHDHDHHSDHERHSDHEHHSDH------   120
            *********************************       *********
pl.H00961   FYRYGENNSLSVEGFRKLLQNIGIDKIKRIHIHHDHDHHSDHEHHSDRERHSDHEHHSDH   120 pl.164647   EHHSDHDHHSHHNHAASGKNKRKALCPDHDSDSSGKDPRNSQGKGAHRPEHASGRRNVKD   180
            ***           *****************************************
pl.H00961   EHHSD-----HNHAASGKNKRKALCPDHDSDSSGKDPRNSQGKGAHRPEHASGRRNVKD   170 pl.164647   SVSASEVTSTVYNTVSEGTHFLETIETPRPGKLFPKDVSSSTPPSVTSKSRVSRLAGRKT   240
            ************************************************************
pl.H00961   SVSASEVTSTVYNTVSEGTHFLETIETPRPGKLFPKDVSSSTPPSVTSKSRVSRLAGRKT   230 pl.164647   NESVSEPRKGFMYSRNTNENPQECFNASKLLTSHGMGIQVPLNATEFNYLCPAIINQIDA   300
            ************************************************************
pl.H00961   NESVSEPRKGFMYSRNTNENPQECFNASKLLTSHGMGIQVPLNATEFNYLCPAIINQIDA   290 pl.164647   RSCLIHTSEKKAEIPPKTYSLQIAWVGGFIAISIISFLSLLGVILVPLMNRVFFKFLLSF   360
            ************************************************************
PI.H00961   RSCLIHTSEKKAEIPPKTYSLQIAWVGGFIAISIISFLSLLGVILVPLMNRVFFKFLLSF   350 pl.164647   LVALAVGTLSGDAFLHLLPHSHASHHHSHSHEEPAMEMKRGPLFSHLSSQNIEESAYFDS   420
            ************************************************************
pl.H00961   LVALAVGTLSGDAFLHLLPHSHASHHHSHSHEEPAMEMKRGPLFSHLSSQNIEESAYFDS   410
```

FIG._4-1

```
p1.164647   TWKGLTALGGLYFMFLVEHVLTLIKQFKDKKKKNQKKPENDDDVEIKKQLSKYESQLSTN
                430       440       450       460       470       480
            ************************************************************
p1.H00961   TWKGLTALGGLYFMFLVEHVLTLIKQFKDKKKKNQKKPENDDDVEIKKQLSKYESQLSTN
                420       430       440       450       460       470 p1.164647   EEKVDTDDRTEGYLRADSQEPSHFDSQQPAVLEEEVMIAHAHPQEVYNEYVPRGCKNKC
                490       500       510       520       530       540
            ************************************************************
p1.H00961   EEKVDTDDRTEGYLRADSQEPSHFDSQQPAVLEEEVMIAHAHPQEVYNEYVPRGCKNKC
                480       490       500       510       520       530 p1.164647   HSHFHDTLGQSDDLIHHHHDYHHILHHHHHQNHHPHSHSQRYSREELKDAGVATLAWMVI
                550       560       570       580       590       600
            ************************************************************
p1.H00961   HSHFHDTLGQSDDLIHHHHDYHHILHHHHHQNHHPHSHSQRYSREELKDAGVATLAWMVI
                540       550       560       570       580       590 p1.164647   MGDGLHNFSDGLAIGAAFTEGLSSGLSTSVAVFCHELPHELGDFAVLLKADMTVKQAVLY
                610       620       630       640       650       660
            ********************************************* .************
p1.H00961   MGDGLHNFSDGLAIGAAFTEGLSSGLSTSVAVFCHELPHELGDFAVLLKAGMTVKQAVLY
                600       610       620       630       640       650 p1.164647   NALSAMLAYLGMATGIFIGHYAENVSMWIFALTAGLFMYVALVDMVPEMLHNDASDHGCS
                670       680       690       700       710       720
            ************************************************************
p1.H00961   NALSAMLAYLGMATGIFIGHYAENVSMWIFALTAGLFMYVALVDMVPEMLHNDASDHGCS
                660       670       680       690       700       710 p1.164647   RWGYFFLQNAGMLLGFGIMLLISIFEHKIVFRINF                 (SEQ ID NO:4)
                730       740       750
            *********************** .. .: .    *
p1.H00961   RWGYFFLQNAGMLLGFGIMLLIPYLNIKSC-SYKFLVKV             (SEQ ID NO:2)
                720       730       740       750
```

FIG._4-2

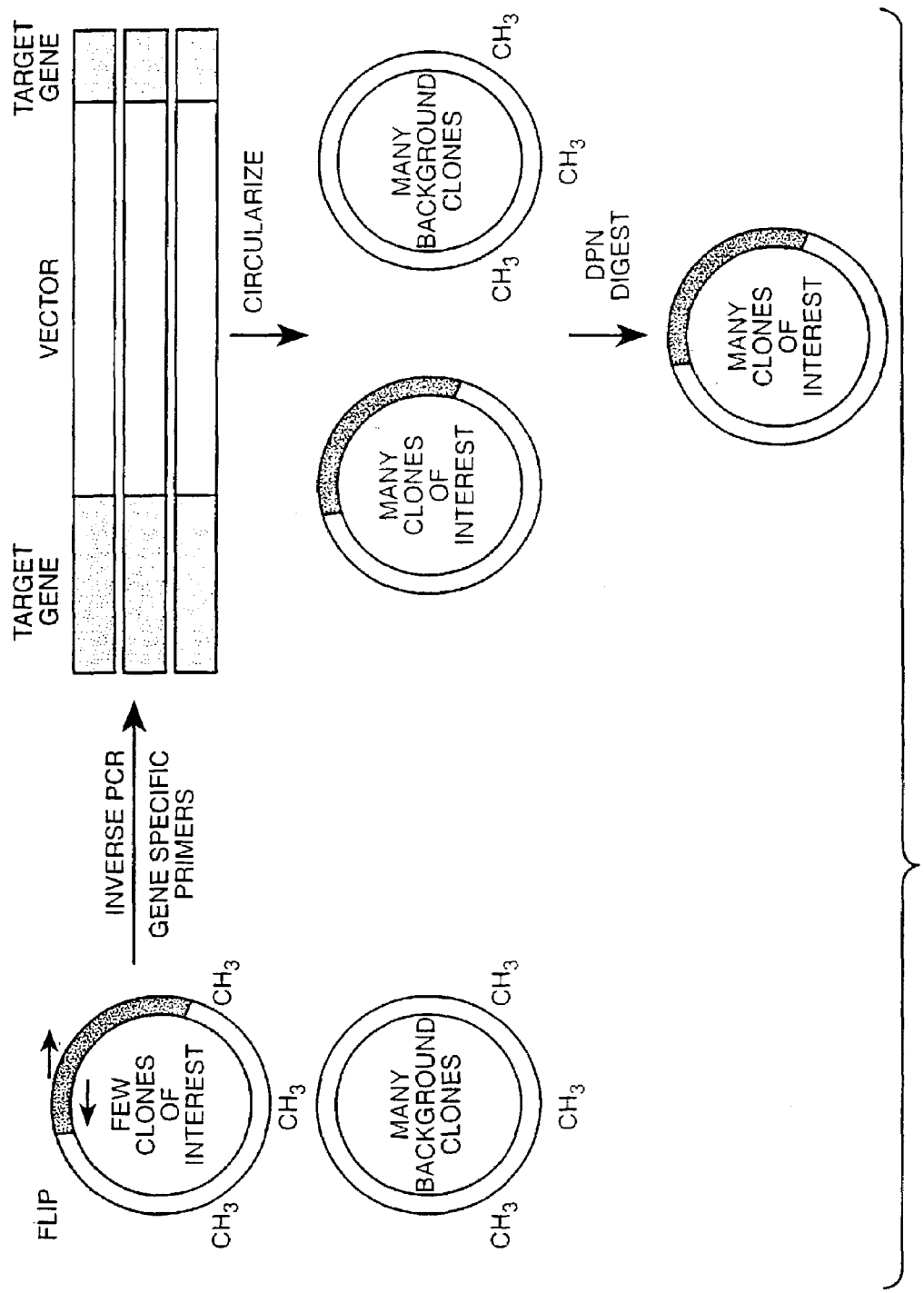
FIG._5

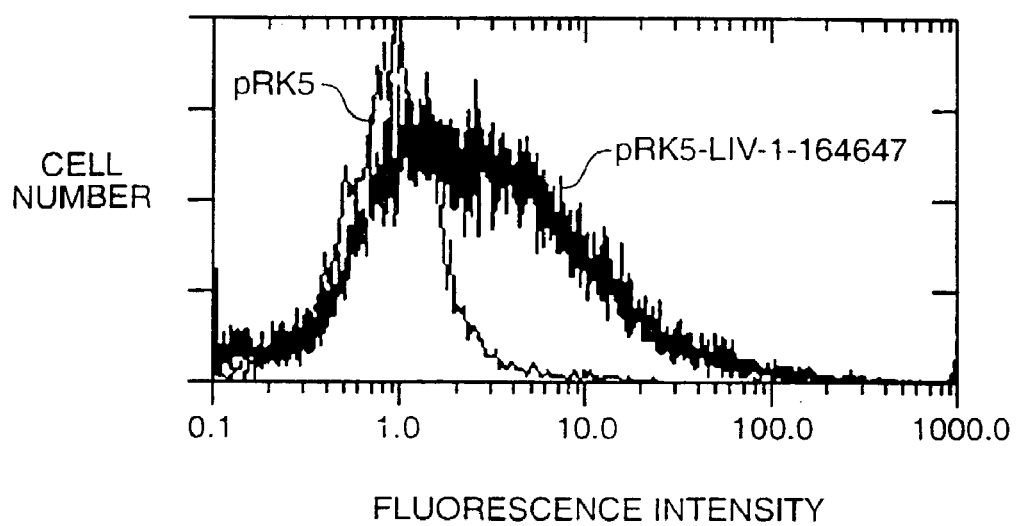
FIG._6
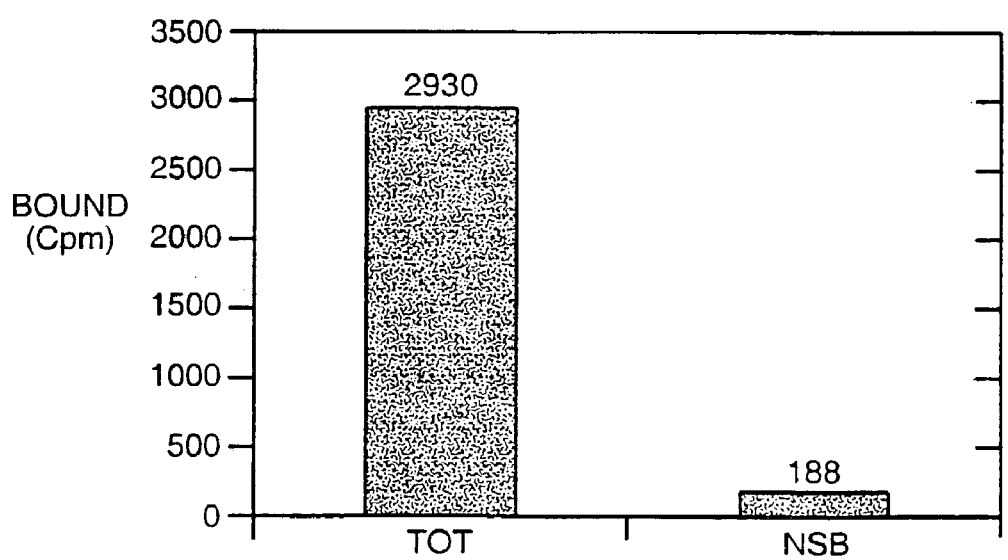
FIG._7

COMPOSITIONS AND METHODS FOR TREATMENT OF CANCER

This application was filed under 35 U.S.C. § 37 1(e) from PCT/US01/02622, filed 25 Jan. 2001, which claims priority under 35 U.S.C. § 119(e) to provisional application Ser. No. 60/177,951, filed 25 Jan. 2000 and provisional application Ser. No. 60/195,761, filed 10 Apr. 2000.

FIELD OF THE INVENTION

The present invention concerns compositions and methods for the treatment of disorders characterized by the overexpression of a LIV-1 gene product in tumors. The compositions comprise a nucleic acid, a polypeptide encoded by the nucleic acid, and a compound, preferably an antibody or fragment thereof, that binds to the polypeptide, preferably binding to the extracellular domain of LIV-1 polypeptide.

BACKGROUND OF THE INVENTION

Breast cancer is a common and devastating form of cancer, affecting millions of women per year throughout the world. Many breast tumors are estrogen sensitive and frequently treatable with compounds that interfere with estrogen binding to estrogen receptors (ERs) expressed on the breast tumor tissue. Detecting the level of ER expression and sensitivity to estrogen stimulation is useful for determining that antihormone-type chemotherapy may succeed in a particular patient.

The overexpression of estrogen-inducible genes, pLIV-1 and pLIV2 (also designated pS2), occurs in some breast tumors which also express the estrogen receptor, (Manning D. L. et al. European J. Cancer 29A(10): 1462-1468 (1993): Manning. D. L. et al., European J. Cancer 30A(5):675-678 (1994); Manning. D. L. et al. Acta Oncologica 34 (5):641-646 (1995); Manning, D. L. et al., U.S. Pat. No. 5,693,465). Expression of pLIV-1, but not pS2, is associated with metastasis of breast cancer cells to regional lymph nodes (Manning et al. U.S. Pat. No. 5,692,465).

In addition, the pathogenesis of various human malignancies, including breast cancer, is affected by proto-oncogenes that encode growth factors and growth factor receptors. Human ErbB2 gene (erbB2, also known as her2, or c-erbB-2), which encodes a 185-kd transmembrane glycoprotein receptor (ErbB2, also known as HER2 or p185$^{HER2}$) related to the epidermal growth factor receptor (EGFR), is overexpressed in about 25% to 30% of human breast cancer (Slamon et al., Science 235:177-182 [1987]: Slamon et al. Science 244:707-712 [1989]).

Several lines of evidence support a direct role for ErbB2 in the pathogenesis and clinical aggressiveness of ErbB2-overexpressing tumors. The introduction of ErbB2 into non-neoplastic cells causes their malignant transformation (Hudziak et al. Proc. Natl. Acad. Sci. USA 84:7159-7163 [1987]; DiFiore et al., Science 237:78-182 [1987]). Transgenic mice that express ErbB2 develop mammary tumors (Guy et al., Proc. Natl. Acad. Sci. USA 89:10578-10582 [1992]). ErbB2 overexpression is commonly regarded as a predictor of a poor prognosis in humans, especially in patients with primary disease that involves axillary lymph nodes (Slamon et al. [1987] and [1989], supra: Ravdin and Chamness, Gene 159:19-27 [1995]; and Hynes and Stern, Biochim Biophys Acta 1198:165-184 [1994]).

Antibodies directed against human erbB2 protein products (anti-ErbB2 antibodies) and against proteins encoded by the rat equivalent of the erbB2 gene (neu) (anti-neu protein antibodies) down-modulate cell surface expression of p185 on B104-1-1 cells (NIH-3T3 cells transfected with the neu proto-oncogene) and inhibit colony formation of these cells, Drebin et al., Cell 41:695-706 (1985). Biological effects of anti-neu protein antibodies are reviewed in Myers et al., Meth. Enzym. 198:277-290 (1991). See also WO94/22478 published Oct. 13, 1994.

The anti-ErbB2 antibody, 4D5, exhibited anti proliferative effects on the SKDR3 human breast tumor cell line, inhibiting cellular proliferation by approximately 56%, and sensitizing p185$^{erbB2}$-overexpressing breast tumor cell lines to the cytotoxic effects of TNF-α. See Hudziak et al., Mol. Cell. Biol. 9(3):1165-1172(1989). See also WO89/06692 published Jul. 27, 1989. The anti-ErbB2 antibodies discussed in Hudziak et al. are further characterized in Fendly et al. Cancer Research 50:1550-1558 (1990); Kotts et al. In Vitro 26(3):59A (1990): Sarup et al. Growth Regulation 1:72-82 (1991): Shepard et al. J. Clin. Immunol. 11(3): 117-127 (1991): Kumar et al. Mol. Cell. Biol. 11(2):979-986 (1991); Lewis et al. Cancer Immunol. Immunother. 37:255-263 (1993); Pietras et al. Oncogene 9:1829-1838 (1994); Vitetta et al. Cancer Research 54:5301-5309 (1994); Sliwkowski et al. J. Biol. Chem. 269(20):14661-14665 (1994): Scott et al. J. Biol. Chem. 266:14300-5 (1991); and D'souza et al. Proc. Natl. Acad. Sci. 91:7202-7206 (1994).

ErbB2 overexpression is also linked to sensitivity and/or resistance to hormone therapy and chemotherapeutic regimens, including CMF (cyclophosphamide, methotrexate, and fluoruracil) and anthracyclines (Baselga et al., Oncology 11(3 Suppl 1):43-48 [1997]). Despite the association of ErbB2 overexpression with poor prognosis, the odds of HER2-positive patients responding clinically to treatment with taxanes were greater than three times those of HER2-negative patients (Ibid), rhuMab HER2 was shown to enhance the activity of paclitaxel (TAXOL®) and doxorubicin against breast cancer xenografts in nude mice injected with BT-474 human breast adenocarcinoma cells, which express high levels of HER2 (Baselga et al. Breast Cancer, Proceedings of ASCO, Vol. 13. Abstract 53 [1994]).

Because breast and other cancers pose constant threats to health, there is a continuing need to develop treatments for cancers by using methods that target cancer cells without simultaneously harming large numbers of non-cancerous cells, thereby limiting adverse side effects associated with traditional cancer chemotherapy.

SUMMARY OF THE INVENTION

The present invention relates to the discovery of a unique protein. LIV-1-164647, that is overexpressed in some tumor tissues, such as in prostate, colon, lung, breast, and a population of breast tumors that overexpress LIV-1-164647, but do not overexpress ErbB2. The present invention further relates to nucleic acid sequences and amino acid sequences having homology to herein disclosed LIV-1 gene sequence (designated DNA 164647) and the amino acid sequence of LIV-1 protein encoded by DNA 164647. Applicants' discovery that LIV-1-164647 is overexpressed in tumor cells led to the additional discoveries of compositions for detection and treatment of tumor cells and methods of carrying out such detection and treatment.

In one aspect, the present invention relates to a nucleic acid sequence having homology to the nucleic acid sequence of DNA 164647 (SEQ ID NO:3 (coding strand)), or a portion thereof. Preferably the homology is at least approximately 80% homology, more preferably at least approximately 90%, still more preferably at least approximately 95%, and most preferably at least approximately 97% homology. Preferably, the nucleic acid of the invention encodes an aqueous soluble extracellular domain (ECD) that is at least 80% homologous to the DNA 164647 (SEQ ID NO:3) from approximately nucleic acid 73 to approximately 1060. Preferably, the homologous nucleic acid of the invention hybridizes under stringent conditions to a 30 nucleic acid or longer portion of the nucleic acid sequence of DNA 164647 (SEQ ID NO:3) or its complementary sequence, preferably hybridizing under stringent conditions to a 30 nucleotide regions from nucleotide 440 to and including nucleotide 470 of SEQ ID NO:3, or its complementary sequence. In a related embodiment, the homologous nucleic acid of the invention comprises a nucleic acid sequence comprising a sequence that is at least 50%, preferably at least 80%, more preferably at least 90% homologous to the sequence from nucleotide 446 to and including nucleotide 463 of SEQ ID NO:3, or a sequence from nucleotide 2297 to and including 2337 of SEQ ID NO:3, or both sequences. Most preferably, the isolated nucleic acid comprises a sequence from nucleotide 446 to and including nucleotide 464 and/or from nucleotide 2297 to and including 2337. According to the presently disclosed invention, the isolated nucleic acid of the invention comprises a sequence having at least 65%, preferably at least 75%, more preferably at least 85%, still more preferably at least 90%, and most preferably at least 96% homologous to a sequence from approximately nucleotide 412 to and including nucleotide 477 of SEQ ID NO:3, or its complementary sequence. Preferably, the sequence encodes a histidine-rich region of an antigenic polypeptide, preferably an ECD.

In another aspect, the present invention relates to an isolated polypeptide comprising an amino acid sequence having homology to the amino acid sequence (SEQ ID NO:4), or a fragment thereof, encoded by or within DNA 164647, designated herein as LIV-1-164647. Preferably the homology is at least approximately 80% homology, more preferably at least approximately 90%, still more preferably at least approximately 95%, and most preferably at least approximately 97% homology. Preferably, a LIV-1-164647 amino acid sequence of the invention is an aqueous soluble ECD homologous to amino acid 1 to approximately amino acid 327 or a fragment thereof comprising at least 10 amino acids. The region of the ECD is readily determined from a standard hydropathy plot indicating the relatively more hydrophilic region N-terminal of a hydrophobic transmembrane region. In a related embodiment, the homologous amino acid sequence of the invention comprises a sequence from amino acid 126 to and including amino acid 132 of SEQ ID NO:4 (specifically, the amino acid sequence HDHHSHH (SEQ ID NO:17)), or a sequence from amino acid 743 to and including amino acid 755 of SEQ ID NO:4 (specifically, the amino acid sequence SIFEHKIVFRINF (SEQ ID NO:18), or both sequences. The present invention further includes an isolated polypeptide comprising an amino acid sequence having at least 50%, preferably at least 80%, more preferably at least 90% homologous to SEQ ID NO:17. The present invention still further includes an isolated polypeptide comprising an amino acid sequence having at least 20%, more preferably at least 50%, still more preferably at least 80%, and most preferably at least 90% homology to SEQ ID NO:18. In still another embodiment, the invention includes an isolated nucleic acid of SEQ ID NO:3 and an isolated polypeptide of SEQ ID NO:4. The present invention further includes an isolated polypeptide comprising an amino acid sequence having at least 65%, preferably at least 75%, more preferably at least 85%, still more preferably at least 90%, and most preferably at least 96% to a sequence from amino acid 114 to and including amino acid 135 of SEQ ID NO:4. The amino acid sequence from amino acid 114 to 135 is designated SEQ ID NO:19. A still further embodiment includes an isolated polypeptide comprising SEQ ID NO:17 and/or SEQ ID NO:18.

In still another embodiment, the invention includes an isolated polypeptide comprising an amino acid sequence wherein the sequence is at least 98% homologous to the sequence from amino acid 1 to and including amino acid 327 of SEQ ID NO:4, more preferably comprising the ECD of LIV-1-164647. Most preferably, the sequence comprises SEQ ID NO:17, forms a portion of an extracellular domain (ECD), preferably the ECD of LIV-1-164647. The term "portion" as used herein refers to a sequence that comprises at least 7 amino acids of the ECD of LIV-1-164647 from amino acid 1 to and including amino acid 327 of SEQ ID NO:4.

In another embodiment, the present invention concerns an antibody which specifically binds a LIV-1 polypeptide. Preferably, the antibody is a monoclonal antibody. More preferably, the antibody is a human antibody or a humanized antibody. In one embodiment, the antibody reduces activity of overexpressed LIV-1 polypeptide in a cell. In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a single-chain antibody, or an anti-idiotypic antibody. Preferably, a LIV-1-binding antibody of the invention binds specifically to a polypeptide having at least approximately 80% homology, more preferably at least approximately 90% homology, still more preferably at least approximately 95% homology, and most preferably at least approximately 97% homology to the LIV-1 ECD nucleic acid sequence, or a fragment thereof, encoded within the ECD coding region (nucleotides 1-1000) of DNA 164647 (SEQ ID NO:3). More preferably, a LIV-1-binding antibody of the invention binds specifically to a polypeptide having at least 80% homology, more preferably at least approximately 90% homology, still more preferably at least approximately 95% homology, and most preferably at least approximately 97% homology to the amino acid sequence of LIV-1 ECD (amino acids 1-327 of SEQ ID NO:4). In a preferred embodiment, the present invention concerns an isolated antibody which specifically binds a LIV-1 polypeptide encoded by a nucleic acid sequence comprising a nucleic acid sequence having at least 65%, preferably at least 75%, more preferably at least 85%, still more preferably at least 90%, and most preferably at least 96%, homology to a sequence from nucleotide 446 to and including nucleotide 463 of SEQ ID NO:3, or the nucleic acid sequence from 2297 to and including 2337 of SEQ ID NO:3, or both nucleic acid sequences. In another preferred embodiment, the present invention concerns an isolated antibody which specifically binds a LIV-1 polypeptide comprising the amino acid sequence having at least 65%, preferably at least 75%, more preferably at least 85%, still more preferably at least 90%, and most preferably at least 96% homology to a sequence from amino acid 126 to and including amino acid 132 of SEQ ID NO:4, or the amino acid sequence from amino acid 743 to and including amino acid 755 of SEQ ID NO:4, or both amino acid sequences.

In still another embodiment, the invention concerns an antibody, preferably a monoclonal antibody, that specifically binds the same epitope of LIV-1, preferably LIV-1-1164647, that is bound by any one of the monoclonal antibodies produced by the hybridoma cell lines deposited with the American Type Culture Collection (ATCC) as disclosed herein.

In a further embodiment, the invention includes an antibody that binds to a polypeptide comprising a sequence from amino acid 1 to and including amino acid 147 of SEQ ID NO:4. In another embodiment, the antibody binds a polypeptide comprising amino acid 148 to and including amino acid 298 of SEQ ID NO:4. Preferably, the antibodies are monoclonal antibodies. More preferably, the monoclonal antibodies are human antibodies or humanized antibodies.

In another aspect, the invention concerns a composition comprising an antibody which binds LIV-1 polypeptide in an admixture with a pharmaceutically acceptable carrier. In one aspect, the composition comprises a therapeutically effective amount of the antibody. In another aspect, the composition comprises a further active ingredient, which may, for example, be a further antibody or a cytotoxic or chemotherapeutic agent. Preferably, the composition is sterile.

In a further embodiment, the invention concerns a nucleic acid encoding an anti-LIV-1 antibody according to the invention, and vectors and recombinant host cells comprising such nucleic acid.

In a still further embodiment, the invention concerns a method for producing an anti-LIV-1 antibody by culturing a host cell transformed with nucleic acid encoding the antibody under conditions such that the antibody is expressed, and recovering the antibody from the cell culture.

The invention further concerns antagonists and agonists of a LIV-1 polypeptide, which antagonists inhibit one or more of the functions or activities of the LIV-1 polypeptide and which agonists mimic one or more of the functions or activities of the LIV-1 polypeptide. Preferably the LIV-1 polypeptide is the LIV-1-164647 polypeptide whose functions or activities are antagonized or agonized.

In another embodiment, the invention concerns a method for determining the presence of a LIV-1 polypeptide or fragment thereof comprising exposing a cell suspected of containing the LIV-1 polypeptide to an anti-LIV-1 antibody of the invention and determining binding of the antibody to the cell.

In yet another embodiment, the present invention concerns a method of diagnosing tumor in a mammal, comprising detecting the level of expression of a gene encoding a LIV-1 polypeptide in a test sample of tissue cells obtained from the mammal, and in a control sample of known normal tissue cells of the same cell type, wherein a higher expression level in the test sample indicates the presence of tumor in the mammal from which the test tissue cells were obtained.

In another embodiment, the present invention concerns a method of diagnosing tumor in a mammal, comprising contacting an anti-LIV-1 antibody with a test sample of tissue cells obtained from the mammal, and detecting the formation of a complex between the anti-LIV-1 antibody and the LIV-1 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art.

For the methods of diagnosing, the test sample is usually obtained from an individual suspected to have neoplastic cell growth or proliferation (e.g. cancerous cells).

In another embodiment, the invention involves a method of diagnosing breast tumor tissue as tissue that overexpresses LIV-1 protein and expresses normal levels of ErbB2. The method comprises providing a test sample of tissue suspected of being cancerous, contacting the test sample with an antibody to the naturally occurring form of the LIV-1 gene product, contacting the same or duplicate test sample with an anti-ErbB2 antibody, detecting the relative binding of the antibodies to the test sample compared to a control sample, where the control may be a positive control, a negative control, or both. A test sample that overexpresses LIV-1 gene product (relative to normal tissue), but does not overexpress ErbB2 protein (relative to normal tissue), is diagnosed as a member of the population of breast tumors to be treated by the compositions and methods of the invention. Useful in the diagnostic assay method of the invention are anti-ErbB2 antibodies that bind the extracellular domain of the ErbB2 receptor, and preferably bind to the epitope 4D5 or 3H4 within the ErbB2 extracellular domain sequence. Mole preferably, the antibody is the antibody 4D5. Other preferred ErbB2-binding antibodies include, but are not limited to, antibodies 7C2, 7F3, and 2C4. Information regarding anti-ErbB2 antibodies is found, for example, in Hudziak, R. M. et al. U.S. Pat. No. 5,772,997, incorporated herein by reference in its entirety.

In another aspect, the present invention concerns a cancer diagnostic kit, comprising an anti-LIV-1-164647 antibody and a carrier (e.g. a buffer) in suitable packaging. The kit preferably contains instructions for using the antibody to detect the LIV-1 polypeptide.

In yet another aspect, the invention concerns a method for inhibiting the growth of tumor cells comprising exposing a cell which overexpresses a LIV-1 polypeptide to an effective amount of an agent inhibiting the expression and/or activity of the LIV-1 polypeptide. The agent preferably is an anti-LIV-1-164647 antibody, a small organic and inorganic molecule, peptide, phosphopeptide, antisense or ribozyme molecule, or a triple helix molecule. In a specific aspect, the agent, e.g. anti-LIV-1-164647 antibody induces cell death, or at least slows cell growth sufficiently to allow other methods of cancer treatment to be administered. In a further aspect, the tumor cells are further exposed to radiation treatment and/or a cytotoxic or chemotherapeutic agent.

In yet another aspect, the invention concerns a method for the treatment of a human patient susceptible to or diagnosed with a disorder characterized by overexpression of LIV-1 gene product without overexpression of ErbB2 receptor. In an embodiment, the method comprises administering a therapeutically effective amount of an anti-LIV-1 polypeptide antibody, where administration may be intravenous, subcutaneous, or other pharmaceutically acceptable method of antibody delivery. Preferably the antibody specifically binds the naturally occurring form of the LIV-1-164647 polypeptide, wherein the binding is preferably to the extracellular domain or a fragment thereof. Preferably, the initial dose (or doses) as well as the subsequent maintenance dose or doses are administered subcutaneously. Optionally, where the patient's tolerance of the anti-LIV-1 antibody is unknown, the initial dose is administered by intravenous infusion, followed by subcutaneous administration of the maintenance doses it the patient's tolerance for the antibody is acceptable. According to the embodiment of the invention, the initial dose or doses is followed by subsequent doses of equal or smaller amounts of antibody at intervals sufficiently close to maintain the trough serum concentration of antibody at or above an efficacious target level. Preferably, an initial dose or individual subsequent dose does not exceed 100 mg/kg, and each subsequent dose is at least 1 µg/kg. The choice of delivery method for the initial and maintenance doses is made according to the ability of the animal or human patient to tolerate introduction of the antibody into the body. Where the antibody is well-tolerated, the time of infusion may be reduced. The choice of delivery method as disclosed for this embodiment applies to all drug delivery regimens contemplated according to the invention.

In a further aspect, the invention provides a method of treating LIV-1 gene product-overexpressing cancer (lacking overexpression of ErbB2) in a human patient comprising administering to the patient effective amounts of an anti-LIV-1 antibody (which antibody preferably binds the extracellular domain of LIV-1 gene product) and a chemotherapeutic agent. In one embodiment of the invention, the chemotherapeutic agent in a toxoid including, but not limited to, paclitaxel and doxetaxel. In another embodiment, the chemotherapeutic agent is an anthracyline derivative including, but not limited to, doxorubicin and epirubicin. In still another embodiment, the chemotherapeutic agent is not administered to the patient simultaneously with the anti-LIV-1 antibody. One or more additional chemotherapeutic agents may also be administered to the patient.

The disorder to be treated by a method of the invention preferably is a benign or malignant tumor characterized by the overexpression of the LIV-1 gene product. Preferably, the malignant cells of the tumor express approximately the same level of ErbB2 (or less) as a non-cancerous cell of the same type. For example, the disorder to be treated is a cancer, such as breast cancer, lung cancer, and prostate cancer.

Accordingly, one aspect of the invention involves compounds that bind to the LIV-1 protein and inhibit its activity. Preferably the compounds bind to the extracellular region of the LIV-1 protein and inhibit its activity. In an embodiment of the invention, the inhibiting compounds are antibodies specific to the LIV-1 gene product or fragments thereof. Preferably, the inhibiting compounds of the invention bind specifically to the extracellular region of the LIV-1 protein.

In another aspect, the invention involves compounds that block the binding of an activating ligand of LIV-1 protein. Such ligand-blocking compounds include, but are not limited to polypeptides, proteins, antibodies and the like. Preferably the ligand-blocking compounds specifically block the activity of a LIV-1 activating ligand. More preferably, the ligand-blocking compounds of the invention inhibit growth of a LIV-1-expressing cell.

In another aspect, the invention involves a method for identifying a compound capable of inhibiting the expression and/or activity of a LIV-1 polypeptide, comprising contacting a candidate compound with a LIV-1 polypeptide under conditions and for a time sufficient to allow these two components to interact. In a specific aspect, either the candidate compound or the LIV-1 polypeptide is immobilized on a solid support. In another aspect, the non-immobilized component carries a detectable label.

In yet another aspect, the invention concerns an article of manufacture, comprising a container; a composition within the container comprising an anti-LIV-1 antibody that binds the LIV-1 protein (preferably binding to the extracellular domain or a fragment thereof) or binds an activating ligand of the LIV-1 protein; and optionally a label on or associated with the container that indicates that the composition can be used for treating a condition characterized by overexpression of LIV-1 without overexpression of ErbB2. According to another embodiment of the invention, the article of manufacture further includes a package insert comprising instructions to administer the anti-LIV-1 antibody subcutaneously for at least one of the doses, preferably for all of the subsequent doses following the initial dose, most preferably for all doses.

Where the methods and compositions of the invention comprise an anti-LIV-1 antibody, which specifically and preferably binds the extracellular domain of a LIV-1 gene product, or a fragment of the extracellular domain. The compositions of the invention preferably include a humanized LIV-1 antibody. Thus, the invention further pertains to a composition comprising an antibody that specifically and preferably binds the extracellular domain of LIV-1 gene product, and pertains to the use of the antibody for treating LIV-1+/ErbB2-expressing cancer in a human, e.g., LIV-1 overexpressing cancer that does not coexpress high levels of ErbB2. Preferably the antibody is a monoclonal antibody, e.g., humanized anti-LIV-1 monoclonal antibody that binds to the extracellular domain (or a portion of the extracellular domain) of LIV-1 (hereinafter anti-LIV-1) The antibody may be an intact antibody (e.g., an intact $IgG_1$ antibody) or an antibody fragment (e.g., a Fab, $F(Ab)_2$, diabody, and the like). The variable light chain and variable heavy chain regions of humanized anti-LIV-1 antibody.

These and other advantages and features of the present invention will become apparent to those persons skilled in the art upon reading the details of the invention as more fully set forth below and in the appended claims.

BRIEF DESCRIPTION OF THE DRAWINGS

FIGS. 1A-1C are the nucleic acid sequence (SEQ ID NO:1 (coding sequence). FIGS. 1A-1 to 1A-2) and the amino acid sequence (SEQ ID NO:2, FIG. 1B) of the LIV-1 protein. The dashed overlined portion is predicted to be a signal sequence (approximately amino acids 1 to 20). The predicted extracellular domain of LIV-1 protein is that portion of the LIV-1 amino acid sequence underscored by a dashed line (approximately amino acids 24 to 312). The predicted transmembrane domain extends from approximately amino acid 318 to approximately amino acid 367. The approximate positions of the domains were predicted using a standard hydropathy analysis program. A nucleic acid sequence (SEQ ID NO:5) encoding a portion of LIV-1 and useful in microarray analysis is shown in FIG. 1C.

FIGS. 2A-2B are the nucleic acid sequence and amino acid sequence, respectively, corresponding to DNA 164647. FIGS. 2A1-2A5 is the nucleotide sequence of DNA 164647 that is a cDNA encoding a native sequence LIV-1 protein. SEQ ID NO:3 is the coding strand of DNA 164647. FIG. 2B is the derived amino acid sequence (SEQ ID NO:4) of a native LIV-1 polypeptide encoded by DNA 164647.

FIGS. 3A-1-3A-9 is an alignment of SEQ ID NO:1 and SEQ ID NO:3 nucleic acid sequences.

FIGS. 4-1-4-3 is an alignment of SEQ ID NO:2 and SEQ ID NO:4 amino acid sequences. The sequences differ in the ECD (near amino acid 130 of SEQ ID NO:4) and C-terminal region beyond about amino acid 740 of SEQ ID NO:4. A single amino acid difference was found at amino acid 651 of SEQ ID NO:4.

FIG. 5 is a flow chart illustrating the FLIP cloning method up to the restriction digestion selection step, as described herein. The shaded boxes flanking the vector sequence represent the target gene sequences.

FIG. 6 is a graphical representation of a fluorescent activated cell sorting (FACS) analysis in which an anti-LIV-1-164647 monoclonal antibody was shown to bind primarily to the surface of 3T3 cells transfected with DNA 164647. The term "pRK5" refers cells transfected with vector lacking a LIV-1-164647 insert. The term "pRK5-LIV-1-164647" refers to cells transfected with vector expressing full length LIV-1-164647.

FIG. 7 is a bar graph demonstrating that the LIV-1-164647 extracellular domain is expressed on the surface of cells transfected with DNA encoding the full-length LIV-1-164647 protein.

DESCRIPTION OF THE EMBODIMENTS

1. Definitions

As used herein, the term "LIV-1" refers to a gene or its encoded protein, which gene transcript is detected in above normal levels in some cancer cells. More specifically, a LIV-1 gene or protein of the present invention is one which is encoded by DNA 164647 (SEQ ID NO:3) and has the deduced amino acid sequence of SEQ ID NO:4. As used herein, the term LIV-1 refers to LIV-1-164647 where the disclosure refers to a nucleic acid comprising at least 21 nucleotides of SEQ ID NO:3, or where the disclosure refers to an amino acid sequence comprising at least 7 amino acids of SEQ ID NO:4 as disclosed herein. According to the invention. LIV-1-164647 is expressed in higher than normal amounts in a cell, while the gene encoding ErbB2 receptor is not expressed in higher than normal amounts. Such higher than normal expression is termed "overexpression" of a gene or protein. The term "LIV-1" or "LIV-1-164647" may be used to refer to a LIV-1 gene or its encoded protein. Generally, where a protein or peptide is contemplated, the term "LIV-1 protein" will be used.

The term "LIV-1 gene product" or "LIV-1 protein" refers to the expressed protein product of the gene, preferably a polypeptide or protein form of the gene product. According to the invention, a polypeptide or protein form of the LIV-1 gene product includes a soluble form of the gene product (i.e. the extracellular domain (ECD) of the LIV-1 gone product), which soluble form is useful as an antigen for raising anti-LIV-1 gene product antibodies that bind the extracellular domain of full length LIV-1 gene product and inhibit its activation. It is understood that LIV-1 gene product may also refer to the messenger RNA (mRNA) gene product and, where appropriate, the distinction between protein and mRNA is made. A LIV-1 protein according to the invention is encoded by a nucleic acid of the invention comprising a sequence at least 80% homologous to the DNA 164647 (SEQ ID NO:3 or its complement; FIG. 2A), preferably at least approximately 90% homologous, more preferably at least approximately 95%, and most preferably at least approximately 97% homologous to SEQ ID NO:3 or its complement), or a portion thereof. A LIV-1 nucleic acid of the invention hybridizes under stringent conditions to SEQ ID NO:3 or its complement) or a portion thereof. A LIV-1 protein of the invention is at least 80% homologous to the amino acid sequence encoded by DNA 164647 (LIV-1 polypeptide SEQ ID NO:4; FIG. 2B), preferably at least approximately 90% homologous, more preferably at least approximately 95%, and most preferably at least approximately 97% homologous to SEQ ID NO:4, or a fragment thereof.

The terms "anti-LIV-1 antibody," "LIV-1 antibody," and grammatically analogous terms refer to an antibody which binds specifically to at least a portion of the extracellular domain of the LIV-1-164647 protein having a predicted amino acid sequence of SEQ ID NO:4 (the predicted full length amino acid sequence of LIV-1-164647 gene). Preferably, the antibody binds to the extracellular domain of LIV-1 gene product, more preferably binding to the same epitope as epitopes A, B, or C to which the monoclonal antibodies disclosed herein bind. Even more preferably, the anti-LIV-1-164647 antibody binds to a polypeptide having at least 65% homology to a sequence from amino acid 114 to and including amino acid 135 of SEQ ID NO:4. Preferably, an anti-LIV-1 antibody of the invention is human or humanized when the antibody is to be used to treat a human patient.

The antibody of the invention is preferably one which binds specifically to human LIV-1-164647, meaning that it does not significantly cross-react with other proteins. In such embodiments, the extent of binding of the antibody to proteins other than LIV-1 gene product will be less than about 10% as determined by fluorescence activated cell sorting (FACS) analysis or radioimmunoprecipitation (RIA).

The term "antibody" is used in the broadest sense and specifically covers, for example, single anti-LIV-1 monoclonal antibodies (including agonist, antagonist, and neutralizing antibodies), anti-LIV-1 antibody compositions with polyepitopic specificity, single chain anti-LIV-1 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kiln are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aliened with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a -sheet configuration, connected by three CDRs, which form loops connecting, and in some cases forming part of, the -sheet structure. The CDRs in each chain are held together in close proximity by the FR regions and, with the CDRs from the other chain, contribute to the formation of the antigen-binding site of antibodies (see Kabat et al. NIH Publ. No.91-3242, Vol. 1 pages 647-669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" to "CDR" (i.e., residues in the light chain variable domain and residues in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e., residues in the light chain variable domain and residues in the heavy chain variable domain; Clothia and specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g. U.S. Pat. No. 4,816,567). The monoclonal antibodies may also be isolated from phage antibody libraries using the techniques described in Clackson et al., *Nature*, 352:624-628 [1991] and Marks et al., *J. Mol. Biol.* 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA.* 81:6851-6855 [1984]). Chimeric antibodies of interest herein include human constant region sequences together with antigen bindings regions of rodent (e.g. murine) origin, or "primatized" antibodies comprising variable domain antigen-binding sequences derived from a non-human primate (e.g. Old World Monkey, Ape, macaque, etc.), or antigen binding regions derived from antibodies generated in other non-human species that have been immunized with the antigen of interest.

"Humanized" forms of non-human (e.g., rodent) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat or rabbit having the desired specificity, affinity, and capacity. In some instances, framework region (FR) residues of the human immunoglobulin are replaced by corresponding non-human residues. Furthermore, humanized antibodies may comprise residues which are found neither in the recipient antibody nor in the donor antibody. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see, Jones et al., *Nature*, 311:522-525 (1986); Reichmann et al., *Nature*, 332:323-329 [1988]; and Presta, *Curr. Op. Struct. Biol.* 2:593-596 (1992).

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenhurg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA.* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% (by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "overexpression," as used herein refers to overexpression of a gene and/or its encoded protein in a cell, such as a cancer cell. A cancer cell that "overexpresses" a protein is one that has significantly higher levels of that protein compared to a noncancerous cell of the same tissue type. For example, according to the present invention, the overexpression of a protein LIV-1 protein may be caused by gene amplification or by increased transcription or translation.

Overexpression of a LIV-1 protein may be determined in a diagnostic or prognostic assay by evaluating increased levels of a LIV-1 mRNA in a cell or tissue (e.g. via a quantitative PCR method) or by detecting a LIV-1 protein present on the surface of a cell (e.g. via an immunohistochemistry assay). Alternatively, or additionally, one may measure levels of LIV-1-encoding nucleic acid in the cell, e.g. via fluorescent in situ hybridization (FISH; see WO98/45479 published October, 1998), southern blotting, or polymerase chain reaction (PCR) techniques, such as real time quantitative PCR (RT-PCR). One may also study LIV-1 overexpression by measuring shed antigen (e.g., LIV-1 extracellular domain) in a biological fluid such as serum by contacting the fluid or other sample with an antibody that binds to a LIV-1 protein or fragment thereof. Various in vitro and in vivo assays are available to the skilled practitioner. For example, one may expose a fluid or tissue comprising a LIV-1 protein or fragment thereof, or cells within the body of the patient to an antibody which is optionally labeled with a detectable label, e.g. a radioactive isotope, and binding of the antibody to cells in a sample or the patient can be evaluated for overexpression, e.g. by external scanning for radioactivity or by analyzing a biopsy taken from a patient previously exposed to the antibody.

A cell that "overexpresses" LIV-1 has significantly higher than normal LIV-1 nucleic acid levels compared to a noncancerous cell of the same tissue type. Typically, the cell is a cancer cell, e.g. a breast, ovarian, prostate, stomach, endometrial, salivary gland, lung, kidney, colon, thyroid, pancreatic or bladder cell. The cell may also be a cell line such as SKBR3, BT474, Calu 3, MDA-MB-453, MDA-MB-361 or SKOV3.

Conversely, a cancer that is "not characterized by overexpression of a LIV-1 protein or a LIV-1 gene is one which, in a diagnostic assay, does not express higher than normal levels of LIV-1 gene or LIV-1 protein compared to a noncancerous cell of the same tissue type.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include highest cancer, prostate cancer, colon cancer, squamous cell cancer, small-cell lunge cancer, non-small cell lunar cancer, gastrointestinal cancer, pancreatic cancer, glioblastoma cervical cancer, ovarian cancer, liver cancer, bladder cancer, hepatoma, colorectal cancer, endometrial carcinoma, salivary gland carcinoma kidney cancer, liver cancer, vulval cancer, thyroid cancer, hepatic carcinoma and various types of head and neck cancer.

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

"Tumor", as used herein, refers to all neoplastic cell growth and proliferation, whether malignant or benign, and all pre-cancerous and cancerous cells and tissues.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, cattle, pigs, sheep, etc. Preferably, the mammal is human.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids, antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming, counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhône-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest GI also spill over into S-phase arrest, for example. DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al., (WB Saunders; Philadelphia, 1995), especially p. 13.

"Doxorubicin" is an athracycline antibiotic. The full chemical name of doxorubicin is (85-cis)-10-[(3-amino-2, 3,6-trideoxy-α-L-lyxo-hexopyranosyl)oxy]-7,8,9,10-tetrahydro-6,8,11-trihydroxy-8-(hydroxyacetyl)-1-methoxy-5, 12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL9, IL11, IL12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery." Directed *Drug Delivery*, Borchardt et al., (ed.), pp. 247-267. Humana Press (1985). The prodrugs of this invention include, but are not limited to, phosphate-containing prodrugs, thiophosphate-containing prodrugs, sulfate-containing prodrugs, peptide-containing prodrugs. D-amino acid-modified prodrugs, glycosylated prodrugs, β-lactam-containing prodrugs, optionally substituted phenoxyacetamide-containing prodrugs or optionally substituted phenylacetamide-containing prodrugs. 5-fluorocytosing and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "effective amount" of a polypeptide disclosed herein or an antagonist thereof, in reference to inhibition of neoplastic cell growth, tumor growth or cancer cell growth, is an amount capable of inhibiting to some extent, the growth of target cells. The term includes an amount capable of invoking a growth inhibitory, cytostatic and/or cytotoxic effect and/or apoptosis of the target cells. An "effective amount" of a LIV-1 polypeptide antagonist for purposes of inhibiting neoplastic cell growth, tumor growth or cancer cell (growth, may be determined empirically and in a routine manner.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a LIV-1 polypeptide antagonist for purposes of treatment of tumor may be determined empirically and in a routine manner.

A "growth inhibitory amount" of a LIV-1 antagonist is an amount capable of inhibiting the growth of a cell, especially tumor, e.g., cancer cell, either in vitro or in vivo. A "growth inhibitory amount" of a LIV-1 antagonist for purposes of inhibiting neoplastic cell growth may be determined empirically and in a routine manner.

A "cytotoxic amount" of a LIV-1 antagonist is an amount capable of causing the destruction of a cell, especially tumor, e.g., cancer cell, either in vitro or in vivo. A "cytotoxic amount" of a LIV-1 antagonist for purposes of inhibiting neoplastic cell growth may be determined empirically and in a routine manner.

"Percent (%) amino acid sequence homology or identity" with respect to the LIV-1 polypeptide sequences identified herein is defined as the percentage of amino acid residues in a candidate sequence that are identical with the amino acid residues in a LIV-1 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program was authored by Genentech, Inc., and the source code shown in FIGS. 20A-Q has been filed with user documentation in the U.S. Copyright Office, Washington D.C., 20559, where it is registered under U.S. Copyright Registration No. TXU510087, and is provided in Table 1. The ALIGN-2 program is publicly available through Genentech, Inc. South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence homology or identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.*, 25:3389-3402 (1997)). The NCBI-BLAST2 sequence comparison program may be downloaded from (www.)ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In addition, % amino acid sequence identity may also be determined using the WU-BLAST-2 computer program (Altschul et al., *Methods in Enzymology*, 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % amino acid sequence identity value is determined by dividing (a) the number of matching identical amino acids residues between the amino acid sequence of the LIV-1 polypeptide of interest having a sequence derived from the native LIV-1 polypeptide encoded by DNA 164647 and the comparison amino acid sequence of interest (i.e., the sequence against which the LIV-1 polypeptide of interest is being compared which may be a LIV-1 variant polypeptide) as determined by WU BLAST-2 by (b) the total number of amino acid residues of the LIV-1 polypeptide of interest. For example, in the statement "a polypeptide comprising an amino acid sequence A which has or having at least 80% amino acid sequence identity to the amino acid sequence B", the amino acid sequence A is the comparison amino acid sequence of interest and the amino acid sequence B is the amino acid sequence of the LIV-1 polypeptide of interest.

"Percent (%) nucleic acid sequence homology or identity" with respect to the LIV-1 polypeptide-encoding nucleic acid sequences identified herein is defined as the percentage of nucleotides in a candidate sequence that are identical with the nucleotides in a LIV-1 polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2, wherein the complete source code for the ALIGN-2 program is has been filed with user documentation in the U.S. Copyright Office, Washington D.C., 20559, where it is registered under U.S. Copyright Registration No. TXU510087 and is provided herein in Table 1 as source code. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary

Table 1

```
/*
 *
 * C-C increased from 12 to 15
 * Z is average of EQ
 * B is average of ND
 * match with stop is _M; stop-stop = 0; J (joker) match = 0
 */
define _M    -8       /* value of a match with a stop */ int    _day[26][26] = {
/*     A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3,-4, 3, 2,-5, 0, 1,-2, 0, 0,-3,-2, 2,_M,-1, 1, 0, 0, 0, 0,-2,-5, 0,-3, 1},
/* C */ {-2,-4,15,-5,-5,-4,-3,-3,-2, 0,-5,-6,-5,-4,_M,-3,-5,-4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0,-4, 2},
/* E */ { 0, 2,-5, 3, 4,-5, 0, 1,-2, 0, 0,-3,-2, 1,_M,-1, 2,-1, 0, 0, 0,-2,-7, 0,-4, 3},
/* F */ {-4,-5,-4,-6,-5, 9,-5,-2, 1, 0,-5, 2, 0,-4,_M,-5,-5,-4,-3,-3, 0,-1, 0, 0, 7,-5},
/* G */ { 1, 0,-3, 1, 0,-5, 5,-2,-3, 0,-2,-4,-3, 0,_M,-1,-1,-3, 1, 0, 0,-1,-7, 0,-5, 0},
/* H */ {-1, 1,-3, 1, 1,-2,-2, 6,-2, 0, 0,-2,-2, 2,_M, 0, 3, 2,-1,-1, 0,-2,-3, 0, 0, 2},
/* I */ {-1,-2,-2,-2,-2, 1,-3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0,-4, 0},
/* L */ {-2,-3,-6,-4,-3, 2,-4,-2, 2, 0,-3, 6, 4,-3,_M,-3,-2,-3,-3,-1, 0, 2,-2, 0,-1,-2},
/* M */ {-1,-2,-5,-3,-2, 0,-3,-2, 2, 0, 0, 4, 6,-2,_M,-2,-1, 0,-2,-1, 0, 2,-4, 0,-2,-1},
/* N */ { 0, 2,-4, 2, 1,-4, 0, 2,-2, 0, 1,-3,-2, 2,_M,-1, 1, 0, 1, 0, 0,-2,-4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0,-1,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0,-4,-1,-1,-4,-3, 2,-2, 0, 3,-3, 0, 0,_M, 0, 1, 6, 0,-1, 0,-2, 2, 0,-4, 0},
/* S */ { 1, 0, 0, 0, 0,-3, 1,-1,-1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2,-4,-4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0,-4,-4, 7,-5, 0,-1, 0,-4, 1, 2,-2,_M,-5,-4,-4,-3,-3, 0,-2, 0, 0,10,-4},
/* Z */ { 0, 1,-5, 2, 3,-5, 0, 2,-2, 0, 0,-2,-1, 1,_M, 0, 3, 0, 0, 0, 0,-2,-6, 0,-4, 4}
};
```

Page 1 of day.h

```
/*
 */
#include <stdio.h>
include <ctype.h> define  MAXJMP   16      /* max jumps in a diag */
define  MAXGAP   24      /* don't continue to penalize gaps larger than this */
#define  JMPS     1024    /* max jmps in an path */
define  MX       4       /* save if there's at least MX-1 bases since last jmp */ define  DMAT     3       /* value of matching bases */
define  DMIS     0       /* penalty for mismatched bases */
#define  DINS0    8       /* penalty for a gap */
#define  DINS1    1       /* penalty per base */
#define  PINS0    8       /* penalty for a gap */
#define  PINS1    4       /* penalty per residue */
```

```c
struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char    *ofile;                 /* output file name */
char    *namex[2];              /* seq names: getseqs() */
char    *prog;                  /* prog name for err msgs */
char    *seqx[2];               /* seqs: getseqs() */
int     dmax;                   /* best diag: nw() */
int     dmax0;                  /* final diag */
int     dna;                    /* set if dna: main() */
int     endgaps;                /* set if penalizing end gaps */
int     gapx, gapy;             /* total gaps in seqs */
int     len0, len1;             /* seq lens */
int     ngapx, ngapy;           /* total size of gaps */
int     smax;                   /* max score: nw() */
int     *xbm;                   /* bitmap for matching */
long    offset;                 /* current offset in jmp file */
struct  diag    *dx;            /* holds diagonals */
struct  path    pp[2];          /* holds path for seqs */ char    *calloc(), *malloc(), *index(), *strcpy();
char    *getseq(), *g_calloc();
```

Page 1 of nw.h

```c
/* Needleman-Wunsch alignment program
 *
 * usage: progs file1 file2
 * where file1 and file2 are two dna or two protein sequences.
 * The sequences can be in upper- or lower-case an may contain ambiguity
 * Any lines beginning with ';', '>' or '<' are ignored
 * Max file length is 65535 (limited by unsigned short x in the jmp struct)
 * A sequence with 1/3 or more of its elements ACGTU is assumed to be DNA
 * Output is in the file "align.out"
 *
 * The program may create a tmp file in /tmp to hold info about traceback.
 * Original version developed under BSD 4.3 on a vax 8650
 */
include "nw.h"
#include "day.h"
```

```
static     _dbval[26] = {
           1,14,2,13,0,0,4,11,0,0,12,0,3,15,0,0,0,5,6,8,8,7,9,0,10,0
};

static     _pbval[26] = {
           1, 2|(1<<('D'-'A'))|(1<<('N'-'A')), 4, 8, 16, 32, 64,
           128, 256, 0xFFFFFFF, 1<<10, 1<<11, 1<<12, 1<<13, 1<<14,
           1<<15, 1<<16, 1<<17, 1<<18, 1<<19, 1<<20, 1<<21, 1<<22,
           1<<23, 1<<24, 1<<25|(1<<('E'-'A'))|(1<<('Q'-'A'))
};

main(ac, av)
           int     ac;
           char    *av[];
{
           prog = av[0];
           if (ac != 3) {
                   fprintf(stderr,"usage: %s file1 file2\n", prog);
                   fprintf(stderr,"where file1 and file2 are two dna or two protein sequences.\n");
                   fprintf(stderr,"The sequences can be in upper- or lower-case\n");
                   fprintf(stderr,"Any lines beginning with ';' or '<' are ignored\n");
                   fprintf(stderr,"Output is in the file \"align.out\"\n");
                   exit(1);
           }
           namex[0] = av[1];
           namex[1] = av[2];
           seqx[0] = getseq(namex[0], &len0);
           seqx[1] = getseq(namex[1], &len1);
           xbm = (dna)? _dbval : _pbval;

endgaps = 0;                /* 1 to penalize endgaps */
           ofile = "align.out";        /* output file */ nw();                       /* fill in the matrix, get the possible jmps */
           readjmps();                 /* get the actual jmps */
           print();                    /* print stats, alignment */ cleanup(0);                 /* unlink any tmp files */
}
```

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
{
           char    *px, *py;           /* seqs and ptrs */
           int     *ndely, *dely;      /* keep track of dely */
           int     ndelx, delx;        /* keep track of delx */
           int     *tmp;               /* for swapping row0, row1 */
           int     mis;                /* score for each type */
           int     ins0, ins1;         /* insertion penalties */
```

```
register        id;             /* diagonal index */
register        ij;             /* jmp index */
register        *col0, *col1;   /* score for curr, last row */
register        xx, yy;         /* index into seqs */ dx = (struct diag *)g_calloc("to get diags", len0+len1+1, sizeof(struct diag));

ndely = (int *)g_calloc("to get ndely", len1+1, sizeof(int));
dely = (int *)g_calloc("to get dely", len1+1, sizeof(int));
col0 = (int *)g_calloc("to get col0", len1+1, sizeof(int));
col1 = (int *)g_calloc("to get col1", len1+1, sizeof(int));
ins0 = (dna)? DINS0 : PINS0;
ins1 = (dna)? DINS1 : PINS1;

smax = -10000;
if (endgaps) {
        for (col0[0] = dely[0] = -ins0, yy = 1; yy <= len1; yy++) {
                col0[yy] = dely[yy] = col0[yy-1] - ins1;
                ndely[yy] = yy;
        }
        col0[0] = 0;    /* Waterman Bull Math Biol 84 */
}
else
        for (yy = 1; yy <= len1; yy++)
                dely[yy] = -ins0;

/* fill in match matrix
 */
for (px = seqx[0], xx = 1; xx <= len0; px++, xx++) {
        /* initialize first entry in col
         */
        if (endgaps) {
                if (xx == 1)
                        col1[0] = delx = -(ins0+ins1);
                else
                        col1[0] = delx = col0[0] - ins1;
                ndelx = xx;
        }
        else {
                col1[0] = 0;
                delx = -ins0;
                ndelx = 0;
        }
```

Page 2 of nw.c

...nw

```
        for (py = seqx[1], yy = 1; yy <= len1; py++, yy++) {
                mis = col0[yy-1];
                if (dna)
                        mis += (xbm[*px-'A']&xbm[*py-'A'])? DMAT : DMIS;
                else
                        mis += _day[*px-'A'][*py-'A'];

/* update penalty for del in x seq;
                 * favor new del over ongong del
                 * ignore MAXGAP if weighting endgaps
                 */
                if (endgaps || ndely[yy] < MAXGAP) {
```

```
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Page 3 of nw.c
...nw

```
        id = xx - yy + len1 - 1;
        if (mis >= delx && mis >= dely[yy])
                col1[yy] = mis;
        else if (delx >= dely[yy]) {
                col1[yy] = delx;
                ij = dx[id].ijmp;
                if (dx[id].jp.n[0] && (!dna || (ndelx >= MAXJMP
                    && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = ndelx;
                dx[id].jp.x[ij] = xx;
                dx[id].score = delx;
        }
```

```
                else {
                        col1[yy] = dely[yy];
                        ij = dx[id].ijmp;

if (dx[id].jp.n[0] && (!dna || (ndely[yy] >= MAXJMP
                                && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = -ndely[yy];
                        dx[id].jp.x[ij] = xx;
                        dx[id].score = dely[yy];
                }
                if (xx == len0 && yy < len1) {
                        /* last col
                        */
                        if (endgaps)
                                col1[yy] -= ins0+ins1*(len1-yy);
                        if (col1[yy] > smax) {
                                smax = col1[yy];
                                dmax = id;
                        }
                }
        }
        if (endgaps && xx < len0)
                col1[yy-1] -= ins0+ins1*(len0-xx);
        if (col1[yy-1] > smax) {
                smax = col1[yy-1];
                dmax = id;
        }
        tmp = col0; col0 = col1; col1 = tmp;
  }
  (void) free((char *)ndely);
  (void) free((char *)dely);
  (void) free((char *)col0);
  (void) free((char *)col1);
}
```

/*
*
* print() -- only routine visible outside this module
*
* static:
* getmat() -- trace back best path, count matches: print()
* pr_align() -- print alignment of described in array p[]: print()
* dumpblock() -- dump a block of lines with numbers, stars: pr_align()
* nums() -- put out a number line: dumpblock()
* putline() -- put out a line (name, [num], seq, [num]): dumpblock()
* stars() -- put a line of stars: dumpblock()
* stripname() -- strip any path and prefix from a seqname
*/ include "nw.h"

```
#define SPC       3
#define P_LINE    256     /* maximum output line */
define P_SPC     3       /* space between name or num and seq */ extern    _day[26][26];
int       olen;           /* set output line length */
FILE      *fx;            /* output file */ print()
{
          int     lx, ly, firstgap, lastgap;    /* overlap */ if ((fx = fopen(ofile, "w")) == 0) {
                    fprintf(stderr,"%s: can't write %s\n", prog, ofile);
                    cleanup(1);
          }
          fprintf(fx, "<first sequence: %s (length = %d)\n", namex[0], len0);
          fprintf(fx, "<second sequence: %s (length = %d)\n", namex[1], len1);
          olen = 60;
          lx = len0;
          ly = len1;
          firstgap = lastgap = 0;
          if (dmax < len1 - 1) {            /* leading gap in x */
                    pp[0].spc = firstgap = len1 - dmax - 1;
                    ly -= pp[0].spc;
          }
          else if (dmax > len1 - 1) {       /* leading gap in y */
                    pp[1].spc = firstgap = dmax - (len1 - 1);
                    lx -= pp[1].spc;
          }
          if (dmax0 < len0 - 1) {           /* trailing gap in x */
                    lastgap = len0 - dmax0 - 1;
                    lx -= lastgap;
          }
          else if (dmax0 > len0 - 1) {      /* trailing gap in y */
                    lastgap = dmax0 - (len0 - 1);
                    ly -= lastgap;
          }
          getmat(lx, ly, firstgap, lastgap);
          pr_align();
}
``` print

Page 1 of nwprint.c

```
/*
* trace back the best path, count matches
*/
static
getmat(lx, ly, firstgap, lastgap)
          int     lx, ly;                   /* "core" (minus endgaps) */
          int     firstgap, lastgap;        /* leading trailing overlap */
{
          int           nm, i0, i1, siz0, siz1;
          char          outx[32];
          double        pct;
          register      n0, n1;
          register char *p0, *p1;
``` getmat

```
/* get total matches, score
 */
i0 = i1 = siz0 = siz1 = 0;
p0 = seqx[0] + pp[1].spc;
p1 = seqx[1] + pp[0].spc;
n0 = pp[1].spc + 1;
n1 = pp[0].spc + 1;

nm = 0;
while ( *p0 && *p1 ) {
        if (siz0) {
                p1++;
                n1++;
                siz0--;
        }
        else if (siz1) {
                p0++;
                n0++;
                siz1--;
        }
        else {
                if (xbm[*p0-'A']&xbm[*p1-'A'])
                        nm++;
                if (n0++ == pp[0].x[i0])
                        siz0 = pp[0].n[i0++];
                if (n1++ == pp[1].x[i1])
                        siz1 = pp[1].n[i1++];
                p0++;
                p1++;
        }
}

/* pct homology:
 * if penalizing endgaps, base is the shorter seq
 * else, knock off overhangs and take shorter core
 */
if (endgaps)
        lx = (len0 < len1)? len0 : len1;
else
        lx = (lx < ly)? lx : ly;
pct = 100.*(double)nm/(double)lx;
fprintf(fx, "\n");
fprintf(fx, "<%d match%s in an overlap of %d: %.2f percent similarity\n",
        nm, (nm == 1)? "" : "es", lx, pct);
```

Page 2 of nwprint.c

```
fprintf(fx, "<gaps in first sequence: %d", gapx);
if (gapx) {
        (void) sprintf(outx, " (%d %s%s)",
                ngapx, (dna)? "base":"residue", (ngapx == 1)? "":"s");
        fprintf(fx,"%s", outx);
} fprintf(fx, ", gaps in second sequence: %d", gapy);
if (gapy) {
```

...getmat

```
                (void) sprintf(outx, " (%d %s%s)",
                        ngapy, (dna)? "base":"residue", (ngapy == 1)? "","s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized, left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
* print alignment of described in struct path pp[]
*/
static
pr_align()                                                                      pr_align
{
        int             nn;     /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];
        }
```

...pr_align

```
for (nn = nm = 0, more = 1; more; ) {
        for (i = more = 0; i < 2; i++) {
                /*
                 * do we have more of this sequence?
                 */
                if (!*ps[i])
                        continue;

more++;

if (pp[i].spc) {        /* leading space */
                        *po[i]++ = ' ';
                        pp[i].spc--;
                }
                else if (siz[i]) {      /* in a gap */
                        *po[i]++ = '-';
                        siz[i]--;
                }
                else {                  /* we're putting a seq element
                                         */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}
/*
 * dump a block of lines, including numbers, stars: pr_align()
 */
static
dumpblock()
{
        register i;
``` dumpblock

```
        for (i = 0; i < 2; i++)
                *po[i]-- = '\0';

(void) putc('\n', fx);
        for (i = 0; i < 2; i++) {
                if (*out[i] && (*out[i] != ' ' || *(po[i]) != ' '))
                        if (i == 0)
                                nums(i);
                        if (i == 0 && *out[1])
                                stars();
                        putline(i);
                        if (i == 0 && *out[1])
                                fprintf(fx, star);
                        if (i == 1)
                                nums(i);
                }
        }
}

/*
 * put out a number line: dumpblock()
 */
static
nums(ix)
        int       ix;       /* index in out[] holding seq line */
{
        char      nline[P_LINE];
        register  i, j;
        register char *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
```

Page 4 of nwprint.c

...dumpblock nums

```
/*
 * put out a line (name. [num]. seq. [num]): dumpblock()
 */
static
putline(ix)
        int     ix;
{
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) {
                        if (xbm[*p0-'A']&xbm[*p1-'A'])
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
``` putline

Page 5 of nwprint.c

...putline stars

```
        }
        *px++ = '\n';
        *px = '\0';
}
```

Page 6 of nwprint.c

```
/*
 * strip path or prefix from pn, return len: pr_align()
 */
static
stripname(pn)                                                                    stripname
        char    *pn;    /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
```

Page 7 of nwprint.c

```
/*
 * cleanup()   -- cleanup any tmp file
 * getseq()    -- read in seq, set dna, len, maxlen
 * g_calloc()  -- calloc() with error checkin
 * readjmps()  -- get the good jmps, from tmp file if necessary
 * writejmps() -- write a filled array of jmps to a tmp file: nw()
 */
include "nw.h"
include <sys/file.h> char    *jname = "/tmp/homgXXXXXX";             /* tmp file for jmps */
FILE    *fj;

int     cleanup();                              /* cleanup tmp file */
long    lseek();

/*
 * remove any tmp file if we blow
 */
cleanup(i)                                                                       cleanup
        int     i;
{
        if (fj)
                (void) unlink(jname);
        exit(i);
```

}
```
/*
 * read, return ptr to seq, set dna, len, maxlen
 * skip lines starting with ';', '<', or '>'
 * seq in upper or lower case
 */
char    *
getseq(file, len)                                                           getseq
        char        *file;      /* file name */
        int         *len;       /* seq len */
{
        char            line[1024], *pseq;
        register char   *px, *py;
        int             natgc, tlen;
        FILE            *fp;

if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc() failed to get %d bytes for %s\n", prog, tlen+6, file);
                exit(1);
        }
        pseq[0] = pseq[1] = pseq[2] = pseq[3] = '\0';
```

Page 1 of nwsubr.c

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++){
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
```

```
                dna = natgc > (tlen/3);
                return(pseq+4);
} char    *
g_calloc(msg, nx, sz)                                                                          g_calloc
        char    *msg;           /* program, calling routine */
        int     nx, sz;         /* number and size of elements */
{
        char            *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
 * get final jmps from dx[] or tmp file, set pp[], reset dmax: main()
 */
readjmps()                                                                                     readjmps
{
        int             fd = -1;
        int             siz, i0, i1;
        register        i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

Page 2 of nwsubr.c

...readjmps
```
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
```

```
                    xx = dx[dmax].jp.x[j];
                    dmax += siz;
                    if (siz < 0) {              /* gap in second seq */
                            pp[1].n[i1] = -siz;
                            xx += siz;

/* id = xx - yy + len1 - 1
                             */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {    /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }
    /* reverse the order of jmps
     */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd >= 0)
            (void) close(fd);
    if (fj) {
            (void) unlink(jname);
            fj = 0;
            offset = 0;
    }
}
```

Page 3 of nwsubr.c

```
/*
 * write a filled jmp struct offset of the prev one (if any); nw()
 */
writejmps(ix)                                                                           writejmps
        int     ix;
{
        char    *mktemp();

if (!fj) {
                if (mktemp(jname) < 0) {
                        fprintf(stderr, "%s: can't mktemp() %s\n", prog, jname);
```

```
                cleanup(1);
        }
        if ((fj = fopen(jname, "w")) == 0) {
                fprintf(stderr, "%s: can't write %s\n", prog, jname);
                exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

Page 4 of nwsubr.c

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.*, 25:3389-3402 (1997)). The NCBI-BLAST2 sequence comparison program may be downloaded from (www.) ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In addition, % nucleic acid sequence identity values may also be generated using the WU-BLAST-2 computer program (Altschul et al., *Methods in Enzymology*, 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. For purposes herein, a % nucleic acid sequence identity value is determined by dividing (a) the number of matching identical nucleotides between the nucleic acid sequence of the LIV-1 polypeptide-encoding nucleic acid molecule of interest having a sequence derived from the native sequence LIV-1 polypeptide-encoding nucleic acid and the comparison nucleic acid molecule of interest (i.e., the sequence against which the LIV-1 polypeptide-encoding nucleic acid molecule of interest is being compared which may be a variant LIV-1 polynucleotide) as determined by WU-BLAST-2 by (b) the total number of nucleotides of the LIV-1 polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the LIV-1 polypeptide-encoding nucleic acid molecule of interest.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution (as defined in Table 2 below) of the amino acid residue of interest.

TABLE 2

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln: his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine: ile: val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed)

mutagenesis, alanine scanning, and PCR mutagenesis. Site-directed mutagenesis [Carter et al., *Nucl. Acids Res.,* 13:4331 (1986), Zoller et al., *Nucl. Acids Res.* 10:6487 (1987)], cassette mutagenesis [Wells et al., *Gene.* 34:315 (1985)], restriction selection mutagenesis [Wells et al., *Philos. Trans. R. Soc. London SerA,* 317:415 (1986)] or other known techniques can be performed.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

"Isolated." when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the LIV-1 natural environment will not be present. Ordinarily, however, isolated polypeptide will be prepared by at least one purification step.

An "isolated" nucleic acid molecule encoding a LIV-1 polypeptide or an "isolated" nucleic acid encoding an anti-LIV-1 antibody, is a nucleic acid molecule that is identified and separated from at least one contaminant nucleic acid molecule with which it is ordinarily associated in the natural source of the LIV-1-encoding nucleic acid or the anti-LIV-1-encoding nucleic acid. Preferably, the isolated nucleic acid is free of association with all components with which it is naturally associated. An isolated LIV-1-encoding nucleic acid molecule or an anti-LIV-1-encoding nucleic acid molecule is other than in the form or setting in which it is found in nature.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology,* Wiley Interscience Publishers. (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate). 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual,* New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 35-50° C. The skilled artisan will recognize how to adjust the temperature, ionic strength, etc. as necessary to accommodate factors such as probe length and the like.

"Active" or "activity" for the purposes herein refers to form(s) of LIV-1 polypeptides which retain a biological and/or an immunological activity/property of a native or naturally-occurring LIV-1 polypeptide, wherein "biological" activity refers to a function (either inhibitory or stimulatory)

caused by a native or naturally-occurring LIV-1 polypeptide other than the ability to induce the production of an antibody against an antigenic epitope possessed by a a native or naturally-occurring LIV-1 polypeptide and an "immunological" activity refers to the ability to induce the production of an antibody against an antigenic epitope possessed by a native or naturally-occurring LIV-1 polypeptide.

"Biological activity" in the context of an antibody or another antagonist molecule that can be identified by the screening assays disclosed herein (e.g., an organic or inorganic small molecule, peptide, etc.) is used to refer to the ability of such molecules to bind or complex with the polypeptides encoded by the amplified genes identified herein, or otherwise interfere with the interaction of the encoded polypeptides with other cellular proteins or otherwise interfere with the transcription or translation of a LIV-1 polypeptide. A preferred biological activity is growth inhibition of a target tumor cell. Another preferred biological activity is cytotoxic activity resulting in the death of the target tumor cell.

The term "biological activity" in the context of a LIV-1 polypeptide means the ability of a LIV-1 polypeptide to induce neoplastic cell growth or uncontrolled cell growth or to act as an indication of a particular form of neoplasm that is particularly metastatic.

The phrase "immunological activity" means immunological cross-reactivity with at least one epitope of a LIV-1 polypeptide.

"Immunological cross-reactivity" as used herein means that the candidate polypeptide is capable of competitively inhibiting the qualitative biological activity of a LIV-1 polypeptide having this activity with polyclonal antisera raised against the known active LIV-1 polypeptide. Such antisera are prepared in conventional fashion by injecting goats or rabbits, for example, subcutaneously with the known active analogue in complete Freund's adjuvant, followed by booster intraperitoneal or subcutaneous injection in incomplete Freunds. The immunological cross-reactivity preferably is "specific", which means that the binding affinity of the immunologically cross-reactive molecule (e.g. antibody) identified, to the corresponding LIV-1 polypeptide is significantly higher (preferably at least about 2-times, more preferably at least about 4-times, even more preferably at least about 8-times, most preferably at least about 10-times higher) than the binding affinity of that molecule to any other known native polypeptide.

The term "antagonist" is used in the broadest sense, and includes any molecule that partially or fully blocks, inhibits, or neutralizes a biological activity of a native LIV-1 polypeptide disclosed herein or the transcription or translation thereof. Suitable antagonist molecules specifically include antagonist antibodies or antibody fragments, fragments, peptides, small organic molecules, anti-sense nucleic acids, etc. Included are methods for identifying antagonists of a LIV-1 polypeptide with a candidate antagonist molecule and measuring a detectable chance in one or more biological activities normally associated with the LIV-1 polypeptide.

A "small molecule" is defined herein to have a molecular weight below about 500 Daltons.

The word "label" when used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd109.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate: in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a LIV-1 polypeptide or antibody thereto and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin," for example a receptor, ligand, or enzyme) with the effector functions of immunoglobulin constant domains. Structurally, the immunoadhesins comprise a fusion of the adhesin amino acid sequence with the desired binding specificity which is other than the antigen recognition and binding site (antigen combining site) of an antibody (i.e., is "heterologrous"), and an immunoglobulin constant domain sequence. The adhesin part of an immunoadhesin molecule typically is a continuous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM, and any subclass or isotype thereof.

The terms "HER2", "ErbB2" "c-Erb-B2" are used interchangeably. Unless indicated otherwise, the terms "ErbB2" "c-Erb-B2" and "HER" when used herein refer to the human protein, and "erbB2,", "c-erb-B2," and "her2" refer to human gene. The human erbB2 gene and ErbB2 protein are, for example, described in Semba et al., *PNAS (USA)* 82:6497-6501 (1985) and Yamamoto et al., *Nature* 319:230-234 (1986)(Genebank accession number X03363). ErbB2 comprises four domains (Domains 1-4).

The "epitope 4D5" is the region in the extracellular domain of ErbB2 to which the antibody 4D5 (ATCC CRL 10463) binds. This epitope is close to the transmembrane region of ErbB2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of ErbB2 (i.e. any one or more residues in the region from about residue 529, e.g. about residue 561 to about residue 625, inclusive).

The "epitope 3H4" is the region in the extracellular domain of ErbB2 to which the antibody 3H4 binds. This epitope includes residues from about 541 to about 599, inclusive, in the amino acid sequence of ErbB2 extracellular domain.

The "epitope 7C2/7F3" is the region at the N terminus of the extracellular domain of ErbB2 to which the 7C2 and/or 7F3 antibodies (ATCC HB-12215 and ATCC HB-12216, respectively) bind. To screen for antibodies which bind to the 7C2/7F3 epitope, a routine cross-blocking assay such as that described in *Antibodies, A Laboratory Manual,* Cold Spring Harbor Laboratory, Ed Harlow and David Lane (1988), can be performed. Alternatively, epitope mapping can be performed to establish whether the antibody binds to the 7C2/7F3 epitope on ErbB2.

The term "induces cell death" or "capable of inducing cell death" refers to the ability of the anti-LIV-1 gene product antibody, alone or in co-treatment with a chemotherapeutic agent, to make a viable cell become nonviable. The "cell" here is one which expresses the LIV-1 gene product, especially where the cell overexpresses the LIV-1 gene product. A cell which "overexpresses" LIV-1 has significantly higher than normal LIV-1 mRNA and/or LIV-1 protein levels compared to a noncancerous cell of the same tissue type. A cell to be treated by the method of the invention does not also overexpress ErbB2 (i.e. the cell expresses ErbB2 at a level that is approximately the same or less than a normal, non-cancerous cell of the same cell or tissue type). Preferably, the cell is a cancer cell, e.g. a breast, lung, or prostate cell, In vitro, the cell may be from a cell line transformed with LIV-1 DNA, preferably DNA 164647, to express LIV-1 on the cell surface. Cell death in vitro may be determined in the absence of complement and immune effector cells to distinguish cell death induced by antibody dependent cellular cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al., *Cytotechnology* 17:1-11 [1995]) or 7AAD can be assessed relative to untreated cells. Preferred cell death-inducing antibodies are those which induce PI uptake in the "PI uptake assay in LIV-1 expressing cells".

The phrase "induces apoptosis" or "capable of inducing apoptosis" refers to the ability of the antibody to induce programmed cell death as determined by binding of annexin V, fragmentation of DNA, cell shrinkage, dilation of endoplasmic reticulum, cell fragmentation, and/or formation of membrane vesicles (called apoptotic bodies). The cell is one which overexpresses the LIV-1 gene product. Preferably the "cell" is a tumor cell, e.g. a breast, lung, or prostate cell. In vitro, the cell may be from a cell line transformed with LIV-1 DNA, such as DNA 164647. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold induction of annexin binding relative to untreated cell in an "annexin binding assay using cells" (see below).

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vitro serum half-life of the IgG molecule.

"Treatment" refers to both therapeutic treatment and prophylactic or preventative measures. Those in need of treatment include those already with the disorder as well as those in which the disorder is to be prevented.

A "disorder" is any condition that would benefit from treatment with the anti-LIV-1 gene product antibody. This includes chronic and acute disorders or diseases including those pathological conditions which predispose the mammal to the disorder in question. Non-limiting examples of disorders to be treated herein include benign and malignant tumors of breast, lung, and prostate tissue.

The term "package insert" is used to refer to instructions customarily included in commercial packages of therapeutic products, that contain information about the indications, usage, dosage, administration, contraindications and/or warnings concerning the use of such therapeutic products.

The term "serum concentration," "serum drug concentration," or serum anti-LIV-1 "antibody concentration" refers to the concentration of a drug in the blood serum of an animal or human patient being treated with the drugs. Serum concentration of antibody, for example, is preferably determined by immunoassay. Preferably, the immunoassay is ELISA according to the procedure disclosed herein.

The term "peak serum concentration" refers to the maximal serum drug concentration shortly after delivery of the drug into the animal or human patient, after the drug has been distributed throughout the blood system, but before significant tissue distribution, metabolism or excretion of drug by the body has occurred.

The term "trough serum concentration" refers to the serum drug concentration at a time after delivery of a previous dose and immediately prior to delivery of the next subsequent dose of drug in a series of doses. Generally, the trough serum concentration is a minimum sustained efficacious drug concentration in the series of drug administrations. Also, the trough serum concentration is frequently targeted as a minimum serum concentration for efficacy because it represents the serum concentration at which another dose of drug is to be administered as part of the treatment regimen. If the delivery of drug is by intravenous administration, the trough serum concentration is most preferably attained within 1 day of a front loading initial drug delivery. It the delivery of drug is by subcutaneous administration, the peak serum concentration is preferably attained in 3 days or less. According to the invention, the trough serum concentration is preferably attained in 4 weeks or less, preferably 3 weeks or less, more preferably 2 weeks or less, most preferably in 1 week or less, including 1 day or less using any of the drug delivery methods disclosed herein.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug deliver, pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

The term "front loading," when referring to drug administration is meant to describe an initially higher dose followed by the same or lower doses at intervals. The initial higher dose or doses are meant to more rapidly increase the animal or human patient's serum drug concentration to an efficacious target serum concentration.

Published information related to LIV-1 gene expression and gene product includes the following issued patents and published applications: Manning, D. L. et al., U.S. Pat. No. 5,693,465, issued Dec. 2, 1997; Manning, D. L. et al., European J. Cancer 29A(10):1462-1468 [1993]; Manning, D. L. et al., European J. Cancer, 30A(5):675-678 [1994]; Manning. D. L. et al., Acta Oncologica 34(5):641-646 [1995]; McClelland, R. A. et al., Breast Cancer Res. & Treatment 41(1):31-41 [1996]; Knowlden, J. M. et al. Clin. Cancer Res. 3(11):2165-2172 [1997]; and McClelland, R. A. et al., British J. Cancer 77(10):1653-1656 [1998].

Published information related to anti-ErbB2 antibody includes the following issued patents and published applications: PCT/US89/00051, published Jan. 5, 1989, PCT/US90/02697, published May 18, 1990, EU 0474727, issued Jul. 23, 1997, DE 69031120.6, issued Jul. 23, 1997, PCT/US97/18385, published Oct. 9, 1997, SA 97/9185, issued Oct. 14, 1997, U.S. Pat. No. 5,677,171, issued Oct. 14, 1997, U.S. Pat. No. 5,720,937, issued Feb. 24, 1998. U.S. Pat. No. 5,720,954, issued Feb. 24, 1998, U.S. Pat. No. 5,725,856, issued Mar. 10, 1998, U.S. Pat. No. 5,770,195, issued Jun. 23, 1998, U.S. Pat. No. 5,772,997, issued Jun. 30, 1998, PCT/US98/2626, published Dec. 10, 1998, and PCT/US99/06673, published Mar. 26, 1999, each of which patents and publications is herein incorporated by reference in its entirety.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described herein and in the following textbooks: Sambrook et al., *Molecular Cloning: A Laboratory Manual*, Cold Spring Harbor Press N.Y. 1989; Ausubel et al., *Current Protocols in Molecular Biology*, Green Publishing Associates and Wiley Interscience, N.Y. 1989; Innis et al., *PCR Protocols: A Guide to Methods and Applications*, Academic Press, inc., N.Y. 1990; Harlow et al., *Antibodies: A Laboratory Manual*, Cold Spring Harbor Press, Cold Spring Harbor, 1988; Gait, M. J. *Oligonucleotide Synthesis*, IRL Press, Oxford, 1984, R. I. Freshney, *Animal Cell Culture*, 1987 Coligan et al., *Current Protocols in Immunology*, 1991.

Example 1

LIV-1 Expression in Tumor Cells Examined by Microarray Analysis

A form of breast cancer in which the cells overexpress the LIV-1 gene product (e.g. LIV-1-164647 mRNA) but do not overexpress ErbB2 has been discovered and is uniquely disclosed herein. Detection of the tumor type was made using microarray technology. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

Tumor cells were crossly dissected from surrounding, non-cancerous cells in breast tumor tissue. Hematoxylin and eosin staining of the cells confirmed that the excised cells were from tumor. The mRNA of the tumor cells (reflecting cell-specific expression of a variety of genes) was converted to cDNA by RT/PCR methodology, labeled with fluorescent tags, and allowed to hybridize to the ESTs arrayed on a class slide. An imaging device detected and measured the fluorescence of each sample on the slide, where fluorescence represents a labeled messenger from the test cells identifiable due to its hybridization with a known nucleic acid sequence (an EST) at a known position on the slide. Relative fluorescence indicated relative activity of a gene, with strong flourescence indicating an active gene expressing a relative large amount of messenger. Little or no flourescence indicated that no labeled messenger hybridized to the ESTs. Detection of fluorescently labeled probes hybridized to sequences on the microarray slide is described, for example, in U.S. Pat. No. 5,143,854, herein incorporated by reference.

It was found that cDNA of the preparation hybridized to a publicly available EST sequence (accession no. H29315 (from the Washington University-Merck EST Project, authors Hillier. L. et al., SEQ ID NO:5, purchased from Research Genetics (Alabama, USA) in a pattern suggesting overexpression in breast tumor tissue that did not also overexpress ErbB2. The cDNA was sequenced and disclosed herein as LIV-1-DNA 164647. In situ hybridization of a radioactively labeled LIV-1-164647 probe to a tissue microarray of tumor tissues further indicated LIV-1 expression in tumors from breast, lung, prostate, colon, endometrial, ovarian, and transitional carcinomas, and melanoma tissue samples.

It was further discovered that breast tumor cells which overexpressed LIV-1 did not overexpress ErbB2 relative to a normal cell of the same type (where a normal cell refers to a cell that is not cancerous and free of any other disease in which LIV-1 may be overexpressed). The very low expression of LIV-1 in normal tissues relative to the overexpression of LIV-1 in breast tumor cells makes LIV-1 a desirable target for a therapeutic antibody.

For example, in breast tumors, strong fluorescent detection of LIV-1 occurred with low detection of ErbB2 expression, or alternatively strong flourescent detection of ErbB2 was observed in the absence of LIV-1 mRNA expression. Of 17 samples, each from a different breast tumor of variable tumor cell content, 6 samples showed moderate to strong LIV-1 expression, and 6 showed moderate or strong ErbB2 expression. There was an overlap in one tumor which showed moderate ErbB2 and LIV-1 expression. In another tumor it appeared that strong detection of ErbB2 expression was accompanied by very weak detection of LIV-1 expression. Cell lines expressing endogenous or exogenous LIV 1 protein (preferably LIV-1-164647), but not overexpressing ErbB2, are thus useful for testing the detection or LIV-1 expression relative to ErbB2 expression. Such cells are also useful to test anti-LIV-1 antibodies for binding to LIV-1-164647 expressing cells and their affects on cell growth.

Regions of LIV-1-164647 in the ECD and in the C-terminus were found to be unique as compared to the LIV-1 sequence of Green et al., (see FIG. 4 comparing SEQ ID NO:4 and GenBank Accession No. AAA96258). The region spanned amino acids 126 to and including amino acid 132 of SEQ ID NO:4 (SEQ ID NO:17) and amino acids 743 to 755 (SEQ ID NO:18). A larder histidine-rich region from amino acid 114 to and including amino acid 135 (SEQ ID NO:19) is also encompassed by the invention. Thus, according to the presently disclosed invention, the nucleic acid of the invention comprises a sequence having at least 65%, preferably at least 75%, more preferably at least 85%, still more preferably at least 90%, and most preferably at least 96% homologous to a sequence from approximately nucleotide 412 to and including nucleotide 477 of SEQ ID NO:3, or its complementary sequence. Preferably, the nucleic acid of the invention comprises a sequence from nucleotide 443 to and including nucleic acid 446 of SEQ ID NO:3. The present invention further includes an isolated polypeptide comprising an amino acid sequence having at least 65%, preferably at least 75%, more preferably at least 85%, still more preferably at least 90%, and most preferably at least 96% homology to a sequence from approximately amino acid 114 to and including amino acid 135 of SEQ ID NO:4. Preferably, the isolated polypeptide of the invention comprises an amino acid sequence from amino acid 126 to and including amino acid 132 of SEQ ID NO:4.

Example 2

Preparation of the LIV-1 Polypeptides

A previously unknown LIV-1 gene and its encoded protein are uniquely disclosed herein. The nucleic acid sequence of LIV-1 (DNA 164647; SEQ ID NO:3 and its complement) and amino acid sequence of LIV-1 encoded therein (SEQ ID NO:4) are uniquely disclosed herein. This example describes the preparation and isolation of the presently disclosed LIV-1 protein encoded by DNA 164647. Subsequent examples describe the tissue expression profile of LIV-1 and its partial exposure at the cell surface. The LIV-1 gene is disclosed herein to be expressed in various tumor tissues including breast, lung, prostate, and colon. Cell surface expression of this tumor-associated protein makes LIV-1 a useful target for cancer detection and treatment.

The LIV-1 described by DNA 164647 has a unique nucleic acid sequence and unique amino acid sequence. The presently disclosed LIV-1 differs in nucleic acid sequence and amino acid sequence from another form of LIV-1 protein previously described by Green et al., (see Green, C. et al., direct submission, GenBank Accession Nos. U41060 (nucleic acid sequence) and AAA96258 (amino acid sequence)). The nucleic acid sequence of AAA96258 LIV-1 (SEQ ID NO:1 (coding sequence)) is shown in FIG. 1A. The predicted amino acid sequence (AAA96258; SEQ ID NO:2) encoded by nucleic acid sequence U41061 (SEQ ID NO: 1) is shown in FIG. 1B. Included in the diagram are predictions for sequences encoding a signal sequence, extracellular domain, and transmembrane domain. Significantly, the presently disclosed LIV-1 (DNA 164647) differs in predicted extracellular domain region.

The present invention provides methods for using DNA 64647 encoding LIV-1 polypeptide for the production of compounds inhibiting neoplastic growth as well as for the preparation of screening methods for identifying growth inhibitory compounds (e.g. tumor compounds). In particular, cDNAs encoding certain LIV-1 polypeptides. For the sake of simplicity, in the present specification the proteins encoded by nucleic acid referred to as "DNA 164647", as well as all further native homologues and variants included in the foregoing definition of LIV-1 polypeptide, will be referred to as "LIV-1" polypeptide, regardless of their origin or mode of expression.

Cloning of DNA 164647 LIV-1 nucleic acid: Full Length Inverse PCR ("FLIP"), also referred to as inverse long distance PCR because of the ability of this method to isolate long genes, was used to clone DNA 164647 LIV-1 nucleic acid. The FLIP PCR technique is described in pending U.S. application Ser. No. 09/480,782, filed Jan. 10, 2000. J. C. Grimaldi et al (inventors), Genentech, Inc. (assignee), which application is herein incorporated by reference in its entirety, particularly with respect to the method of cloning a gene. While standard cloning techniques may be used to clone full length genes. FLIP is a very rapid and high-throughput method of isolating an entire clone, vector plus insert, of a specific nucleic acid molecule from any nucleic acid library which was propagated in a host cell that methylates the nucleic acid library. The FLIP cloning method amplifies a target gene or nucleotide sequence and generates a highly purified population of the target gene. FIG. 5 is a flow diagram of a FLIP cloning process. DNA 164647 was isolated by FLIP methodology using the following primers and probe.

forward primer: (SEQ ID NO:6)
LIV1-INV5' 5'ATGTTGACTTGGCAATTTCCACACGGCA3'

```
                                      -continued
reverse primer:
                                                        (SEQ ID NO:7)
LIV1-INV3'    5'TAATGCCAGATTCCCAATTCGGACTAA3' probe:
                                                        (SEQ ID NO:8)
LIV1-p        5'TTAGTTCATGAAGGGGATTTGTGACAGAGAGGGCAAAGGTCAGGAT3'.
```

A human LIV-1 gene (Genbank Accession#U41060) has been sequenced by C. Green et al. (direct submission, Nov. 21, 1995). The sequence is 3461 bp (SEQ ID NO:1; FIG. 1A) and includes the an open reading frame (ORF). Using the FLIP methodology and the primers and probe disclosed above, a cDNA clone was isolated from a pool of fifty human cDNAs from cDNA libraries representing various tissues (Genentech cDNA libraries, Genentech, Inc., So, San Francisco, Calif.). The isolated cDNA clone includes a LIV-1 gene comprising a variant nucleic acid sequence (DNA 164647; SEQ ID NO:3 (coding sequence) and its complementary sequence) and a variant deduced amino acid sequence (SEQ ID NO:4). The total length of the isolated LIV-1 DNA 164674 nucleic acid is 2776 bp, the vector pRK5D used was 5.1 kb, thus adding to a total length of 7.9 kb of the DNA molecule amplified by IPCR and isolated.

A nucleic acid sequence comparison of the LIV-1 submitted by Green et al., supra, and DNA 164647 disclosed herein is shown in FIG. 3. Asterisks denote identity between nucleotides, while dashes represent gaps where no identity occurs. An insertion of 18 nucleotides is observed at approximately nucleotides 446 to 463 of DNA 164647 (SEQ ID NO:3) and two single nucleotide insertions occur at nucleotides 2297 and 2323 causing a frame shift and different deduced amino acid sequences in that region. FIG. 4 is a comparison of the amino acid sequences of the LIV-1 polypeptides of SEQ ID NO:2 (see Green et al., supra) and SEQ ID NO:4 (disclosed herein). A six-amino acid insertion is observed at approximately amino acids 126 to 131 in the ECD, while different amino acid sequences are observed at the C-terminal end of the polypeptides due to single nucleotide insertions (see amino acids beyond amino acid 736 of SEQ ID NO:2 and beyond amino acid 742 of SEQ ID NO:4).

Specifically; DNA 164647 isolation was performed according to the following procedure. Two adjacent 5' phosphorylated primers. LIV1-INV5' and LIV1-INV3', were designed on opposite strands. These primers. SEQ ID NO:6 and SEQ ID NO:7, were used in an inverse PCR reaction. In a 50 ul reaction, the following reagents were added: 50 ng of a bone marrow cDNA library in a modified pRK5D vector, which was propagated in a methylation positive bacteria, 50 picomoles of each PCR primer; 10 mmoles of each deoxynucleotide triphosphate, 5 ul of Pfu 10× buffer (Stratagene, La Jolla Calif.), and 1 ul of Pfu Turbo (Stratagene, La Jolla Calif.). The plasmid vector pRK5 (4,661 bp) has been described (EP 307,247 published Mar. 15, 1989). The modified pRK5 vector (pRK5.tk.neo) is a derivative of pRK5 in which the neomycin resistance gene is inserted thereby allowing for selection of G418-resistant clones.

The PCR cycle conditions were one cycle at 94° C. for 3 minutes, then 94° C. for 30 seconds, 65° C. for 30 seconds, 72° C. for 13 minutes for 20 cycles. PCR conditions may, of course, be modified to meet specific needs of amplification. The PCR reaction generated a linear 5' phosphorylated amplicon that contained the LIV-1 cDNA insert plus the pRK5D vector.

Next, 10 ul of the completed PCR reaction was ligated in a 100 ul reaction containing the following other reagents: 10 ul 10×T4 DNA ligase buffer (New England BioLabs, Beverly, Mass.). 4 ul T4 DNA ligase (New England BioLabs, Beverly, Mass.), 76 ul $H_2O$. The ligation was allowed to incubate at ambient temperature for 1 hour on the bench top.

After 1 hour of ligation, 2 ul of the restriction enzyme Dpn1 (New England BioLabs, Beverly, Mass.) was added to the ligation reaction and the digestion was allowed to continue for 1 hour at 37° C. Dpn1 will specifically digest methylated DNA and not unmethylated DNA; therefore, the original cDNA library which was used as a template will be digested, leaving only the LIV-1/vector amplicon intact. After the completion of the digestion the sample was cleaned using the QIAquick PCR purification kit (Qiagen, Valencia, Calif.), eluted in 30 ul of elution buffer or $H_2O$, and then ethanol precipitated. The pellet was resuspended in 2 ul of $H_2O$ and the entire sample was then used to transformed bacteria.

Transformation was done by electroporation into DH10B electromax competent bacteria (Life Technologies, Rockville, Md.). The transformed bacteria were plated on Luria broth agar plates and colonies allowed to grow overnight at 37° C.

The next day, the colonies were lifted onto a nylon membrane, denatured, renatured and probed with a $^{32}P$-ATP kinase-labeled, LIV-1-specific probe (SEQ ID NO:8). DNA from positive colonies was sequenced to confirm that the sequence did not contain point mutations introduced by the PCR reaction.

LIV-1 Polypeptide Production: The description below relates primarily to production of LIV-1 polypeptides by culturing cells transformed or translocated with a vector containing LIV-1-encoding nucleic acid. It is, of course, contemplated that alternative methods, which are well known in the art, may be employed to prepare LIV-1 polypeptides. For instance, the LIV-1 polypeptide sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc. 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturers instructions. Various portions of the LIV-1 polypeptide may be chemically synthesized separately and combined using chemical or enzymatic methods to produce the full-length LIV-1.

i. Alternative Methods for Synthesis or Isolation of LIV-1-Encoding DNA

Disclosed herein are various non-limiting examples of methods for isolating or synthesizing DNA as well as expressing and producing proteins. These methods are applicable and useful for the production and isolation of LIV-1-164647 gene, mRNA, and protein, or fragments thereof.

DNA encoding LIV-1-164647 polypeptide, homologues, variants, or portions thereof, may be produced by direct DNA synthesis using standard nucleic acid synthetic techniques [see, e.g., Gait, M. J., *Oligonucleotide Synthesis*, IRL Press, Oxford, 1984]. DNA synthesis in vitro may be performed using manual techniques or by automation. Automated oliogonucleotide synthesis may be accomplished, for instance, using standard techniques. Various portions of the LIV-1-encoding nucleic acid sequence may be chemically synthesized separately and combined using chemical or enzymatic methods to produce the full-length LIV-1-encoding sequence.

Alternatively, DNA encoding LIV-1 may be obtained from a cDNA library prepared from tissue believed to possess the LIV-1 mRNA and to express it at a detectable level. Accordingly, human LIV-1 DNA can be conveniently obtained from a cDNA library prepared from human tissue, such as described in the Examples. The LIV-1-encoding gene may also be obtained from a genomic library or by oligonucleotide synthesis.

Libraries can be screened with probes (such as antibodies to the LIV-1 polypeptide, or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding LIV-1 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected DNA or genomic libraries using the deduced amino acid sequence disclosed herein for the first time, and, it necessary, using conventional primer extension procedures as described in Sambrook et al., supra, to detect precursors and processing intermediates of mRNA that may not have been reverse-transcribed into cDNA.

ii. Selection and Transformation of Host Cells

Host cells are transfected or transformed with expression or cloning, vectors described herein for LIV-1 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology; a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 5:456-457 (1978) can be employed. General aspects of mammalian cell host system transformations have been described in U.S. Pat. No. 4,399,216. Transformations into yeast are typically carried out according to the method of Van Solingen et al. *J. Bact.*, 130:946 (1977) and Hsiao et al., *Proc. Natl. Acad. Sci. (USA)*, 76:3829 (1979). However, other method for introducing DNA into cells, such as by nuclear microinjection, electroporation, bacterial protoplast fusion with intact cells, or polycations, e.g., polybrene, polyornithine, may also be used. For various techniques for transformine mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31.537); *E. coli* strains are publicly (ATCC 27,325) and K5772 (ATCC 53,635).

In addition to prokaryotes, eukaryotic microbes such as filamentous fungi or yeast are suitable cloning or expression hosts for LIV-1-encoding vectors. *Saccharomyces cerevisiae* is a commonly used lower eukaryotic host microorganism.

Suitable host cells for the expression of LIV-1 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7. ATCC CRL 1651); human embryonic kidney line (293 or 293 cells subcloned for growth in suspension culture. Graham et al., *J. Gen Virol.*, 36:59 (1977)); Chinese hamster ovary cells/–DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)): human lung cells (W138, ATCC CCL 75); human liver cells (Hep G2, HB 8065): and mouse mammary tumor (MMT 060562, ATCC CCL51). The selection of the appropriate host cell is deemed to be within the skill in the art.

iii. Selection and Use of a Replicable Vector

The nucleic acid (e.g., cDNA or genomic DNA) encoding LIV-1 may be inserted into a replicable vector for cloning (amplification of the DNA) or for expression. Various vectors are publicly available. The vector may, for example, be in the form of a plasmid, cosmid, viral particle, or phage.

The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The LIV-1 polypeptide may be produced recombinantly not only directly, but also as a fusion polypeptide with a heterologous polypeptide, which may be a signal sequence or other polypeptide having a specific cleavable site at the N-terminus of the mature protein or polypeptide. In general, the signal sequence may be a component of the vector, or it may be a part of the LIV-1-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the LIV-1-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*. 77:4216 (1980). A suitable selection acne for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157(1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the LIV-1-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,7761], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encodings LIV-1.

Examples of suitable promoting sequences for use with yeast hosts include the promoters for 3-phosphoglycerate kinase [Hitzeman et al., *J. Biol. Chem.* 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde -3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothioncin, glyceraldehyde-3-phosphate dehydrogenase, and enzymes responsible for maltose and galactose utilization. Suitable vectors and promoters for use in yeast expression are further described in EP 73,657.

Transcription of LIV-1 from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a LIV-1 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the LIV-1 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding LIV-1.

Still other methods, vectors, and host cells suitable for adaptation to the synthesis of LIV-1 in recombinant vertebrate cell culture are described in Gething et al., *Nature*, 293:620-625 (1981): Mantei et al., *Nature,* 281:40-40-46 (1979); EP 117,060; and EP 117,058.

iv. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA.* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal, Conveniently, the antibodies may be prepared against a native sequence LIV-1 polypeptide or against a synthetic peptide based on the DNA sequences provided herein or against exogenous sequence fused to LIV-1 DNA and encoding a specific antibody epitope.

v. Production and Isolation of LIV-1 Polypeptide from Host Cells

Expression of LIV-1 in Mammalian Cells

This example illustrates preparation of a LIV-1 polypeptide by recombinant expression in mammalian cells.

The vector, pRK5 (see EP 307,247, published Mar. 15, 1989), is employed as the expression vector. Optionally, the LIV-1 DNA 164647 is ligated into pRK5 with selected restriction enzymes to allow insertion of the LIV-1 DNA using ligation methods such as described in Sambrook et al., supra. The resulting vector is called pRK5-DNA 164647.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-DNA 164647 DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 1-5 days.

Approximately 24 hours after the transfections, the culture medium is removed and replaced with culture medium (alone) or culture medium containing 200 μCi/ml S-cysteine and 200 μCi/ml $^{35}$S-methionine. After a 12 hour incubation, the conditioned medium is collected, concentrated on a spin filter, and loaded onto a 15% (SDS gel. The processed gel may be dried and exposed to film for a selected period of time to reveal the presence of LIV-1 polypeptide. The cultures containing transfected cells may undergo further incubation (in serum free medium) and the medium is tested in selected bioassays.

In an alternative technique. LIV-1 DNA 164647 may be introduced into 293 cells transiently using the dextran sulfate method described by Somparyrac et al., *Proc. Natl. Acad. Sci.,* 12:7575 (1981), 293 cells are grown to maximal density in a spinner flask and 700 μg pRK5-DNA 164647 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin, After about four days, the conditioned media is centrifuged and filtered to remove cells and debris. The sample containing expressed LIV-1 can then be concentrated and purified by any selected method, such as dialysis and/or column chromatography.

LIV-1 can be expressed in CHO cells. Following PCR amplification, the DNA 164647 is subcloned in a CHO expression vector using standard techniques as described in Ausubel et al., *Current Protocols of Molecular Biology,* Unit 3.16, John Wiley and Sons (1997). CHO expression vectors are constructed to have compatible restriction sites 5' and 3' of the DNA of interest to allow the convenient shuttling of cDNA's. The vector uses expression in CHO cells is as described in Lucas et al., *Nucl. Acids Res.* 24: 9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Approximately twelve micrograms of the desired plasmid DNA is introduced into approximately 10 million CHO cells using commercially available transfection reagents, such as Superfect® (Quiagen), Dosper® or Fugene® (Boehringer Mannheim). The cells are grown and described in Lucas et al., supra. Approximately $3 \times 10^{-7}$ cells are frozen in an ampule for further growth and production as described below.

The ampules containing the plasmid DNA are thawed by placement into a water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, a 250 mL. 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 was actually used, 3L production spinner is seeded at $1.2 \times 10^6$ cells/mL. On day 0, the cell number pH are determined. On day 1, the spinner is sampled and sparging with filtered air is commenced. On day 2, the spinner is sampled, the temperature shifted to 33° C. and 30 mL of 500 g/L glucose and 0.6 mL of 10% antifoam (e.g., 35% poly-dimethylsiloxane emulsion, Dow Corning 365 Medical Grade Emulsion). Throughout the production, pH is adjusted as necessary to maintain a pH of about 7.2. After 10 days, or until viability dropped below 70%, the cell culture is harvested by centrifugation and filtering through a 0.22 μm filter. The filtrate is either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes. 0.14 M NaCl and 4% mannitol, pH 6.8, with a 25 ml G25 Superfine (Pharmacia) column and stored at −80° C.

LIV-1 may be produced by transient or stable expression in a host cell, such as COS cells, using standard techniques.

Expression of LIV-1 in Yeast

The followings method describes recombinant expression of LIV-1 in yeast.

First, yeast expression vectors are constructed for intracellular production or secretion of LIV-1 from the ADH2/GAPDH promoter, DNA 164647 encoding a LIV-1 and the promoter is inserted into suitable restriction enzyme sites in the selected plasmid to direct intracellular expression of LIV-1. For secretion, DNA encoding LIV-1 can be cloned into the selected plasmid, together with DNA encoding the ADH2/GAPDH promoter, a signal peptide, such as a mammalian signal peptide, or, for example, a yeast alpha-factor or increase secretory signal/leader sequence, and linker sequences (if needed) for expression of LIV-1.

Yeast cells, such as yeast strain AB110, can then be transformed with the expression plasmids described above and cultured in selected fermentation media. The transformed yeast supernatants can be analyzed by precipitation with 10%, trichloroacetic acid and separation by SDS-PAGE, followed by staining of the gels with Coomassie Blue stain.

Recombinant LIV-1 can subsequently be isolated and purified by removing the yeast cells from the fermentation medium by centrifugation and then concentrating the medium using selected cartridge filters. The concentrate containing LIV-1 may further be purified using selected column chromatography resins.

Expression of LIV-1 in Baculovirus-Infected Insect Cells

The following method describes recombinant LIV-1 expression in Baculovirus-infected insect cells.

The sequence coding for LIV-1 is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, a nucleic acid sequence encoding LIV-1 or the desired portion of the coding sequence of LIV-1 (such as the sequence encoding the extracellular domain of a transmembrane protein or the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co transfecting, the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual* Oxford: Oxford Universal Press (1994).

Expressed poly-His tagged LIV-1 can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol, 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non specifically bound portein. After reaching $A_{280}$ baseline again, the column is developed with a 0 to 500 mM imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged LIV-1 are pooled and dialyzed against loading buffer. Alternatively, purification of the IgG tagged (or Fc tagged) LIV-1 can be performed using known chromatography techniques, including for instance, Protein A or Protein G column chromatography.

While the LIV-1 expression is performed in a 0.5-2L scale, it can be readily scaled up for larger (e.g. 8L) preparations. LIV-1 is also expressed as an IgG construct (immunoadhesin), in which the protein extracellular region is fused to an IgG1 constant region sequence containing the hinge, $C_H2$ and $C_H3$ domains and/or in poly-His tagged forms.

Following PCR amplification, the coding sequence is subcloned into a baculovirus expression vector (ph.PH.IgG for IgG fusions and pb.PH.His.c for poly-His tagged proteins), and the vector and Baculogold® baculovirus DNA (Pharmingen) is co-transfected into 105 *Spondoptera frugiperda* ("Sf9") cells (ATCC CRL 1711), using Lipofectin (Gibco BRL), pb.PH.IgG and pb.PH.His are modifications of the commercially available baculovirus expression vector pVL1393 (Pharmingen), with modified polylinker regions to include the His or Fc tag sequences. The cells are grown in Hink's TNM-FH medium supplemented with 10% FBS (Hyclone). Cells are incubated for 5 days at 28° C. The supernatant is harvested and subsequently used for the first viral amplification by injecting Sf9 cells in Hink's TNM-FH medium supplemented with 10% FBS at an approximate multiplicity of injection (MOI) of 10. Cells are incubated for 3 days at 28° C. The supernatant is harvested and the expression of the constructs in the baculovirus expression vector is determined by batch binding of 1 ml, of supernatant to 25 mL of of NI-NTA beads (Qiagen) for histidine tagged proteins or Protein-A Sepharose CL-4B beads (Pharmacia) for IgG tagged proteins followed by SDS-PAGE analysis comparing to a known concentration of protein standard by Coomassie blue staining.

The first viral amplification supernatant is used to infect a spinner culture (500 mL) of Sf9 cells grown in ESF-921 medium (Expression Systems LLC) at an approximate MOI of 0.1. Cells are incubated for 3 days at 28° C. The supernatant is harvested and filtered. Batch binding and SDS-PAGE analysis is repeated, as necessary, until expression of the spinner culture is confirmed.

The conditioned medium from the transfected cells (0.5 to 3 L) is harvested by centrifugation to remove the cells and filtered through 0.22 micron filters. For the poly-His tagged constructs, the protein construct are purified using a Ni-NTA column (Qiagen). Before purification, imidazole is added to the conditioned media to a concentration of 5 mM. The conditioned media are pumped onto a 6 mL Ni-NTA column equilibrated in 20 mM Hepes, pH 7.4, buffer containing 0.3 M NaCl and 5 mM imidazole at a flow rate of 4-5 min. at 4° C. After. loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 mL G25 Superfine (Pharmacia) column and stored at −80° C.

Immunoadhesin (Fc containing) constructs of proteins are purified from the conditioned medium as follows. The conditioned medium is pumped onto a 5 mL Protein A column (Pharmacia) which had been equilibrated in 20 mM sodium phosphate buffer, pH 6.8. After loading, the column is washed extensively with equilibration buffer before elution with 100 mM citric acid, pH 3.5. The eluted protein is immediately neutralized by collecting 1 mL fractions into tubes containing 275 of 1 M Tris buffer, pH 9. The highly purified protein is subsequently desalted into storage buffer as described above for the poly-His tagged proteins. The homogeneity of the proteins is verified by SDS-PAGE and N-terminal amino acid sequencing by Edman degradation.

vi. Purification of Polypeptide

Forms of LIV-1 polypeptides may be recovered from culture medium or from host cell lysates. If membrane-bound, it can be released from the membrane using a suitable detergent solution (e.g. Triton-X 100) or by enzymatic cleavage. Cells employed in expression of LIV-1 can be disrupted by various physical or chemical means, such as freeze-thaw cycling, sonication, mechanical disruption, or cell lysing agents.

It may be desired to purify LIV-1 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelatine, columns to bind epitope-tagged forms of the LIV-1 polypeptides. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular LIV-1 polypeptide produced.

Example 3

Preparation and Efficacy of Anti-LIV-1 Antibody

A description follows as to exemplary techniques for the production of the anti-LIV-1 antibodies used in accordance with the present invention. Techniques for the production of anti-ErbB2 antibodies may be found in the ErbB2 publications listed supra and incorporated herein by reference.

The LIV-1 antigen particularly useful for production of antibodies may be e.g., a soluble form of the extracellular domain of LIV-1-164647 or a portion thereof, containing an anitgenic epitope. The extracellular domain region is indicated in FIG. 1. Alternatively, cells expressing LIV-1 at their cell surface can be used to generate antibodies (e.g. NIH-3T3 cells transformed to overexpress LIV-1). Other forms of LIV-1 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysing residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous interjection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized is vitro. Lymphocytes then are fused with myeloma cells using a suitable fusing agent, such as polyethylene glycol, to form a hybridoma cell (Goding, *Monoclonal Antibodies: Principles and Practice*, pp.59-103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, 10801 University Boulevard. Manassas, Va. 20110-2209. Human myeloma and mouse-human heteromyeloma cell lines also have been described for the production of human monoclonal antibodies (Kozbor, *J. Immunol.*, 133:3001 (1984): Brodeur et al., *Monoclonal Antibody Production Techniques and Applications*, pp. 51-63 [Marcel Dekker, Inc., New York, 1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59-103 [Academic Press. 1986]). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature*, 348:552-554(1990). Clackson et al., *Nature*, 352: 624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 [1992]), as well as combinatorial infection and in vivo recombination as a strategy for constructing very large phage libraries (Waterhouse et al., *Nucl. Acids. Res.* 1:2265-2266 [1993]). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA.* 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

More specifically, an anti-LIV-1 monoclonal antibody is prepared as follows. An anti-LIV-1 IgG$_1$κ murine monoclonal antibody, preferably specific for the extracellular domain of LIV-1-164647 protein, is produced using procedures like those described in Fendly et al., *Cancer Research* 5o:1550-1558(1990) and WO89/06692, coupled with ordinary skill in the art. Briefly, LIV-1-expressing cells (preferably cells expressing LIV-1 encoded by DNA 164647) are harvested with phosphate buffered saline (PBS) containing 25 mM EDTA and used to immunize BALB/e mice. The mice are given injections i.p. of $10^7$ cells in 0.5 ml PBS on weeks, 0, 2, 5 and 7, for example. The mice with antisera that immunoprecipitates $^{32}$P-labeled LIV-1 protein, preferably by binding to the extracellular domain or extracellular fragments, are given i.p. injections of a wheat germ agglutinin-Sepharose (WGA) purified LIV-1 membrane extract on weeks 9 and 13. This is followed by an i.v. injection of 0.1 ml of the LIV-1 preparation and the splenocytes are fused with mouse myeloma line X63-Ag8.653, for example, Hybridoma supernatants are screened for LIV-1-binding by ELISA and radioimmunoprecipitation, MOPC-21 (IgG1), (Cappell, Durham, N.C.), is used as an isotype-matched control. The disclosed method of preparing an anti-LIV-1 antibody is provided as an example since other methods for producing monoclonal antibodies are contemplated.

The treatment is performed with a humanized version of the murine anti-LIV-1 antibody. The humanized antibody is engineered by inserting the complementarity determining regions of the murine anti-LIV-1 antibody into the framework of a consensus human immunoglobulin IgG$_1$ (IgG$_1$) (see for example the process used in Carter et al., *Proc. Natl. Acad. Sci. USA* 89:4285-4289 [1992]). The resulting humanized anti-LIV-1 monoclonal antibody preferably has high affinity for the extracellular domain of LIV-1 protein and inhibits, in vitro and in vivo and in human xenografts, the growth of breast cancer cells, lung cancer cells, prostate cancer cells or other cell that overexpresses LIV-1 protein. Preferably the anti-LIV-1 antibodies of the invention inhibit tumor cell growth greater than 20%, most preferably greater than 50%, in vitro. The preferred anti-LIV-1 monoclonal antibody of the invention is also clinically active, as a single agent or in combination with a cytotoxic or other cell growth-inhibiting agent, in patients with LIV-1-overexpressing metastatic breast cancers, or lung, prostate or other cancers. Anti-LIV-1 monoclonal antibody is produced by a genetically engineered Chinese Hamster Ovary (CHO) cell line, grown in large scale, that secretes the antibody into the culture medium. The antibody is purified from the CHO culture media using standard chromatographic and filtration methods. Each lot of antibody is assayed to verity identity, purity, and potency, as well as to meet Food and Drug Administration requirements for sterility and safety.

When used to kill human cancer cells in vitro for diagnostic purposes or to test the potency of a lot of antibodies, the antibodies will typically be added to a culture of LIV-1-overexpressing cells, particularly cancerous cells, that do not also overexpress ErbB2. As a control, the antibodies will also be added to a culture of cells that do not overexpress LIV-1. The antibodies are added to the cell culture medium at a concentration of at least approximately 10 nM. The formulation and mode of administration for in vitro use are not critical. Aqueous formulations that are compatible with the culture or perfusion medium will normally be used. Cytotoxicity may be read by conventional techniques to determine the presence or degree of cancer.

Cytotoxic radiopharmaceuticals for treating cancer may be made by conjugating radioactive isotopes (e.g. I, Y, Pr) to the antibodies. The term "cytotoxic moiety" as used herein is intended to include such isotopes.

In another embodiment, liposomes are filled with a cytotoxic drug and the liposomes are coated with antibodies specifically binding a growth factor receptor. Since there are many receptor sites, this method permits delivery of large amounts of drug to the correct cell type.

Antibody dependent cellular cytotoxicity (ADCC) is contemplated as a method of targeting cytotoxic effects to cancerous cells overexpressing LIV-1 protein. The present invention involves a method based on the use of antibodies withic are (a) directed against the extracellular domain of LIV-1 protein, and (b) belong to a subclass or isotype that is capable of mediating the lysis of tumor cells to which the antibody molecule binds. More specifically, these antibodies should belong to a subclass or isotype that, upon complexing with growth factor receptors, activates serum complement and/or mediates antibody dependent cellular cytotoxicity (ADCC) by activating effector cells such as natural killer cells or macrophages.

The present invention is also directed to the general use of these antibodies, in their native form, for therapy of human tumors that overexpress the LIV-1 protein. For example, many IgG2a and IgG3 mouse antibodies which bind tumor-associated cell surface antigens can be used in vivo for tumor therapy. In fact, since LIV-1 is present on a variety of tumors, the subject antibodies and their therapeutic use have general applicability.

(iii) Humanized and Human Antibodies

Methods for humanizing non-human antibodies are well known in the art. Preferably, a humanized antibody has one or more amino acid residues introduced into it from a source which is non-human. These non-human amino acid residues are often referred to as "import" residues, which are typically taken from an import variable domain. Humanization can be essentially performed following the method of Winter and co-workers (Jones et al., Nature, 321:522-525 (1986), Riechmnann et al., Nature, 332:323-327 (1988); Verhoeyen et al., Science, 239:1534-1536 [1988]), by substituting rodent hypervariable regions (e.g., CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151:2296 (1993); Chothia et al., J. Mol. Biol. 196:901 [1987]). Another method uses a particular framework region derived from the consensus sequence of all human antibodies of a particular subgroup of light or heavy chains. The same framework may be used for several different humanized antibodies (Carter et al., Proc. Natl. Acad. Sci. USA. 89:4285 (1992); Presta et al., J. Immnol. 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakohovits et al., Proc. Natl. Acad. Sci. USA. 90:2551 (1993); Jakohovits et al., Nature, 362:255-258 (1993); Bruggermann et al., Year in Immunol. 7.33 (1993). Human antibodies can also be derived from phage-display libraries (Hoogenboom et al., J. Mol. Biol., 227:381 (1991); Marks et al., J. Mol. Biol., 222:581-597 [1991]).

(iv) Antibody Fragments

Various techniques have been developed for the production of anti body fragments. Traditionally, these fragments were derived via proteolytic digestion of intact antibodies (see, e.g., Morimoto et al., *Journal of Biochemical and Biophysical Methods* 24:107-117(1992) and Brennan et al., *Science,* 229:81 [1985]). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 [1992]). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(v) Bispecific Antibodies

Bispecific antibodies are antibodies that have binding specificities for at least two different epitopes. Exemplary bispecific antibodies may bind to two different epitopes of the LIV-1 protein. For example, one arm may bind a first epitope in the extracellular domain of LIV-1 protein, while the other may bind a different LIV-1 epitope. Alternatively, an anti-LIV-1 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express LIV-1 by binding to the extracellular domain of the LIV-1 gene product. These antibodies possess a LIV-1 extracellular domain-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 [1983]). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge. CH2, and CH3 regions. It is preferred to have the first heavy-chain constant region (CH1) containing the site necessary for light chain binding, present in at least one of the fusions. DNAs encoding the immuno-globulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one hall of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenile to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzyme.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets. Similar techniques are used to prepare a bispecific antibody able to bind cells overexpressing LIV-1 but not overexpression ErbB2.

Various techniques for making and isolating bispecific antibody fragments directly from recombinant cell culture have also been described. For example, bispecific antibodies have been produced using leucine zippers. Kostelny et al., *J. Immunol.*, 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA.* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147: 60 (1991).

(vi) Screening for Antibodies with the Desired Properties

Techniques for generating antibodies have been described above. Those antibodies having the characteristics described herein are selected.

To select for antibodies which induce cell death, loss of membrane integrity as indicated by, e.g., PI, trypan blue or 7AAD uptake is assessed relative to control. The preferred assay is the "PI uptake assay using BT474 cells". According to this assay, BT474 cells (which can be obtained from the American Type Culture Collection [Manassas, Va.]) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of 3×10$^6$ per dish in 100×20 mm dishes and allowed to attach overnight. The medium is then removed and replaced with fresh medium alone or medium containing 10 µg/ml of the appropriate MAb. The cells are incubated for a 3 day time period. Followings each treatment, monolayers are washed with PBS and detached by trypsinization. Cells are then centrifuged at 1200 rpm for 5 minutes at 4° C. the pellet resuspended in 3 ml ice cold Ca$^{2+}$ binding buffer (10 nM Hepes, pH 7.4, 140 mM NaCl, 2.5 mM CaCl$_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake are selected.

In order to select for antibodies which induce apoptosis, an "annexin binding assay using BT474 cells" is available. The BT474 cells are cultured and seeded in dishes as discussed in the preceding, paragraph. The medium is then removed and replaced with fresh medium alone or medium containing 10 µg/ml of the MAb. Following a three day incubation period, monolayers are washed with PBS and detached by trypsinization. Cells are then centrifuged, resuspended in Ca$^{2+}$ binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a "DNA staining assay using BT474 cells" is available. In order to perform this assay, BT474 cells which have been treated with the antibody of interest as described in the preceding two paragraphs are incubated with 9 µg/ml HOECHST 33342™ for 2 hr at 37° C. then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To screen for antibodies that bind to an epitope on the extracellular domain of LIV-1-164647, a routine cross-blocking assay such as that described in *Antibodies, A Laboratory Manual*, Cold Spring Harbor Laboratory, Ed Harlow and David Lane (1988), can be performed. Alternatively, epitope mapping can be performed by methods known in the art (see, for example, methods used for the epitope-mapping of the extracellular domain of ErbB2 as determined by truncation mutant analysis and site-directed mutagenesis (Nakamura et al., *J. of Virology* 67(10):6179-6191 [October 1993]; Renz et al., *J. Cell Biol.* 125(6):1395-1406 [June 1994]). In addition, where aparticular amino acid sequence is suspected of forming all or a substantial portion of an epitope, a polypeptide consisting of that sequence may be contacted with the antibody and tested, using standard techniques, for its ability to compete for binding to the LIV-1-164647, such as the LIV-1-164647 ECD.

To identify anti-LIV-1 antibodies which inhibit growth of LIV-1-expressing cells in cell culture by 50-100%, an assay can be performed generally as follows: LIV-1-expressing cells are grown in a 1:1 mixture of F12 and DMEM medium supplemented with 10% fetal bovine serum, glutamine and penicillinstreptomycin. The LIV-1-expressing cells are plated at 20,000 cells in a 35 mm cell culture dish (2 mls/35 mm dish), 2.5 µg/ml of the anti-LIV -1 antibody is added per dish. After six days, the number of cells, compared to untreated cells are counted using an electronic COULTER™ cell counter. Those antibodies which inhibit growth of the LIV-1-expressing cells by 50-100% are selected for combination with the apoptotic antibodies as desired.

(vii) Effector-Function Engineering

It may be desirable to modify the antibody of the invention with respect to effector function, so as to enhance the effectiveness of the antibody in treating cancer, for example. For example, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes. B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-ErbB2 antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelatine ardent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The anti-LIV-1 antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980): and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction A chemotherapeutic agent is optionally contained within the liposome. See Gabizon et al., *J. National Cancer Inst.* 81(19) 1484 (1989).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to alkaline phosphatase useful for converting phosphate-containing prodrugs into free drugs; arylsulfatase useful for converting sulfate-containing prodrugs into tree drugs; cytosing deaminase useful for converting non-toxic 5-fluorocytosing into the anti-cancer drug, 5-fluorouracil; proteases, such as serratia protease, thermolysin, subtilisin, carboxy peptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs, Alternatively, antibodies with enzymatic activity, also known in the art as "abzymes", can be used to convert the prodrugs of the invention into free active drugs (see, e.g., Massey, *Nature* 328: 457-458 [1987]). Antibody-abzyme conjugates can be prepared as described herein for delivery of the abzyme to a tumor cell population.

The enzymes of this invention can be covalently bound to the anti-LIV-1 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 [1984]).

(xi) Antibody-Salvage Receptor Binding Epitope Fusions

In certain embodiments of the invention, it may be desirable to use an antibody fragment, rather than an intact antibody, to increase tumor penetration, for example. In this case, it may be desirable to modify the antibody fragment in order to increase its serum hall life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

A systematic method for preparing such an antibody variant having an increased in vivo half-life comprises several steps. The first involves identifying the sequence and conformation of a salvage receptor binding epitope of an Fc region of an IgG molecule. Once this epitope is identified, the sequence of the antibody of interest is modified to include the sequence and conformation of the identified binding epitope. After the sequence is mutated, the antibody variant is tested to see if it has a longer in vivo half-life than that of the original antibody. It the antibody variant does not have a longer in vivo half-life upon testing, its sequence is further altered to include the sequence and conformation of the identified binding epitope. The altered antibody is tested for longer in vivo half-life, and this process is continued until a molecule is obtained that exhibits a longer in vivo half-life.

The salvage receptor binding epitope being thus incorporated into the antibody of interest is any suitable such epitope as defined above, and its nature will depend, e.g., on the type of antibody being modified. The transfer is made such that the antibody of interest still possesses the biological activities described herein.

The epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the $C_H2$ domain of the Fc region (e.g., of an IgG) and transferred to the $C_H1$, $C_H3$, or $V_H$ region, or more than one such region, of the antibody. Alternatively, the epitope is taken from the $C_H2$ domain of the Fc region and transferred to the $C_L$ region or $V_L$ region, or both, of the antibody fragment.

(xii) Purification of Anti-LIV-1 Antibody

When using recombinant techniques, the antibody can be produced intracellularly, in the periplasmic space, or directly secreted into the medium. It the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5). EDTA, and phenylmethylsulfonylfluoride (PMSF) over about 30 min. Cell debris can be removed by centrifugation. Where the antibody is secreted into the medium, supernatants from such expression systems are preferably first concentrated using a commercially available protein concentration filter, for example an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purity antibodies that are based on human γ1, γ2, or γ4 heavy chains (Lindmark et al., *J. Immunol. Meth.* 62:1-13 [1983]). Protein G is recommended for all mouse isotypes and for human γ3 (Guss et al., *EMBO J.* 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain the Bakerbond ABX™ resin (J. T. Baker, Phillipsburg, N.J.) is useful for purification. Other techniques for protein purification such as fractionation on an ion-exchange column, ethanol precipitation. Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

Example 4

LIV-1 is Expressed on the Cell Surface

Analysis of the deduced amino acid sequence of LIV-1 indicated that a portion of the protein exists as an extracellular domain (ECD). To verify this finding, the ECD was expressed, purified, and used as an antigen for the development of anti-LIV-1 ECD antibodies. The antibodies were contacted with cells expressing the full length LIV-1 protein. This Example shows that anti-LIV-1 ECD antibodies bound to LIV-1-expressing cells, demonstrating that LIV-1 comprises an extracellular domain.

Expression of LIV-1 ECD in *E. coli*

To obtain samples of the LIV-1 ECD to which antibodies could be raised, a polypeptide comprising the extracellular domain of LIV-1 was expressed in *E. coli* after first constructing a nucleic acid vector encoding the LIV-1 extracellular domain operably linked to an amino acid leader sequence. The following procedures were used to prepare the nucleic acid construct and express the encoded protein.

DNA coding for amino acids 1-298, encoding the extracellular domain of mature LIV-1, was prepared by standard PCR techniques from a full length cDNA clone using the primers 5'-CAACATCAAATGCATCAACTTCATGAAC-TAAAAGCAGCTGCT-3' (SEQ ID NO:9) and 5'-GAGCTCGAGCGGCCGCTTAGGTCTTTG-GAGGGATTTCAGCCTT-3' (SEQ ID NO:10). The PCR reaction was divided in two: one half was digested with NsiI and SacI, while the other half was digested with SacI and NotI. The NsiI-SacI DNA fragment encoding amino acids 1-166 and the Such-NotI fragment encoding amino acids 167-298 were isolated and ligated into the previously digested expression vector pST239, a pBR322-derived vector containing an N-terminal polyhis leader at the 3' end of which is an NsiI restriction site. The resulting LIV-1 ECD expression plasmid was designated pE164647.

Transcriptional and translational control of expression in the ST239 vector were provided by the following genetic features. Transcriptional initiation was controlled by the *E. coli* alkaline phosphatase promoter (Kikuchi Y. at al., Nucleic Acids Res. 9:5671-5678 (1981)). The trp operon ribosome binding site was used for translation initiation (Yanofsky C. et al., Nucleic Acids Res. 9:6647-6668

(1981)). Translational termination was effected by the translation termination codon and the downstream λto transcriptional terminator (Scholtissek S. et al., Nucleic Acids Res. 15:3185 (1987)), followed by the rare codon tRNA genes pro2, argU, and glyT (Komine Y., et al., J. Mol. Biol. 212:579-598(1990), Fournier M. J., et al. Microbiol. Rev. 49:379-397 (1985)).

To facilitate expression, the extracellular domain of LIV-1 was expressed in *E. coli* cytoplasm with a N-terminal poly-histidine leader sequence encoded within the ST239 expression vector. The amino acid sequence of this leader was: MK HQHQHQHQHQHIQMHQ (SEQ ID NO:111) This leader sequence offered several advantages. First, translation initiation was optimized. In addition, purification was simplified by adsorption on a nickel chelation column. Finally, the leader sequence was easily and efficiently removed, as desired, using the TAGZyme™ system (Unizyme Laboratories, Horsholn, Denmark).

Following construction of the expression plasmid, pE164647, and DNA sequence verification, the LIV-1 expression plasmid was transformed into the *E. coli* strain 58F3 (fhuAΔ(tonAΔ)tonΔ galE rpoHts(hipRts)ΔclpP lacIq ΔompTΔ(nmpc-fepE)ΔslyD). Transformants were initially cultured in Luria broth at 30° C. overnight, and then diluted 100-fold into a phosphate-limiting media to induce the alkaline phosphatase promoter. After 24 hours at 30° C. with shaking, the cultures were centrifuged, and the cell pastes frozen until the start of purification.

Purification of LIV-1 ECD

A 0.5 liter fermentation of *E. coli* transformants expressing LIV-1 yielded approximately 6-10 grams of cell paste. The paste was resuspended in 10 volumes (w/v) of 7 M guanidine, 20 mM Tris, pH 8 buffer. Solid sodium sulfite and sodium tetrathionate were added to make final concentrations of 0.1 M and 0.02 M. respectively, and the solution was stirred overnight at 4° C. This sulfitolysis step resulted in a denatured protein having all cysteine residues blocked. The solution was centrifuged at 40 K rpm in a Beckman ultracentifuge for 30 min. The supernatant was diluted with 3-5 volumes of metal chelate column buffer (6 M guanidine, 20 mM Tris. pH 7.4) and filtered through 0.22 micron filters to clarify. A volume corresponding to 50 mls of the clarified extract was loaded onto a 5 ml Qiagen Ni-NTA (nickel-nitrilotriacetic acid) metal chelate affinity column equilibrated in the metal chelate column buffer (QIAexpress® Protein Purification System, Qiagen, Valencia, Calif. USA). The column was washed with additional buffer containing 50 mM imidazole (Calbiochem, Utrol grade), pH 7.4. The protein was eluted with buffer containing 250 mM imidazole. Fractions containing the desired protein were pooled and stored at 4° C. Protein concentration was estimated by its absorbance at 280 nm using the calculated extinction coefficient based on its amino acid sequence. Protein for antibody production was obtained by reducing an aliquot of the Ni-NTA pool with dithiothreitol (50 mM final concentration) followed by extensive dialysis against 1 mM HCl.

Development of Monoclonal Antibodies to LIV-1 Protein

Monoclonal antibodies specific for the extracellular domain of LIV-1 were developed according to the following procedures.

Ten Balb/c mice (Charles River Laboratories, Wilmington, Del.) were hyperimmunized with recombinant polyhistidine-tagged human LIV-1 isolated from pE164647-transformed *E. coli* as described herein. The tagged LIV-1 protein in Ribi adjuvant (Ribi Immunochem Research, Inc., Hamilton, Mo.) was administered to the mice. B-cells from five mice demonstrating high anti-LIV-1 antibody titers were fused with mouse myeloma cells (X63.Ag8.653; American Type Culture Collection, Rockville, Md.) using a modified protocol analogous to one previously described (Kohler. G. and Milstein, C., Nature 256: 495-497 (1975): Hongo, J. S. et al., Hybridoma 14:253-260 (1995)).

After 7-14 days, the supernatants were harvested and screened for antibody production and LIV-1 binding specificity by standard techniques using direct enzyme-linked immunosorbent assay (ELISA). Sixteen positive clones, showing the highest immunobinding affinity after the second round of subcloning by limiting dilution, were injected into Pristane-primed mice (Freund, Y. R. and Blair, P. B., *J. Immunol.* 129:2826-2830(1982)) for in vivo production of monoclonal antibody. The ascites fluids from these mice were pooled and purified by Protein A affinity chromatography (Pharmacia fast protein liquid chromatography (FPLC) Pharmacia, Uppsala, Sweden) as previously described (Hongo, J. S. et al., Hybridoma, supra (1995)). The purified antibody preparations were sterile filtered (0.2-μm pore size; Nalgene, Rochester N.Y.) and stored at 4° C. in phosphate buffered saline (PBS).

Expression of LIV-1 ECD Fragments in *E. coli*

Fragments of the LIV-1-164647 ECD were expressed in *E. coli* using the same techniques as described for cloning and expressing the full length LIV-1-164647. The expressed ECD fragments were the N-terminal fragment (amino acid 1 to and including amino acid 147 of SEQ ID NO:4) and the C-terminal fragment (amino acid 148 to and including amino acid 298 of SEQ ID NO:4). The fragments were purified as described above.

Standard Western blot analysis was used to determine which of the N-terminal or C-terminal ECD fragments bound to monoclonal antibodies isolated as described above. Only monoclonal antibodies 2945, 2982, 2984, 2985, 2987, and 2988 were tested. It was found that monoclonal antibody 2984 bound to the N terminal fragment, while monoclonal antibody 2945, 2982, 2985, 2987, and 2988 bound to the C-terminal fragment. The results are listed in Table 3.

Expression of Exogenous Full-Length LIV-1 in Mammalian Cells

Each of the 16 antibodies listed in Table 3 was examined for binding to the ECD of LIV-1-164647 and found to bind specifically. The antibodies were characterized to have the properties listed in Table 3. Epitope characterization involved determination as to whether a test antibody can compete for binding to the same epitope as the epitope bound by an anti-LIV-1-164647 antibody of the present invention, including the antibodies produced by the hybridomas deposited with the ATCC, using a cross-blocking (e.g., a competitive ELISA assay) can be performed. In an exemplary competitive ELISA assay, LIV-1-167647 or its ECD (or other fragment) coated on the wells of a microtiter plate is pre-incubated with or without candidate competing antibody and then the biotin-labeled anti-LIV-1-164647 antibody of the invention is added. The amount of labeled anti-LIV-1-164647 antibody bound to the LIV-1 antigen in the wells is measured using avidin-peroxidase conjugate and appropriate substrate. The antibody can be labeled with a radioactive or fluorescent label or some other detectable and measurable label. The amount of labeled anti-LIV-1 antibody bound to the antigen has an indirect correlation to the ability of the candidate competing antibody (test antibody) to compete for binding to the same epitope (i.e., the greater the affinity of the test antibody for the same epitope, the less of the labeled antibody will be bound to the antigen-coated wells). A candidate competing antibody is considered an antibody that binds substantially to the same epitope or that competes for binding to the same epitope as an anti-LIV-1 antibody of the invention if the candidate antibody can block binding of the LIV-1 antibody by at least 20%, preferably by at least 20-50%, even more preferably, by at least 50% as compared to the control performed in parallel in the absence of the candidate competing antibody (but may be in the presence of a known non-competing antibody). It will be understood that variations of this assay can be performed to arrive at the same quantitative value. The epitope group assignment for each antibody in Table 3 was determined by competitive ELISA. Each antibody was biotinylated and tested for binding to LIV-1-164647 ECD coated on plates in the presence or absence of an excess of each unlabeled anti-LIV-1-164647 monoclonal antibody. Streptavidin-HRP was then added to the plates followed by peroxidase substrate. A decrease in the binding by at least 50% or a lack of binding of biotinylated monoclonal antibodies to LIV-1-164647 ECD indicated that both unlabeled and biotinylated antibodies bound to the same (or proximal) epitope on LIV-1-164647.

Expression of full-length LIV-1 in mammalian cells resulted in the exposure of the extracellular domain on the surface of the cells. To demonstrate this, 3T3 cells were transiently transfected with an expression construct encoding wild-type full length LIV1646471 (pRK5-LIV-1-164647). Control cells were transfected with the pRK5 vector lacking the LIV-1 insertion. After 24 hours, cells were analyzed for cell surface expression by fluorescent activated cell sorting (FAGS) analysis using the anti-LIV-1-164647 ECD monoclonal antibody, described herein, as a tag. Approximately 106 cells were incubated for 30 min on ice in PBS containing 2% Goat serum and 5% Rabbit serum (FAGS buffer) then for 2 hours in FAGS buffer containing 1 µg/ml of anti-LIV-1-164647 ECD monoclonal antibody 2982 (isolated from hybridoma 2982.4A12.1E8.1C4, designated ATCC PTA-2962) or anti-LIV-1-164647 ECD monoclonal antibody 2983 (isolated from hybridoma 2983.3G9.1D4.1D7, ATCC PTA-2963). The cells were then washed with ice cold PBS, incubated for 20 minutes at 4 0C with a Biotin-conjugated Goat anti-human IgG second antibody (Jackson Immunoreagents; West Grove, Pa.), washed before incubation for 20 mm at 4° C. with phycoerythrin conjugated streptavidin (Jackson Immunoreagents; West Grove, Pa.). Cells were washed again prior to cytofluorometry. The FAGS analysis results using antibody 2983 are plotted in FIG. 6. The results demonstrated that cell surface expression of LIV-1-164647 was detected in 3T3 cells transfected with pRK5- LIV-1-164647, but not in control (pRK5 vector only) cells. Thus, amino acids 1-298 of the LIV-1-164647 protein constitute an extracellular domain.

Expression of Endogenous LIV-1 in a Breast Tumor Cell Line

It is disclosed herein that endogenous LIV-l is expressed on the surface of cells of the MCF-7 breast tumor cell line (ATCC HTB-22, for example). Anti-LIV-1 monoclonal antibody 2945 (from hybridoma 2945.2G1.1C7.2F10; ATCC PTA-2961) was radiolabeled with $^{125}$I using the lactoperoxidase method. MCF-7 cells were harvested with PBS containing 1 mM EDTA. A population of 3.4 million MCF-7 cells were incubated in PBSA (PBS+0.1% BSA+0.02% azide) with 50,000 cpm (230 pM) of $^{125}$I-2945 in the presence (NSB) or absence (Tot) of an excess of unlabeled antibody (0.25 µM) for 1 h at room temperature. Bound radioactivity was then separated from unbound radioactivity by centrifugation for S mm at 5000 rpm over a 1ml cushion of 20% sucrose in cold PBS. Radioactivity associated with the cell pellet was then counted in a gamma counter. As shown in FIG. 7, specific binding of anti-LIV-1-164647 monoclonal antibody 2945 was detected at the surface of MCF-7 cells indicating that endogenous LIV-l is expressed at the cell surface in this breast tumor cell line.

Antibody Binding to LIV-1

Selected monoclonal antibodies of the present invention and their respective hybridomas are listed in Table 3. Characterization of the monoclonal antibodies was performed as described herein using standard techniques of competition binding for epitope analysis, cell sorting for FACS analysis, and Western blotting for determining whether the antibody hound to the N-terminal or C-terminal portion of the LIV-1-164647 ECD.

TABLE 3

L1V-1-Binding Monoclonal Antibodies

| Monoclonal Antibody | Hybridoma Cell Line | Isotype | Epitope Group[a] | FACS (3T3-LIV-1/3T3) | ECD fragment N- or C-terminal[b] |
|---|---|---|---|---|---|
| 2945 | 2G1.1C7.2F10 | IgG2b | A | +++/− | C-terminal |
| 2982 | 4A12.1E8.1C4 | IgG1 | A | +++/− | C-terminal |
| 2983 | 3G9.1D4.1D7 | IgG1 | A | +++/− | not tested |
| 2984 | 6D6.1H10.2C1 | IgG1 | C | +++/− | N-terminal |
| 2985 | 4F3.2D6.1D7 | IgG1 | A | +/− | C-terminal |
| 2987 | 1D8.1C11.2B7 | IgG1 | C | ++/− | C-terminal |
| 2988 | 1A7.1F2.1H7 | IgG1 | A | +/− | C-terminal |
| 2946 | 2B11.2B11.2A12 | IgG2b | B | −/− | not tested |
| 2947 | 3H8.2D9.1H8 | IgG1 | B | ++/− | " |
| 2948 | 2G4.2C7.2D6 | IgG2b | B | −/− | " |
| 2949 | 5B4.2H11.1G10 | IgG2b | B | −/− | " |
| 2950 | 5H5.2A7.1D8 | IgG2b | B | −/− | " |
| 2951 | 4G3.2F8.2A11 | IgG2b | B | ++/− | " |
| 2952 | 6G9.1G9.1A10 | leG2b | B | −/− | " |
| 2953 | 6B6.2E11.1F10 | IgG1 | B | +/− | " |
| 2986 | 1F1.2G8.2E7 | IgG1 | B | −/− | " |

[a]Epitope group assignments were made by antibody competition analysis as described herein.
[b]The term "N- or C-terminal" refers to binding of the tested antibody to the N-terminal or C-terminal fragment of the LIV-1-164647 ECD, where the N-terminal fragment was amino acid 1-147 of SEQ ID NO:4, and the C-terminal fragment was amino acids 148-298 of SEQ ID NO:4.

Deposit of some of these hybridomas with the American Type Culture Collection under the Budapest Treaty is described herein under the heading "Deposit of Material."

Example 5

LIV-1 Expression in Tumor Tissue Examined by RNA in Situ Hybridization

This example provides methods used in the preparation of tissue arrays for the determination of LIV-1 expression in various human tissues (see, for example, Kononen, J., et al. Nature Medicine 4:844-847 (1998)).

Preparation of Tissue Microarrays

A tissue microarray, or tissue array, is a paraffin block containing several individual tissue samples. A typical tissue microarray may contain 1000 or more samples. Tissue microarrays allow the examination of a large series of specimens while maximizing efficient utilization of technician time, reagents, and valuable tissue resources.

Tissue microarrays are constructed by first removing small cores (0.6 mm diameter. 3-4 mm height) from "donor" tissue biopsy samples embedded in paraffin blocks using a tissue array instrument (Beecher Instruments, Silver Spring, Md., USA). Using the same instrument, each core sample is then re-embedded, together with other biopsy cores, in a single "recipient" block to form an array. Preferably, each tissue is sampled in triplicate. Thin slices (4-8 µm thick) of a recipient block were mounted on glass slides. Visualization and screening, may be performed by histological methods including, but not limited to, standard hematoxylin and cosin staining for morphological analysis; immunohistochemistry (IHC) for protein detection; mRNA in situ hybridization (mRNA ISH) and RT-PCR for mRNA detection; fluorescence in situ hybridization (FISH) and in situ PCR for DNA detection; and terminal deoxynucleotidyl transferase (TdT)-mediated dUTP nick-end labeling (TUNEL) assay for detection of cells undergoing apoptotic DNA fragmentation.

The followings mRNA ISH procedures were used to determine a human tissue expression profile for LIV-1.

In Situ Hybridization

In situ hybridization is a powerful and versatile technique for the detection and localization of nucleic acid sequences within cell or tissue preparations. It may be useful, for example, to identity sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1: 169-176 (1994), using PCR-generated $^{33}$P-labeled riboprobes. Briefly, formalin-fixed, paraffin-embedded human tissues were sectioned, deparaffinized, deproteinated in proteinase K (20 µg/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

Preparation of DNA Template

For synthesis of a LIV-1-specific riboprobe, template DNA corresponding to a portion of LIV-1 was needed. To that end, a portion of the DNA 164647 (LIV-1-164647) nucleic acid sequence from nucleotide 1690-nucleotide 2240 (SEQ ID NO:3; see FIG. 2A) having the following sequence was amplified for use as template DNA: 5'-TGC-CATTCAC ATTTCCACGA TACACTCGGC CAGTCA-GACG ATCTCATTCA CCACCATCAT GACTACCATC ATATTCTCCA TCATCACCAC CACCAAAACC ACCATCCTCA CAGTCACAGC CAGCGCTACT CTCGGGAGGA GCTGAAAGAT GCCGGCGTCG CCACTTTGGC CTGGATGGTG ATAATGGGTG ATG-GCCTGCA CAATTTCAGC GATGGCCTAG CAATTG-GTGC TGCTTTTACT GAAGGCTTAT CAAGTGGTTT AAGTACTTCT GTTGCTGTGT TCTGTCATGA GTTGC-CTCAT GAATTAGGTG ACTTTGCTGT TCTACTAAAG GCTGACATGA CCGTTAAGCA GGCTGTCCTT TATAATGCAT TGTCAGCCAT GCTGGCGTAT CTTG-GAATGG CAACAGGAAT TTTCATTGGT CATTAT-GCTG AAAATGTTTC TATGTGGATA TTTGCACTTA CTGCTGGCTT ATTCATGTAT GTTGCTCTGG TTGATATGGT ACCTGAAATG CTGCACAATG ATGCTAGTGA CCATGGATGT AGCCGCTGGG G-3' (SEQ ID NO:12). The amplified DNA was used as the template from which a radiolabeled riboprobe was synthesized for in situ hybridization.

Primers used for generating an antisense cDNA strand of LIV-1 from template nt 1690 nt 2240:

Primer F-99104: 5'-GGA TTC TAA TAC GAC TCA CTA TAG GGC TGC CAT TCA CAT TTC CAC GAT-3' (SEQ ID NO:13).

Primer F-99105: 5'-CTA TGA AAT TAA CCC TCA CTA AAG GGA CCC CAG CGC CTA CAT CC-3' (SEQ ID NO:14).

The Advantage cDNA polymerase mix from Clonetech (8417-1) was used according to the manufacturer's directions with slight modifications. Briefly, 316 µl SQ water (highly purified, RNase-free water), 40 µl 10×PCR buffer, 16 µl 10 mM dNT), 8 µl primer SEQ ID NO:13, 8 µl primer SEQ ID NO:14 were combined to form a master mixture. From the master mixture, 97 µl were aliquoted into a PCR tube followed by the addition of 2 µl of template DNA and 1 µl of Advantage cDNA polymerase. Using a Perkin-Elmer Cetus 9600 thermocycler, cycle conditions were as follows:

Begin: 85° C., 5 minutes
  60° C., 1.5 minutes
10 cycles of:
94° C. 30 seconds
68° C. 30 seconds
72° C. 1 minutes
15 cycles of:
94° C. 30 seconds
55° C. 30 seconds
72° C. 1 minutes
followed by:
72° C. 7 minutes
4° C. hold Upon completion of the PCR cycles, the PCR product was filter through a Microcon-50™ filter unit to remove primers and excess buffer.

LIV-1 $^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

2.0 µl 5× transcription buffer
10 µl DTT (100 mM)
2.0 µl NTP mix (2.5 mM; 10 µl; each of 10 mM GTP, CTP & ATP+10 µl H$_2$O)
1.0 µl Rnasin ribonuclease inhibitor
3.0 µl DNA template (1 µg) in H$_2$O
1.0 µl RNA polymerase (for PCR products T3=AS (antisense), T7=S (sense), usually)

The tubes were incubated at 37° C. for one hour, 1.0 µl RQ1 DNase was added followed by incubation at 37° C. for 15 minutes, 90 µl TE (10 mM Tris pH 7.6/1 mM EDTA pH 8.0) were added, and a 1.0 µl aliquot of the mixture was pipetted onto DE81 paper. The remaining solution was loaded in a Microcon-50 ultrafiltration unit (Amicon, 42416), and spun 6 minutes using program 10 of a Heraeus Centrifuge 28RS. The filtration unit was inverted over a second tube and spun for 3 minutes using program 2. After the final recovery spin, 100 µl TE were added, 1 µl of the final product was pipetted on DE81 paper. The samples dotted onto DE81 paper before and after filtration were counted in 6 ml of Biofluor II in a Beckman LS 5000TD scintillation counter.

To verify its size, the probe was run on a TBE/urea gel. 1-3 µl of the filtered probe or 5 µl of RNA Molecular Weight Marker III (Boehringer Mannheim) were added to 3 µl of loading butter. After heating on a 37° C. heat block for three minutes, the probes were immediately placed on ice. The wells of gel were flushed, the samples loaded, and run at 180-250 volts for 45 minutes. The gel was wrapped in saran wrap and exposed to Biomax MS™ film or XAR-2™ film (Kodak) with an intensifying screen in –70° C. freezer one hour to overnight. The LIV-1 riboprobe thus prepared was designated 764 AS or 764 S for the antisense and sense probes, respectively.

$^{33}$P-Hybridization

Pretreatment of paraffin-embedded sections: The thin slices of a recipient tissue array block mounted on glass slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer) at 37° C. for 15 minutes). Slides were subsequently rinsed in 0.5×SSC, dehydrated through graded ethanols (70%, 95%, and 100%) for 2 minutes at each grade, and air-dryed.

Prehybridization: The slides were laid out in plastic box lined with Box buffer (4×SSC, 50% formamide)—saturated filter paper. The tissue was covered with 100 µl of hybridization buffer (10% (Dextran Sulfate, 50% formamide, 1×SSC) and incubated at 42° C. for 1-4 hours.

Hybridization: 2.0×10$^6$ cpm probe and 2.0 µl tRNA (100 mg/ml stock) per slide were heated at 95° C. for 3 minutes. The slides were cooled on ice, and hybridization buffer was added to make a final volume of 100 µl per slide. After vortexing, 100 µl $^{33}$P mix were added to 100 µl prehybridization on slide. The slides were incubated overnight at 55° C.

Washes: Washing was done 2×10 minutes with 2×SSC, EDTA at room temperature (400 ml 20×SSC+16 ml 0.25M EDTA, V$_f$=4L), followed by Rnase treatment at 37° C. for 30 minutes (500 µl of 10 mg/ml in 250 ml prewarmed Rnase buffer=20 µg/ml). The slides were washed 2×10 minutes with 2×SSC, EDTA at room temperature. The stringency wash conditions were as follows: 4×30 minutes at 55° C., 0.1×SSC, EDTA (20 ml 20×SSC+16 ml EDTA, V$_f$=4L). This was followed by 2×10 minute washes 0.5SSc at RT. The slides were then dehydrated for 2 minutes at each of 50%, 70%, 90% ethanol contain 0.3 M ammonium acetate, and air dried for 2 hours. The dried slides were exposed to Biomax MS film (Kodak) for 16 hours or Hyperfilm β-Max film (Amersham) over 2 days.

ErbB2 and β-actin $^{33}$P-Riboprobe Synthesis

For comparative analysis of LIV-1 and ErbB2 expression by RNA in situ hybridization, a riboprobe complementary to an ErbB2 nucleic acid sequence was prepared. As a control, expression of β-actin was also monitored using a riboprobe complementary to the RNA of that gene.

Using the procedures just disclosed, riboprobes specific for ErbB2 and β-actin were also prepared. The ErbB2 riboprobe was synthesized by transcription from a DNA template having the following sequence, 5'-TGGTCGTGGT CTTGGGGGTG GTCTTTGGGA TCCTCATCAA GCGACGGCAG CAGAAGATCC GGAAGTACAC GAT-GCGGAGA CTGCTGCAGG AAACGGAGCT GGTG-GAGCCG CTGACACCTA GCGGAGCGAT GCCCAAC-CAG GCGCAGATGC GGATCCTGAA AGAGACGGAG CTGAGGAAGG TGAAGGTGCT TGGATCTGGC GCTTTTGGCA CAGTCTACAA GGGCATCTGG ATC-CCTGATG GGGAGAATGT GAAAATFCCA GTGGC-CATCA AAGTGTTGAG GGAAAACACA TCCCCCAAAG CCAACAAAGA AATCTTAGAC GAAGCATACG TGATGGCTGC TGTGGGCTCC CCATATGTCT CCCGCCTTCT GGGCATCTGC CTGA-CATCCA CGGTGCAGCT GGTGACACAG CTTATGC-CCT ATGGCTGCCT CTTAGACCAT GTCCGGGAAA ACCGCGGACG CCTGGGCTCC CAGGACCTGC TGAACTGGTG TATGCAGATT GCCAAGGGGA TGAGCTACCT GGAGGATGTG CGGCTCGTAC ACAGGGACTT GGCCGCTCGG AACGTGCTGG TCAAGAGTCC CAACCATGTC AAAATTACAG ACT-TCGGGCT GGCTCGGCTG-3' (SEQ ID NO:15), and its complement. The template also included a T7 and T3 promoter. The resultant ErbB2 specific antisense riboprobe was designated "442 AS."

The β-actin riboprobe was synthesized by transcription from a DNA template having the following sequence, 5'-GCTGCCTGAC GGCCAGGTCA TCACCATTGG CAATGAGCGG TTCCGCTGCC CTGAGGCACTCTTC-CAGCCT TCCTTCCTGG GCATGGAGTC CTGTG-GCATC CACGAAACTA CCTTCAACTC CATCATGAAG TGTGACTGTG ACATCCGCAA AGACCTGTAC GCCAACACAG TGCTGTCTGG CGGCACCACC ATG-TACCCTG GCATTGCCGA CAGGATGCAG AAG-GAGATCA CTGCCCTGGC ACCCAGCACA ATGAA-GATCA AGATCATTGC TCCTCTGAGC GCAAGTACTC-3' (SEQ ID NO:16), and its complement. The template included a T3 promoter. The resultant β-actin-specific antisense riboprobe was designated "117 AS."

Detection of LIV-1 in Tissue by RNA in Situ Hybridization

This example provides results from tissue array analyses in which the expression of LIV-1 in various tissues was examined. Briefly, LIV-1 expression was found to occur in fetal kidney epithelium, developing fetal spinal ganglia including enteric plexuses, fetal brain, adult prostatic epithelium, breast tumors, breast fibroadenomas, lung carcinoma, squamous lung, colon carcinoma, prostate carcinoma, endometrial carcinoma, ovarian carcinoma, and melanoma.

Table 4 provides the results of several tissue microarray RNA in situ hybridization analyses. Unless otherwise indicated, the tissue microarrays were prepared as described herein. The tabulated results and comments were generated in studies designated IS2000-060 and IS2000-084 in which tissue microarrays were given section numbers merely for internal reference. The relative expression of LIV-1 is indicated as "+", "++", or "+++" for increasing levels of detection, whereas no detectable expression was indicated as "–." The LIV-1 riboprobes used for RNA in situ hybridization were designated "764 S" as the sense probe and "764

AS" as the antisense probe. Antisense riboprobes specific for ErbB2 (probe 442 AS) and β-actin (probe 117 AS, as control) transcripts were also used in the IS2000-084 study.

As used herein, the term "TMA" refers to tissue microarray. The term "NMA" refers to normal tissue microarray, where "normal" refers to non-cancerous tissue.

TABLE 4

Tissue Expression of LIV-1 by RNA in situ Hybridization

| Tissue | Section[c] | Probe[a] | Result | Comments |
|---|---|---|---|---|
| Study ISH2000-060 | | | | |
| Control Cell Pellet | H2000-219.01 | 764 AS | − | |
| Control Cell Pellet | " | 764 S | − | |
| LIV-1 Cell Pellet | H2000-219.02 | 764 AS | +++ | |
| LIV-1 Cell Pellet | " | 764 S | + | |
| Various, rhesus & human | Misc. 02 | 764 AS | − | |
| Various | Misc. 02 | 764 S | − | |
| 12 wk Placenta | H97-039.02 | 764 AS | − | |
| 12 wk Placenta | " | 764 S | − | |
| 14.5 wk Fetus | H97-106.31 | 764 AS | ++ | Expression in fetal kidney epithelium, developing spinal ganglia, including enteric plexuses |
| 14.5 wk Fetus | " | 764 S | − | |
| Fetal Brain | H97-045.01 | 764 AS | + | Expression over fetal cortical neurons |
| Fetal Brain | " | 764 S | − | |
| Fetal Brain | H97-106.36 | 764 AS | + | |
| Adult NMA | H2000-165.06 | 764 AS | ++ | Strong expression over prostatic epithelium, focal low level expression over renal tubules, lung, gall bladder, spleen, heart and pancreas negative. |
| Adult NMA | " | 764 S | − | |
| Breast TumorTMA | H2000-94B | 764 AS | ++ | Expression elevated in 5 of 13 breast cancers; highly expressed in fibroadenomas |
| Tumor Block 3 | H2000-165.20 | 764 AS | − | |
| Lung Tumor TMA | H1999-637 | 764 AS | + | Expression in one carcinoma and low level expression observed in normal bronchial epithelium |
| Lung Tumor TMA[b] | H2000-27 | 764 AS | ++ | Poor quality array, 6 cancers show moderate to high expression |
| Colon Tumor TMA | H1999-636 | 764 AS | + | Relative to breast, low level expression in 4 carcinomas |
| Colon Tumor TMA[b] | H2000-26 | 764 AS | − | Poor quality array |
| Breast Tumor TMA | H1999-635 | 764 AS | ++ | Expression observed in 3 carcinomas: highest levels seen in a case of fibroadenoma and one of sclerosing adenosis |
| Prostate Tumor TMA[b] | H2000-25 | 764 AS | ++ | At least 18 of the cases show reasonable signal; there is a reasonably strong signal in normal prostate |
| Human NMA | H2000-2 | 764 AS | + | Low level signal over adrenal cortex and renal tubular epithelium |
| Breast NMA | HP001595 | 764 AS | ++ | Expressed on nipple skin epithelium[d], breast ductal epithelium and acinar epithelium |
| Chimp NMA | H2000-185 | 764 AS | + | Expression over squamous epithelium |
| Multi-Tumor TMA | H2000-132 | 764 AS | + | Elevated expression in squamous lung, transitional, endometrial, ovarian carcinomas and melanoma |

TABLE 4-continued

Tissue Expression of LIV-1 by RNA in situ Hybridization

| Tissue | Section[c] | Probe[a] | Result | Comments |
|---|---|---|---|---|
| Study IS2000-084 | | | | |
| Breast Tumor TMA | H2000-94 | 764 AS | | Positive for LIV-1 mRNA |
| | — | 442 AS | | Positive for ErbB2 mRNA |
| | " | 117 AS | | Positive for β-actin mRNA |

[a]Riboprobe preparation and number designations are disclosed in this Example.
[b]Array purchased from Clinomics Biosciences, Inc., Pittsfield, MA.
[c]Several of the sections listed in Table 4 contained various tissue types. For example, section Misc. 02 contained normal (i.e. non-cancerous) kidney, bladder, lung, and end stage renal disease (non-cancerous). Tumor block 3 (H2000-165.20) contained chondrosarcoma, osteosarcoma, renal cell carcinoma, liposarcoma, gastric adenocarcinoma, squamous carcinoma, and brain tumor. Human NMA (H2000-2) contained samples of pancreas, adrenal, heart, eye, small intestine, kidney, spleen, lymph node, tonsil, skin, breast, lung, brain, colon, liver, aorta, placenta, stomach, ovary, prostate, breast, and skin. All lymph node specimens on H2000-2 were actin negative suggesting that mRNA was degraded in these samples, whereas heart samples were only weakly actin positive). Breast TMA (section H2000-94B) contained samples of atypical periductal stromal proliferation (previous excision of cystosarcoma), reactive changes with giant cells: DCIS (0 of 4 lymph node (LN) positive): Ductal carcinoma. invasive; Ductal carcinoma. poorly-differentiated. invasive (0 of 24 LN positive): Atypical hyperplasia/CIS: Carcinoma with ductal and lobular features. infiltrative. lymph node metastasis; Ductal carcinoma. invasive.g-rade III/III: DCIS. low grade: LCIS (0 of 26 LN pos); Benign breast tissue: Fibroadenoma: Adenocarcinoma. invasive (31 of 31 LN pos): Adenosis. Multi tumor TMA (section H2000-132) contained samples from lung tumor (bronchioloalveolarcarcinoma. adenocarcinoma): colon adenocarcinoma: gastric adenocarcinoma: pancreatic ductal adenocarcinoma: heptocellular carcinoma: prostate adenocarcinoma (Gleason grade 2-3):bladder transitional cell carcinoma: kidney papillary transitional cell carcinoma: prostate transitional cell carcinoma: renal clear cell carcinoma: endometrial adenocarcinoma: ovary papillary adenocarcinoma: ovary clear cell adenocarcinoma: lymphoma: and melanoma.
[d]Quantitative microarray analysis of extracted mRNA from cells of a different sample of normal breast skin indicated low LIV-1 expression in skin relative to breast tumor.

As the results of Study IS2000-060 in Table 4 indicate, RNA in situ hybridization confirms elevated expression of LIV-1 in some breast cancers relative to normal breast; expression was elevated in 5 of 13 breast cancers in a TMA. High expression was also seen in benign breast disease, specifically fibroadenomas and sclerosing adenosis. Strong expression was observed in normal prostatic epithelium as well as in prostate cancers. Expression was seen in epithelium of a number of other tumor types including: squamous lung, transitional, endometrial, ovarian carcinomas and melanoma. With regard to expression in normal tissue, LIV-1 is moderately to highly expressed in normal squamous epithelium (e.g., chimp and human breast skin). Strong expression was observed over normal prostatic epithelium, focal low level expression over normal renal tubules. Liver, lung, gall bladder, spleen, heart, and pancreas were all negative for LIV-1 RNA expression. In fetus, expression was seen in fetal kidney epithelium as well as in developing spinal ganglia, including enteric plexuses and fetal brain.

In Study IS2000-084, the relative expression of RNA of β-actin (as control), ErbB2, and LIV-1 in breast tumor were compared. The results are shown in Table 4. All samples exhibited adequate expression of β-actin RNA. Weak to moderate expression of ErbB2 (HER2) RNA was seen in benign and malignant epithelial cells of most cases. Particularly strong expression was seen in four cases, three cases of infiltrating ductal carcinoma, and one case of ductal carcinoma in situ (DCIS). LIV-1 RNA was observed in the benign and malignant mammary epithelial cells in most cases at an intensity ranging from weak to strong, with most cases showing a moderate level of expression. There was no indication in the tissues sampled for this study that LIV-1 was up-regulated in the malignant cells compared to benign cells.

Example 6

Detecting LIV-1 Expression in Cells

Diagnosis of breast tumor tissue as the type that overexpresses LIV-1 but does not simultaneously express ErbB2 is useful to allow the physician to tailor the patients tumor therapy.

Detection of LIV-1-164647 expression and ErbB2 expression in breast tumor (or any tumor or other cells) is readily performed by microarray technology, as described in Example 1, coupled with ordinary knowledge of relevant microarray technology procedures.

Detection of LIV-1-164647 expression in a cell may be performed by in situ hybridization, where the probe for detecting is derived from the ECD of LIV-1-164647 and is a cDNA or a RNA having a sequence that hybridizes under stringent conditions to a sequence from nucleotide 412 to and including nucleotide 477 of SEQ ID NO:3 or its complementary sequence. Preferably, the probe hybridizes to a sequence from nucleotide 446 to and including nucleotide 464 of SEQ ID NO:3 or its complementary sequence. Hybridization protocols useful for this method of detection are standard in the relevant literature. A non-limiting RNA its useful hybridization technique useful for detecting LIV-1-164647 expression is disclosed herein.

Alternatively, relative expression of LIV-1 and ErbB2 is performed by contacting an anti-LIV-1-164647 antibody of the invention that specifically binds to the extracellular domain of LIV-1-164647 protein and comparing the amount of detectable binding with control cells that do not express LIV-1-164647 protein; with cells (such as SKBR3 cells) that overexpress ErbB2, but do not overexpress LIV-1-164647, and with cells (such as cells expressing LIV-1 or DNA 164647) that overexpress LIV-1-164647 but do not overexpress ErbB2, wherein overexpression is determined as at least 1.5-fold greater expression in a cell from tumor tissue relative to expression in a cell from non-cancerous tissue. The techniques for binding anti-LIV-1 antibody and/or anti-ErbB2 antibody are readily determined based on disclosure provided herein coupled with ordinary skill in the art of cell surface protein detection. Preferably, the antibody used for detecting expression of the LIV-1-164647 polypeptide binds to the ECD of LIV-1-164647, preferably binding to epitope A, epitope B, or epitope C of an LIV-1 ECD, preferably the LIV-1-164647 ECD. Alternatively the antibody used for detecting expression of an LIV-1 polypeptide binds to a polypeptide comprising an amino acid sequence from amino acid 114 to and including amino acid 135 of SEQ ID NO:4, more preferably comprising a sequence from amino acid 126 to and including 132 of SEQ ID NO:4. Antibodies useful for practicing this method are described herein and include without limitation the monoclonal antibodies produced by one or more of the hybridomas ATCC _____ (LIV-1.2945.2G1.1C7.2F10); ATCC _____ (LIV-1.2982.4A12.1E8.1C4); ATCC _____ (LIV-1.2983.3G9.1D4.1D7); ATCC _____ (LIV-1.2984.6D6.1H10.2C1); ATCC _____ (LIV-1.2985.4F3.2D6.1D7); ATCC _____ (LIV-11.2987.1 D8.1C11.2B7); and ATCC _____ (LIV-1.2988.1A7.1F2.1H7). Techniques useful for performing antibody binding studies are disclosed herein and are found in the relevant literature.

Example 7

Pharmaceutical Formulations

Antibodies specifically binding a LIV-1 polypeptide of the invention, or a fragment of the LIV-1 polypeptide, such as the ECD, which may be identified by the screening assays disclosed herein, can be administered for the treatment of tumors, including cancers, in the form of pharmaceutical compositions.

Where antibody fragments are used, the smallest inhibitory fragment which specifically hinds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]). If the antibody that binds a LIV-1 protein binds to an intracellular portion, and whole antibodies or fragments are used as inhibitors, internalizing the antibodies is preferred. Lipofections or liposomes can be used to deliver the antibody, or an antibody fragment, into cells.

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride, hexamethonium chloride; benzalkonium chloride, benzethonium chloride; phenol, butyl or benzyl alcohol; alkyl parabens such as methyl or propyl paraben, catechol; resorcinol, cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysing; monosaccharides, disaccharides, and other carbohydrates including glucose, mannose, or dextrins; chelating agents such as EDTA, sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide antibodies which bind to vascular endothelial factor (VEGF) in the one formulation. Alternatively, or in addition, the composition may comprise a cytotoxic agent, cytokine or growth inhibitory agent, provided that the cytotoxic agent is other than an anthracycline derivative, e.g. doxorubicin, or epirubicin. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules, Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or acetate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Example 8

Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for detecting (e.g. diagnosing) or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g. an antibody. The label on, or associated with, the container indicates that the composition is used for diagnosing or treating the condition of choice. The article of manufacture may further comprise a second container comprising a pharmaceutically acceptable buffer, such as phosphate buffered saline, Ringer's solution and dextrose solution. It may further include other materials desirable from a commercial and user standpoint, including other buffers, diluents, filters, needles, syringes, and package inserts with instructions for use.

Example 9

Diagnosis and Prognosis of Tumors

While cell surface proteins, such as growth receptors overexpressed in certain tumors are excellent targets for drug candidates or tumor (e.g. cancer) treatment, the same proteins along with secreted proteins encoded by the genes amplified in tumor cells find additional use in the diagnosis and prognosis of tumors. For example, antibodies directed against the proteins products of genes amplified in tumor cells can be used as tumor diagnostics or prognostics.

For example, antibodies, including antibody fragments, can be used to qualitatively or quantitatively detect the expression of proteins encoded by the amplified genes ("marker gene products"). The antibody preferably is equipped with a detectable, e.g. fluorescent label, and binding can be monitored by light microscopy, flow cytometry, fluorimetry, or other techniques known in the art. These techniques are particularly suitable, if the amplified gene encodes a cell surface protein, e.g. a growth factor. Such binding assays are performed essentially as described herein.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker genie product in the tissue examined. It will be apparent for those skilled in the art that a wide variety of histological methods are readily available for in situ detection.

Example 10

Determination of LIV-1 in Tissue or Body Fluid

Described herein are serological methods for determining the presence of LIV-1 gene product (e.g. LIV-1-164647 protein or fragments thereof) in the body fluid of a mammal, preferably a human patient potentially suffering from the growth of cells overexpressing LIV-1. The method preferably detects the presence and, optionally, quantities, the amount of LIV-1 extracellular domain or fragments thereof in serum of such a patient, thereby providing a relatively non invasive method of detecting the overexpression of LIV-1 in a patient.

Essentially, the processes of this embodiment of the invention comprise incubating or otherwise exposing a sample of body fluid potentially containing LIV-1-164647 extracellular domain or fragments thereof, to anti-LIV-1-164647 monoclonal antibodies and detecting the presence of a reaction product. Those skilled in the art will recognize that there are many variations of these basic procedures. These include, for example, RIA, ELISA, precipitation, agglutination, complement fixation and immuno-fluorescence. In the currently preferred procedures, the monoclonal antibodies are appropriately labeled for detection. Labels useful in the practice of the invention include, but are not limited to, moieties, such as enzymes, that must be reacted or derivatized to be detected. The enzyme label can be detected by any of the currently utilized calorimetric, spectrophotometric, fluorospectrophotmetric or easometric techniques. The enzyme is combined with the antibody with bridging molecules such as carbodimiides, periodate, diisocyanates, glutaraldehyde and the like. Many enzymes which can be used in these procedures are known and can be utilized. Examples are peroxidase, alkaline phosphatase. $\beta$-glucuronidase. $\beta$-D-glucosidase, $\beta$-D-galactosidase, urease, glucose oxidase plus peroxidase, galactose oxidase plus peroxidase and acid phosphatase. Fluorescent materials which may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bid-diazotized benzadine and the like may be used to tag the antibodies with the above-described fluorescent, chemiluminescent, and enzyme labels. Various labeling techniques are described in Morrison, Methods in Enzymology 32b: 103 [1974]; Syvanen et al., J. Biol. Chem. 284:3762 [1973]; and Bolton and Hunter, Biochem J. 133:529 [1973]. Additionally, a radio-labelled antibody can be detected by any of the currently available counting procedures. Preferred isotope labels are $^{99}$Tc, $^{14}$C, $^{131}$I, $^{125}$I, $^{3}$H, $^{32}$P and $^{35}$S.

Additionally, the following non-limiting assay is useful for determining the presence of and to quantitate the amount of specific anti-LIV-1 monoclonal antibody (preferably specific to the extracellular domain of the LIV-1-164647 gene product, or a portion of the extracellular domain) in a body fluid of a mammal. The body fluid may include, but is not limited to serum, amniotic fluid, milk, umbilical cord serum, ocular aqueous and vitreous liquids, and ocular vitreous gel.

Plate Binding Activity Assay Using Humanized Anti-LIV-1 Monoclonal Antibody. The method of assaying anti-LIV-1 antibody described herein is meant as an example of such a method and is not meant to be limiting. A standardized preparation of anti-LIV-1 antibody, preferably specific to the extracellular domain of the LIV-1-167647 gene product, controls and serum samples are diluted with Assay Diluent (PBS/0.5% BSA/0.05% Polysorbate 20/0.01% Thimerosal). The dilutions of standardized anti-LIV-1 antibody are prepared to span a range of concentrations useful for a standard curve. The samples are diluted to fall within the standard curve.

An aliquot of Coat Antigen in Coating buffer (anti-LIV-1-164647 antibody in 0.05 M sodium carbonate buffer) is added to each well of a microtiter plate and incubated at 2-8° C. for 12-72 hours. The coatings solution is removed and each well is washed six times with water, then blotted to remove excess water. An aliquot of Assay Diluent is added to each well and incubated for 1-2 hours at ambient-temperature with agitation. The wells are washed as in the previous step. Aliquots of diluted standard, control and sample solutions are added to the wells and incubated at ambient temperature for 1 hour with agitation to allow binding of the antibody to the coating antigen. The wells are washed again with water as in previous steps.

Horse radish peroxidase-conjugate (HRP-conjugate, Goat anti-human IgG Fc conjugated to horseradish peroxidase, (Organon Teknika catalog #55253 or equivalent) is diluted with Assay Diluent to yield an appropriate optical density range between the highest and lowest standards. An aliquot of the HRP-conjugate solution is added to each well and incubated at ambient temperature for 1 hour with agitation. The wells are washed with water as in previous steps.

An aliquot of Substrate Solution (o-phenylenediamine (OPD) 5 mg tablet (Sigma P6912 or equivalent) in 12.5 ml 4 mM $H_2O_2$ in PBS) is added to each well and incubated for a sufficient period of time (approximately 8-10 minutes) in the dark at ambient temperature to allow color development. The reaction is stopped with an aliquot of 4.5 N sulfuric acid. Optical density is read at 490-492 nm for detection absorbance and 405 nm for reference absorbance. The standard curve data are plotted and the results for the controls and samples are determined from the standard curve.

Example 11

Methods of Treatment

It is contemplated that, according to the present invention, the anti-LIV-1 antibodies or other LIV-1 activity-blocking molecules may be used to treat various conditions characterized by overexpression and/or activation of the LIV-1 gene product with or without coexpression of ErbB2 above the ErbB2 expression found in healthy, nonmalignant cells, Exemplary conditions or disorders to be treated with such antibodies and other compounds, including, but not limited to, small organic and inorganic molecules, peptides, antisense molecules, etc. include benign or malignant tumors (e.g. breast, prostate, lung, and colon, as well as renal, liver, kidney, bladder, gastric, ovarian, colorectal, pancreatic, vulval, thyroid, hepatic carcinomas; sarcomas; glioblastomas, and various head and neck tumors); leukemias and lymphoid malignancies; other disorders such as neuronal, glial, astrocytal, hypothalamic and other glandular, macrophagal, epithelial, stromal and blastocoelic disorders, and inflammatory, angiogenic and immunologic disorders. Where an antibody is used to treat an LIV-1 overexpression related disorder, the antibody is preferably an anti-LIV-1-164647 antibody, more preferably a humanized antibody which binds to a polypeptide comprising an amino acid sequence from amino acid 114 to and including amino acid 135 of SEQ ID NO:4.

The anti-tumor agents of the present invention, e.g. antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-cancer agents, e.g. antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed. M. C. Perry, Williams & Wilkins, Baltimore, Md. (1992). The chemotherapeutic agent may precede, or follow administration of the anti-tumor agent, e.g. antibody, or may be given simultaneously therewith. The antibody may be combined with an anti-estrogen compound such as tamoxifen or an anti-progesterone such as onapristone (see, EP 616812) in dosages known for such molecules.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to the combined action (synergy) of the growth inhibitory agent and the antibody herein.

Where combined administration of a chemotherapeutic agent is desired, the combined administration includes co-administration in either order, wherein preferably there is a time period while both (or all) active agents simultaneously exert their biological activities. Preparation and dosing schedules for such chemotherapeutic agents may be used according to manufacturers instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith. The antibody may be combined with an anti-estrogen compound such as tamoxifen or an anti-progesterone such as onapristone (see, EP 616812) in dosages known for such molecules.

It may be desirable to also administer antibodies against other tumor associated antigens, such as antibodies which bind to vascular endothelial factor (VEGF). Alternatively, or in addition, two or more anti-LIV-1 antibodies may be co-administered to the patient. Sometimes, it may be beneficial to also administer one or more cytokines to the patient. The anti-LIV-1 antibody may be co-administered with a growth inhibitory agent. For example, the growth inhibitory agent may be administered first, followed by the anti-LIV-1 antibody, However, simultaneous administration or administration of the anti-LIV-1 antibody first is also contemplated. Suitable dosages for the growth inhibitory agent are those presently used and may be lowered due to the combined action (synergy) of the growth inhibitory agent and anti LIV-1 antibody.

In addition to the above therapeutic regimens, the patient may be subjected to surgical removal of cancer cells and/or radiation therapy.

For example, depending on the type and severity of the disease, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Example 12

Antibody Binding Studies

The results of the gene amplification study can be further verified by antibody binding studies, in which the ability of anti-LIV-1-164647 antibodies to detect the presence of or to inhibit the effect of the LIV-1 polypeptides on tumor (cancer) cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays, Zola, *Monoclonal Antibodies: A Manual of Techniques*, pp. 147-158 (CRC Press, Inc. 1987).

Competitive binding assays rely on the ability of a labeled standard to compete with the test sample analyte for binding with a limited amount of antibody. The amount of target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g. U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

Example 13

Cell-Based Tumor Assays

Cell-based assays and animal models for tumors (e.g. cancers) can be used to verify the findings of the gene amplification assay, and further understand the relationship between the genes identified herein and the development and pathogenesis of neoplastic cell growth. The role of gene products identified herein in the development and pathology of tumor or cancer can be tested by using primary tumor cells or cells lines that have been identified to amplify the genes herein. Such cells include, for example, the breast and prostate cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the neu protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumorogenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from tumors in transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642-648 [1985]).

Example 14

Animal Models

A variety of well known animal models can be used to further understand the role of the genes identified herein in the development and pathogenesis of tumors, and to test the efficacy of candidate therapeutic agents, including antibodies, and other antagonists of the native polypeptides, including small molecule antagonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sep. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H. C57BL, C57, CBA, DBA, DDD, I/st, NC, NFR, NFS, NFS/N, NZB, NZC, NZW, P, RIII and SJL. In addition, a wide variety of other animals with inherited immunological detects other than the nude mouse have been bred and used as recipients of tumor xenografts. For further details see, e.g. *The Nude Mouse in Oncology Research*, E. Boven and B. Winograd, eds., CRC Press, Inc. 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade 11 human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48, 689-696 [1983]). Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the neu oncogen was initially isolated), or neu-transformed NIH-3T3 cells into nude mice, essentially as described by Drebin et al. *PNAS USA* 83, 9129-9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54, 4726-4728 (1994) and Too et al., *Cancer Research* 55, 681-684 (1995). This model is based on the so-called "METAMOUSE™" sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A. CMS4, CMS5, CMS21, and WEHI-164 are chemically induced fibrosarcomas of BALB/c female mice (DeLeo et al., *J. Exp. Med.* 146, 720 [1977]), which provide a highly controllable model system for studying the anti-tumor activities of various agents (Palladino et al., *J. Immunol.* 138, 4023-4032 [1987]). Briefly, tumor cells are propagated in vitro in cell culture. Prior to injection into the animals, the cell lines are washed and suspended in buffer, at a cell density of about $1 \times 10^6$ to $10 \times 10^7$ cells/ml. The animals are then infected subcutaneously with 10 to 100 µl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41, suppl, 4, 309 [1980]), and evidence indicates that tumors can be started from injection of even a single cell and that a very high proportion of infected tumor cells survive. For further information about this tumor model see Zacharski, *Haemostasis* 16, 300-320 [1986]).

One way of evaluating the efficacy of a test compound on an implanted tumor in an animal model is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop of Immune-Deficient Animals*, Wu and Sheng eds., Basel. 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger. U.S. Pat. No. 4,873,191); retrovirus-mediated gene transfer into germ lines (e.g. Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cel., Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgenic into a particular cell type is also possible by following, for example, the technique of Lasko et al., *Proc. Natl. Acad. Sci. USA* 89, 6232-636(1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization. Northern blot analysis, PCR, or immunocytochemistry. The animals are further examined for signs of tumor or cancer development.

Alternatively "knock out" animals can be constructed high have a defective or altered gene encodings a LIV-1-164647 polypeptide identified herein, as a result of homologous recombination between the endogenous gene encoding the polypeptide and altered genomic DNA encoding the same polypeptide introduced into an embryonic cell of the animal. For example, cDNA encoding) a particular LIV-1 polypeptide can be used to clone genomic DNA encoding that polypeptide in accordance with established techniques. A portion of the genomic DNA encoding a particular LIV-1 polypeptide can be deleted or replaced with another gene, such as a (gene encoding a selectable marker which can be used to monitor integration. Typically, several kilobases of unaltered linking DNA (both at the 5' and 3' ends) are included in the vector [see e.g., Thomas and Capecchi, *Cell*, 51:503(1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, by their ability to defend against certain pathological conditions and by their development of pathological conditions due to absence of the LIV-1 polypeptide.

The efficacy of antibodies specifically binding the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography, Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another computed tomography scan. Computed tomography scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

Example 15

Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular LIV-1 polypeptide encoded by a nucleic acid sequence described herein, its interaction with that polypeptide can be assayed by methods well known for detecting protein-protein interactions. Such assays include traditional approaches, such as, cross-linking co-immunoprecipitation, and co-purification through gradients or chromatographic columns. In addition, protein-protein interactions can be monitored by using a yeast-based genetic system described by Fields and co-workers [Fields and Song, Nature (London) 340, 245-246 (1989); Chien et al., Proc. Natl Acad. Sci. USA 88, 9578-9582 (1991)] as disclosed by Chevray and Nathans [Proc. Natl. Acad. Sci. USA 89, 5789-5793 (1991)]. Many transcriptional activators, such as yeast GAL4, consist of two physically discrete modular domains, one acting as the DNA binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a LIV-1-encoding gene identified herein and other intra- or extracellular components can be tested as follows: usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra or extracellular component present in the mixture is monitored as described hereinabove. The formation of a complex in the control reaction(s) but not in the reaction mixture containing the test compound indicates that the test compound interferes with the interaction of the test compound and its reaction partner.

Example 16

Other Compositions and Methods for the Treatment of Tumors

The compositions useful in the treatment of tumors associated with the amplification of the genes identified herein include, without limitation, antibodies, small organic and inorganic molecules, peptides, phosphopeptides, antisense and ribozyme molecules, triple helix molecules, etc. that inhibit the expression and/or activity of the target gene product.

For example, antisense RNA and RNA molecule act to directly block the translation of mRNA by hybridizing to targeted mRNA and preventing protein translation. When antisense DNA is used, oligodeoxyribonucleotides derived from the translation initiation site, e.g. between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, Current Biology 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/33551, supra These molecules can be identified by any or any combination of the screening assays discussed hereinabove and/or by any other screening techniques well known for those skilled in the art.

Deposit of Material

The following material has been deposited with the American Type Culture Culture Collection, 10801 University Blvd., Manassas, Va. 20110-2209, USA (ATCC):

| Material | ATCC Dep No. | Deposit Date |
|---|---|---|
| Plasmid: | | |
| DNA164647 1803-1 | PTA-1534 | Mar. 21, 2000 |
| Hybridomas: | | |
| LIV-1.2945.2G1.1C7.2F10 | PTA-2961 | Jan. 23, 2001 |
| LIV-1.2982.4A12.1E8.1C4 | PTA-2962 | Jan. 23, 2001 |
| LIV-1.2983.3G9 1D4.1D7 | PTA-2963 | Jan. 23, 2001 |
| LIV-1.2984.6D6.1H10.2C1 | PTA-2964 | Jan. 23, 2001 |
| LIV-1.2985 4F3.2D6 1D7 | PTA-2960 | Jan. 23, 2001 |
| LIV-1.2987 1D8.1C11.2B7 | PTA-2959 | Jan. 23, 2001 |
| LIV-1.2988 1A7.1F2.1H7 | PTA-2965 | Jan. 23, 2001 |

This deposit was made under the provisions of the Budapest Treaty on the International Recognition of the Deposit of Microorganisms for the purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon influence of the pertinent U.S. patent or upon laying open to the public of any U.S. or foreign patent application, whichever comes first, and assures availability of the progeny to one determined by the U.S. Commissioner of Patents and Trade to be entitled thereto according to 35 U.S.C. § 122 and the Commissioner's rules pursuant thereto (including 37 CFR § 1.14 with particular reference to 886 OG 638)

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the right granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims. The disclosures of all citations in the specification are expressly incorporated herein by reference.

What is claimed is:

1. A method of diagnosing tumor in a mammal, comprising detecting and quantifying the level of expression of a nucleic acid sequence comprising a sequence 100% identical to the sequence from nucleotide 412 to and including nucleotide 477 of SEQ ID NO: 3 or to its fully complementary sequence in a test sample obtained from the mammal, and in a control sample, wherein a higher expression level in the test sample indicates the presence of tumor in the mammal from which the test sample was obtained.

2. The method of claim 1, wherein said test sample is obtained from an individual suspected to have neoplastic cell growth or proliferation.

3. The method of claim 2, wherein the sample is from breast tissue of the mammal.

* * * * *

SEQUENCE LISTING

<160> NUMBER OF SEQ ID NOS: 19

<210> SEQ ID NO 1
<211> LENGTH: 3461
<212> TYPE: DNA
<213> ORGANISM: Homo sapien

<400> SEQUENCE: 1

```
ctcgtgccga attcggcacg agaccgcgtg ttcgcgcctg gtagagattt          50
ctcgaagaca ccagtgggcc cgtgtggaac caaacctgcg cgcgtggccg         100
ggccgtggga caacgaggcc gcggagacga aggcgcaatg gcgaggaagt         150
tatctgtaat cttgatcctg acctttgccc tctctgtcac aaatcccctt         200
catgaactaa aagcagctgc tttcccccag accactgaga aaattagtcc         250
gaattgggaa tctggcatta atgttgactt ggcaatttcc acacggcaat         300
atcatctaca acagcttttc taccgctatg gagaaaataa ttctttgtca         350
gttgaagggt tcagaaaatt acttcaaaat ataggcatag ataagattaa         400
aagaatccat atacaccatg accacgacca tcactcagac cacgagcatc         450
actcagacca tgagcgtcac tcagaccatg agcatcactc agaccacgag         500
catcactctg accataatca tgctgcttct ggtaaaaata agcgaaaagc         550
tctttgccca gaccatgact cagatagttc aggtaaagat cctagaaaca         600 gccagggaa aggagctcac cgaccagaac atgccagtgg tagaaggaat         650
gtcaaggaca gtgttagtgc tagtgaagtg acctcaactg tgtacaacac         700
tgtctctgaa ggaactcact ttctagagac aatagagact ccaagacctg         750
gaaaactctt ccccaaagat gtaagcagct ccactccacc cagtgtcaca         800
tcaaagagcc gggtgagccg gctggctggt aggaaaacaa atgaatctgt         850
gagtgagccc cgaaaaggct ttatgtattc cagaaacaca aatgaaaatc         900
ctcaggagtg tttcaatgca tcaaagctac tgacatctca tggcatgggc         950
atccaggttc cgctgaatgc aacagagttc aactatctct gtccagccat        1000
catcaaccaa attgatgcta gatcttgtct gattcataca agtgaaaaga        1050
aggctgaaat ccctccaaag acctattcat tacaaatagc ctgggttggt        1100
ggttttatag ccatttccat catcagtttc ctgtctctgc tgggggttat        1150
cttagtgcct ctcatgaatc gggtgttttt caaatttctc ctgagtttcc        1200
ttgtggcact ggccgttggg actttgagtg gtgatgcttt tttacacctt        1250
```

| | |
|---|---|
| cttccacatt ctcatgcaag tcaccaccat agtcatagcc atgaagaacc | 1300 |
| agcaatggaa atgaaaagag gaccactttt cagtcatctg tcttctcaaa | 1350 |
| acatagaaga aagtgcctat tttgattcca cgtggaaggg tctaacagct | 1400 |
| ctaggaggcc tgtatttcat gtttcttgtt gaacatgtcc tcacattgat | 1450 |
| caaacaattt aaagataaga agaaaaagaa tcagaagaaa cctgaaaatg | 1500 |
| atgatgatgt ggagattaag aagcagttgt ccaagtatga atctcaactt | 1550 |
| tcaacaaatg aggagaaagt agatacagat gatcgaactg aaggctattt | 1600 |
| acgagcagac tcacaagagc cctcccactt tgattctcag cagcctgcag | 1650 |
| tcttggaaga agaagaggtc atgatagctc atgctcatcc acaggaagtc | 1700 |
| tacaatgaat atgtacccag agggtgcaag aataaatgcc attcacattt | 1750 |
| ccacgataca ctcggccagt cagacgatct cattcaccac catcatgact | 1800 |
| accatcatat tctccatcat caccaccacc aaaaccacca tcctcacagt | 1850 |
| cacagccagc gctactctcg ggaggagctg aaagatgccg gcgtcgccac | 1900 |
| tttggcctgg atggtgataa tgggtgatgg cctgcacaat ttcagcgatg | 1950 |
| gcctagcaat tggtgctgct tttactgaag gcttatcaag tggtttaagt | 2000 |
| acttctgttg ctgtgttctg tcatgagttg cctcatgaat taggtgactt | 2050 |
| tgctgttcta ctaaaggctg gcatgaccgt taagcaggct gtcctttata | 2100 |
| atgcattgtc agccatgctg gcgtatcttg gaatggcaac aggaattttc | 2150 |
| attggtcatt atgctgaaaa tgtttctatg tggatatttg cacttactgc | 2200 |
| tggcttattc atgtatgttg ctctggttga tatggtacct gaaatgctgc | 2250 |
| acaatgatgc tagtgaccat ggatgtagcc gctgggggta tttcttttta | 2300 |
| cagaatgctg ggatgctttt gggttttgga attatgttac ttattccata | 2350 |
| tttgaacata aaatcgtgtt cgtataaatt tctagttaag gtttaaatgc | 2400 |
| tagagtagct taaaagttg tcatagtttc agtaggtcat agggagatga | 2450 |
| gtttgtatgc tgtactatgc agcgtttaaa gttagtgggt tttgtgattt | 2500 |
| ttgtattgaa tattgctgtc tgttacaaag tcagttaaag gtacgtttta | 2550 |
| atatttaagt tattctatct tggagataaa atctgtatgt gcaattcacc | 2600 |
| ggtattacca gttttattatg taaacaagag atttggcatg acatgttctg | 2650 |
| tatgtttcag ggaaaaatgt ctttaatgct ttttcaagaa ctaacacagt | 2700 |
| tattcctata ctggattta ggtctctgaa gaactgctgg tgtttaggaa | 2750 |
| taagaatgtg catgaagcct aaaataccaa gaaagcttat actgaattta | 2800 |
| agcaaagaaa taaggagaa aagagaagaa tctgagaatt ggggaggcat | 2850 |
| agattcttat aaaaatcaca aaatttgttg taaattagag gggagaaatt | 2900 |
| tagaattaag tataaaaagg cagaattagt atagagtaca ttcattaaac | 2950 |
| attttttgtca ggattattc ccgtaaaaac gtagtgagca ctctcatata | 3000 |
| ctaattagtg tacatttaac tttgtataat acagaaatct aaatatattt | 3050 |
| aatgaattca agcaatatac acttgaccaa gaaattgaaa tttcaaaatg | 3100 |
| ttcgtgcggg ttatatacca gatgagtaca gtgagtagtt tatgtatcac | 3150 |
| cagactgggt tattgccaag ttatatatca ccaaaagctg tatgactgga | 3200 |
| tgttctggtt acctggttta caaaattatc agagtagtaa aactttgata | 3250 |

```
tatatgagga tattaaaact acactaagta tcatttgatt cgattcagaa         3300
agtactttga tatctctcag tgcttcagtg ctatcattgt gagcaattgt         3350
ctttatatac ggtactgtag ccatactagg cctgtctgtg gcattctcta         3400
gatgtttctt ttttacacaa taaattcctt atatcagctt gaaaaaaaaa         3450
aaaaaaaaaa a                                                   3461

<210> SEQ ID NO 2
<211> LENGTH: 752
<212> TYPE: PRT
<213> ORGANISM: Homo sapien

<400> SEQUENCE: 2

Met Ala Arg Lys Leu Ser Val Ile Leu Ile Leu Thr Phe Ala Leu
 1               5                  10                  15

Ser Val Thr Asn Pro Leu His Glu Leu Lys Ala Ala Phe Pro
                20                  25                  30

Gln Thr Thr Glu Lys Ile Ser Pro Asn Trp Glu Ser Gly Ile Asn
                35                  40                  45

Val Asp Leu Ala Ile Ser Thr Arg Gln Tyr His Leu Gln Gln Leu
                50                  55                  60

Phe Tyr Arg Tyr Gly Glu Asn Asn Ser Leu Ser Val Glu Gly Phe
 65                  70                                  75

Arg Lys Leu Leu Gln Asn Ile Gly Ile Asp Lys Ile Lys Arg Ile
                80                  85                  90

His Ile His His Asp His Asp His His Ser Asp His Glu His His
                95                 100                 105

Ser Asp His Glu Arg His Ser Asp His Glu His His Ser Asp His
                110                115                 120

Glu His His Ser Asp His Asn His Ala Ala Ser Gly Lys Asn Lys
                125                130                 135

Arg Lys Ala Leu Cys Pro Asp His Asp Ser Asp Ser Ser Gly Lys
                140                145                 150

Asp Pro Arg Asn Ser Gln Gly Lys Gly Ala His Arg Pro Glu His
                155                160                 165

Ala Ser Gly Arg Arg Asn Val Lys Asp Ser Val Ser Ala Ser Glu
                170                175                 180

Val Thr Ser Thr Val Tyr Asn Thr Val Ser Glu Gly Thr His Phe
                185                190                 195

Leu Glu Thr Ile Glu Thr Pro Arg Pro Gly Lys Leu Phe Pro Lys
                200                205                 210

Asp Val Ser Ser Ser Thr Pro Pro Ser Val Thr Ser Lys Ser Arg
                215                220                 225

Val Ser Arg Leu Ala Gly Arg Lys Thr Asn Glu Ser Val Ser Glu
                230                235                 240

Pro Arg Lys Gly Phe Met Tyr Ser Arg Asn Thr Asn Glu Asn Pro
                245                250                 255

Gln Glu Cys Phe Asn Ala Ser Lys Leu Leu Thr Ser His Gly Met
                260                265                 270

Gly Ile Gln Val Pro Leu Asn Ala Thr Glu Phe Asn Tyr Leu Cys
                275                280                 285

Pro Ala Ile Ile Asn Gln Ile Asp Ala Arg Ser Cys Leu Ile His
                290                295                 300
```

-continued

```
Thr Ser Glu Lys Lys Ala Glu Ile Pro Pro Lys Thr Tyr Ser Leu
            305                 310                 315

Gln Ile Ala Trp Val Gly Gly Phe Ile Ala Ile Ser Ile Ile Ser
            320                 325                 330

Phe Leu Ser Leu Leu Gly Val Ile Leu Val Pro Leu Met Asn Arg
            335                 340                 345

Val Phe Phe Lys Phe Leu Leu Ser Phe Leu Val Ala Leu Ala Val
            350                 355                 360

Gly Thr Leu Ser Gly Asp Ala Phe Leu His Leu Leu Pro His Ser
            365                 370                 375

His Ala Ser His His His Ser His Ser His Glu Glu Pro Ala Met
            380                 385                 390

Glu Met Lys Arg Gly Pro Leu Phe Ser His Leu Ser Ser Gln Asn
            395                 400                 405

Ile Glu Glu Ser Ala Tyr Phe Asp Ser Thr Trp Lys Gly Leu Thr
            410                 415                 420

Ala Leu Gly Gly Leu Tyr Phe Met Phe Leu Val Glu His Val Leu
            425                 430                 435

Thr Leu Ile Lys Gln Phe Lys Asp Lys Lys Lys Asn Gln Lys
            440                 445                 450

Lys Pro Glu Asn Asp Asp Val Glu Ile Lys Lys Gln Leu Ser
            455                 460                 465

Lys Tyr Glu Ser Gln Leu Ser Thr Asn Glu Glu Lys Val Asp Thr
            470                 475                 480

Asp Asp Arg Thr Glu Gly Tyr Leu Arg Ala Asp Ser Gln Glu Pro
            485                 490                 495

Ser His Phe Asp Ser Gln Gln Pro Ala Val Leu Glu Glu Glu
            500                 505                 510

Val Met Ile Ala His Ala His Pro Gln Glu Val Tyr Asn Glu Tyr
            515                 520                 525

Val Pro Arg Gly Cys Lys Asn Lys Cys His Ser His Phe His Asp
            530                 535                 540

Thr Leu Gly Gln Ser Asp Asp Leu Ile His His His Asp Tyr
            545                 550                 555

His His Ile Leu His His His His Gln Asn His His Pro His
            560                 565                 570

Ser His Ser Gln Arg Tyr Ser Arg Glu Glu Leu Lys Asp Ala Gly
            575                 580                 585

Val Ala Thr Leu Ala Trp Met Val Ile Met Gly Asp Gly Leu His
            590                 595                 600

Asn Phe Ser Asp Gly Leu Ala Ile Gly Ala Ala Phe Thr Glu Gly
            605                 610                 615

Leu Ser Ser Gly Leu Ser Thr Ser Val Ala Val Phe Cys His Glu
            620                 625                 630

Leu Pro His Glu Leu Gly Asp Phe Ala Val Leu Leu Lys Ala Gly
            635                 640                 645

Met Thr Val Lys Gln Ala Val Leu Tyr Asn Ala Leu Ser Ala Met
            650                 655                 660

Leu Ala Tyr Leu Gly Met Ala Thr Gly Ile Phe Ile Gly His Tyr
            665                 670                 675

Ala Glu Asn Val Ser Met Trp Ile Phe Ala Leu Thr Ala Gly Leu
            680                 685                 690

Phe Met Tyr Val Ala Leu Val Asp Met Val Pro Glu Met Leu His
```

| | | | |
|---|---|---|---|
| | 695 | 700 | 705 |

Asn Asp Ala Ser Asp His Gly Cys Ser Arg Trp Gly Tyr Phe Phe
710 715 720

Leu Gln Asn Ala Gly Met Leu Leu Gly Phe Gly Ile Met Leu Leu
725 730 735

Ile Pro Tyr Leu Asn Ile Lys Ser Cys Ser Tyr Lys Phe Leu Val
740 745 750

Lys Val

<210> SEQ ID NO 3
<211> LENGTH: 2776
<212> TYPE: DNA
<213> ORGANISM: Homo sapien

<400> SEQUENCE: 3

| | | | | | |
|---|---|---|---|---|---|
| ccggccgtgt | ggaaccaaac | ctgcgcgcgt | ggccgggccg | tgggacaacg | 50 |
| aggccgcgga | gacgaaggcg | caatggcgag | gaagttatct | gtaatcttga | 100 |
| tcctgacctt | tgccctctct | gtcacaaatc | cccttcatga | actaaaagca | 150 |
| gctgctttcc | cccagaccac | tgagaaaatt | agtccgaatt | gggaatctgg | 200 |
| cattaatgtt | gacttggcaa | tttccacacg | gcaatatcat | ctacaacagc | 250 |
| ttttctaccg | ctatggagaa | ataattctt | tgtcagttga | agggttcaga | 300 |
| aaattacttc | aaaatatagg | catagataag | attaaaagaa | tccatataca | 350 |
| ccatgaccac | gaccatcact | cagaccacga | gcatcactca | gaccatgagc | 400 |
| gtcactcaga | ccatgagcat | cactcagacc | acgagcatca | ctctgaccat | 450 |
| gatcatcact | cccaccataa | tcatgctgct | tctggtaaaa | ataagcgaaa | 500 |
| agctctttgc | ccagaccatg | actcagatag | ttcaggtaaa | gatcctagaa | 550 |
| acagccaggg | gaaaggagct | caccgaccag | aacatgccag | tggtagaagg | 600 |
| aatgtcaagg | acagtgttag | tgctagtgaa | gtgacctcaa | ctgtgtacaa | 650 |
| cactgtctct | gaaggaactc | actttctaga | gacaatagag | actccaagac | 700 |
| ctggaaaact | cttccccaaa | gatgtaagca | gctccactcc | acccagtgtc | 750 |
| acatcaaaga | gccgggtgag | ccggctggct | ggtaggaaaa | caaatgaatc | 800 |
| tgtgagtgag | ccccgaaaag | gctttatgta | ttccagaaac | acaaatgaaa | 850 |
| atcctcagga | gtgtttcaat | gcatcaaagc | tactgacatc | tcatggcatg | 900 |
| ggcatccagg | ttccgctgaa | tgcaacagag | ttcaactatc | tctgtccagc | 950 |
| catcatcaac | caaattgatg | ctagatcttg | tctgattcat | acaagtgaaa | 1000 |
| agaaggctga | aatccctcca | aagacctatt | cattacaaat | agcctgggtt | 1050 |
| ggtggtttta | tagccatttc | catcatcagt | ttcctgtctc | tgctgggggt | 1100 |
| tatcttagtg | cctctcatga | atcgggtgtt | tttcaaattt | ctcctgagtt | 1150 |
| tccttgtggc | actggccgtt | gggactttga | gtggtgatgc | ttttttacac | 1200 |
| cttcttccac | attctcatgc | aagtcaccac | catagtcata | gccatgaaga | 1250 |
| accagcaatg | gaaatgaaaa | gaggaccact | tttcagtcat | ctgtcttctc | 1300 |
| aaaacataga | agaaagtgcc | tattttgatt | ccacgtggaa | gggtctaaca | 1350 |
| gctctaggag | gcctgtattt | catgtttctt | gttgaacatg | tcctcacatt | 1400 |
| gatcaaacaa | tttaaagata | agaagaaaaa | gaatcagaag | aaacctgaaa | 1450 |

```
atgatgatga tgtggagatt aagaagcagt tgtccaagta tgaatctcaa        1500
ctttcaacaa atgaggagaa agtagataca gatgatcgaa ctgaaggcta        1550
tttacgagca gactcacaag agccctccca ctttgattct cagcagcctg        1600
cagtcttgga agaagaagag gtcatgatag ctcatgctca tccacaggaa        1650
gtctacaatg aatatgtacc cagagggtgc aagaataaat gccattcaca        1700
tttccacgat acactcggcc agtcagacga tctcattcac caccatcatg        1750
actaccatca tattctccat catcaccacc accaaaacca ccatcctcac        1800
agtcacagcc agcgctactc tcgggaggag ctgaaagatg ccggcgtcgc        1850
cactttggcc tggatggtga atgggtga tggcctgcac aatttcagcg          1900
atggcctagc aattggtgct gcttttactg aaggcttatc aagtggttta        1950
agtacttctg ttgctgtgtt ctgtcatgag ttgcctcatg aattaggtga        2000 cttttgctgtt ctactaaagg ctgacatgac cgttaagcag gctgtcctttt     2050 ataatgcatt gtcagccatg ctggcgtatc ttggaatggc aacaggaatt       2100
ttcattggtc attatgctga aaatgtttct atgtggatat ttgcacttac       2150
tgctggctta ttcatgtatg ttgctctggt tgatatggta cctgaaatgc       2200
tgcacaatga tgctagtgac catggatgta gccgctgggg gtatttcttt       2250
ttacagaatg ctgggatgct tttgggtttt ggaattatgt acttatttc        2300 catatttgaa cataaaatcg tgtttcgtat aaatttctag ttaaggttta       2350
aatgctagag tagcttaaaa agttgtcata gtttcagtag gtcataggga       2400
gatgagtttg tatgctgtac tatgcagcgt ttaaagttag tgggttttgt       2450 gattttgta ttgaatattg ctgtctgtta caaagtcagt taaaggtacg        2500
ttttaatatt taagttattc tatcttggag ataaaatctg tatgtgcaat       2550
tcaccggtat taccagttta ttatgtaaac aagagatttg gcatgacatg       2600
ttctgtatgt ttcagggaaa aatgtctttta atgctttttc aagaactaac     2650
acagttattc ctatactgga ttttaggtct ctgaagaact gctggtgttt      2700
aggaataaga atgtgcatga agcctaaaat accaagaaag cttatactga       2750
atttaagcaa aaaaaaaaaa aaaaaa                                 2776
```

<210> SEQ ID NO 4
<211> LENGTH: 755
<212> TYPE: PRT
<213> ORGANISM: Homo sapien

<400> SEQUENCE: 4

```
Met Ala Arg Lys Leu Ser Val Ile Leu Ile Leu Thr Phe Ala Leu
 1               5                  10                  15

Ser Val Thr Asn Pro Leu His Glu Leu Lys Ala Ala Phe Pro
                20                  25                  30

Gln Thr Thr Glu Lys Ile Ser Pro Asn Trp Glu Ser Gly Ile Asn
                35                  40                  45

Val Asp Leu Ala Ile Ser Thr Arg Gln Tyr His Leu Gln Gln Leu
                50                  55                  60

Phe Tyr Arg Tyr Gly Glu Asn Asn Ser Leu Ser Val Glu Gly Phe
                65                  70                  75

Arg Lys Leu Leu Gln Asn Ile Gly Ile Asp Lys Ile Lys Arg Ile
                80                  85                  90
```

-continued

```
His Ile His His Asp His Asp His His Ser Asp His Glu His His
             95                 100                 105
Ser Asp His Glu Arg His Ser Asp His Glu His His Ser Asp His
            110                 115                 120
Glu His His Ser Asp His Asp His His Ser His His Asn His Ala
            125                 130                 135
Ala Ser Gly Lys Asn Lys Arg Lys Ala Leu Cys Pro Asp His Asp
            140                 145                 150
Ser Asp Ser Ser Gly Lys Asp Pro Arg Asn Ser Gln Gly Lys Gly
            155                 160                 165
Ala His Arg Pro Glu His Ala Ser Gly Arg Arg Asn Val Lys Asp
            170                 175                 180
Ser Val Ser Ala Ser Glu Val Thr Ser Thr Val Tyr Asn Thr Val
            185                 190                 195
Ser Glu Gly Thr His Phe Leu Glu Thr Ile Glu Thr Pro Arg Pro
            200                 205                 210
Gly Lys Leu Phe Pro Lys Asp Val Ser Ser Thr Pro Pro Ser
            215                 220                 225
Val Thr Ser Lys Ser Arg Val Ser Arg Leu Ala Gly Arg Lys Thr
            230                 235                 240
Asn Glu Ser Val Ser Glu Pro Arg Lys Gly Phe Met Tyr Ser Arg
            245                 250                 255
Asn Thr Asn Glu Asn Pro Gln Glu Cys Phe Asn Ala Ser Lys Leu
            260                 265                 270
Leu Thr Ser His Gly Met Gly Ile Gln Val Pro Leu Asn Ala Thr
            275                 280                 285
Glu Phe Asn Tyr Leu Cys Pro Ala Ile Ile Asn Gln Ile Asp Ala
            290                 295                 300
Arg Ser Cys Leu Ile His Thr Ser Glu Lys Lys Ala Glu Ile Pro
            305                 310                 315
Pro Lys Thr Tyr Ser Leu Gln Ile Ala Trp Val Gly Gly Phe Ile
            320                 325                 330
Ala Ile Ser Ile Ile Ser Phe Leu Ser Leu Leu Gly Val Ile Leu
            335                 340                 345
Val Pro Leu Met Asn Arg Val Phe Phe Lys Phe Leu Leu Ser Phe
            350                 355                 360
Leu Val Ala Leu Ala Val Gly Thr Leu Ser Gly Asp Ala Phe Leu
            365                 370                 375
His Leu Leu Pro His Ser His Ala Ser His His Ser His Ser
            380                 385                 390
His Glu Glu Pro Ala Met Glu Met Lys Arg Gly Pro Leu Phe Ser
            395                 400                 405
His Leu Ser Ser Gln Asn Ile Glu Glu Ser Ala Tyr Phe Asp Ser
            410                 415                 420
Thr Trp Lys Gly Leu Thr Ala Leu Gly Gly Leu Tyr Phe Met Phe
            425                 430                 435
Leu Val Glu His Val Leu Thr Leu Ile Lys Gln Phe Lys Asp Lys
            440                 445                 450
Lys Lys Lys Asn Gln Lys Lys Pro Glu Asn Asp Asp Asp Val Glu
            455                 460                 465
Ile Lys Lys Gln Leu Ser Lys Tyr Glu Ser Gln Leu Ser Thr Asn
            470                 475                 480
```

-continued

```
Glu Glu Lys Val Asp Thr Asp Asp Arg Thr Glu Gly Tyr Leu Arg
            485                 490                 495

Ala Asp Ser Gln Glu Pro Ser His Phe Asp Ser Gln Gln Pro Ala
            500                 505                 510

Val Leu Glu Glu Glu Val Met Ile Ala His Ala His Pro Gln
        515                 520                 525

Glu Val Tyr Asn Glu Tyr Val Pro Arg Gly Cys Lys Asn Lys Cys
            530                 535                 540

His Ser His Phe His Asp Thr Leu Gly Gln Ser Asp Asp Leu Ile
            545                 550                 555

His His His His Asp Tyr His His Ile Leu His His His His His
            560                 565                 570

Gln Asn His His Pro His Ser His Ser Gln Arg Tyr Ser Arg Glu
            575                 580                 585

Glu Leu Lys Asp Ala Gly Val Ala Thr Leu Ala Trp Met Val Ile
            590                 595                 600

Met Gly Asp Gly Leu His Asn Phe Ser Asp Gly Leu Ala Ile Gly
            605                 610                 615

Ala Ala Phe Thr Glu Gly Leu Ser Ser Gly Leu Ser Thr Ser Val
            620                 625                 630

Ala Val Phe Cys His Glu Leu Pro His Glu Leu Gly Asp Phe Ala
            635                 640                 645

Val Leu Leu Lys Ala Asp Met Thr Val Lys Gln Ala Val Leu Tyr
            650                 655                 660

Asn Ala Leu Ser Ala Met Leu Ala Tyr Leu Gly Met Ala Thr Gly
            665                 670                 675

Ile Phe Ile Gly His Tyr Ala Glu Asn Val Ser Met Trp Ile Phe
            680                 685                 690

Ala Leu Thr Ala Gly Leu Phe Met Tyr Val Ala Leu Val Asp Met
            695                 700                 705

Val Pro Glu Met Leu His Asn Asp Ala Ser Asp His Gly Cys Ser
            710                 715                 720

Arg Trp Gly Tyr Phe Phe Leu Gln Asn Ala Gly Met Leu Leu Gly
            725                 730                 735

Phe Gly Ile Met Leu Leu Ile Ser Ile Phe Glu His Lys Ile Val
            740                 745                 750

Phe Arg Ile Asn Phe
            755
```

<210> SEQ ID NO 5
<211> LENGTH: 391
<212> TYPE: DNA
<213> ORGANISM: Artificial sequence
<220> FEATURE:
<223> OTHER INFORMATION: Probe
<220> FEATURE:
<221> NAME/KEY: Unknown
<222> LOCATION: 245, 308, 313, 352
<223> OTHER INFORMATION: Unknown nucleotide

<400> SEQUENCE: 5

```
tttttttttg atataaggaa tttattgtgt aaaaagaaa catctagaga          50 atgccacaga caggcctagt atggctacag taccgtatat aaaagacaat         100
tgctcacaat gatagcactg aagcactgag agatatcaaa gtactttctg         150
aatcgaatca aatgatactt agtgtagttt taatatcctc atatatatca         200
```

```
aagttttact actctgataa ttttgtaaac cagggtaacc aggancatcc          250
agtcatacag cttttgggtg atatataact tgggcaataa cccagtctgg          300
gtgatacnta aanctactca ctgtactcat ctgggtatat acccgcacgg          350
ancattttgg aaattcccaa tttcttgggt caggtgatat a                  391
```

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6

```
atgttgactt ggcaatttcc acacggca                                 28
```

<210> SEQ ID NO 7
<211> LENGTH: 27
<212> TYPE: DNA
<213> ORGANISM: Artificial sequence
<220> FEATURE:
<223> OTHER INFORMATION: Primer

<400> SEQUENCE: 7

```
taatgccaga ttcccaattc ggactaa                                  27
```

<210> SEQ ID NO 8
<211> LENGTH: 46
<212> TYPE: DNA
<213> ORGANISM: Artificial sequence
<220> FEATURE:
<223> OTHER INFORMATION: Probe

<400> SEQUENCE: 8

```
ttagttcatg aagggatttg tgacagaga gggcaaaggt caggat              46
```

<210> SEQ ID NO 9
<211> LENGTH: 42
<212> TYPE: DNA
<213> ORGANISM: Artificial sequence
<220> FEATURE:
<223> OTHER INFORMATION: Primer

<400> SEQUENCE: 9

```
caacatcaaa tgcatcaact tcatgaacta aaagcagctg ct                 42
```

<210> SEQ ID NO 10
<211> LENGTH: 43
<212> TYPE: DNA
<213> ORGANISM: Artificial sequence
<220> FEATURE:
<223> OTHER INFORMATION: Primer

<400> SEQUENCE: 10

```
gagctcgagc ggccgcttag gtctttggag ggatttcagc ctt                43
```

<210> SEQ ID NO 11
<211> LENGTH: 17
<212> TYPE: PRT
<213> ORGANISM: Artificial sequence
<220> FEATURE:
<223> OTHER INFORMATION: Leader sequence

<400> SEQUENCE: 11

Met Lys His Gln His Gln His Gln His Gln His Gln His Gln His Gln Met

His Gln

<210> SEQ ID NO 12
<211> LENGTH: 551
<212> TYPE: DNA
<213> ORGANISM: Artificial sequence
<220> FEATURE:
<223> OTHER INFORMATION: CDNA

<400> SEQUENCE: 12

```
tgccattcac atttccacga tacactcggc cagtcagacg atctcattca         50
ccaccatcat gactaccatc atattctcca tcatcaccac caccaaaacc        100
accatcctca cagtcacagc cagcgctact ctcgggagga gctgaaagat        150
gccggcgtcg ccactttggc ctggatggtg ataatgggtg atggcctgca        200
caatttcagc gatggcctag caattggtgc tgcttttact gaaggcttat        250
caagtggttt aagtacttct gttgctgtgt tctgtcatga gttgcctcat        300
gaattaggtg actttgctgt tctactaaag gctgacatga ccgttaagca        350
ggctgtcctt tataatgcat tgtcagccat gctggcgtat cttggaatgg        400
caacaggaat tttcattggt cattatgctg aaaatgtttc tatgtggata        450
tttgcactta ctgctggctt attcatgtat gttgctctgg ttgatatggt        500
acctgaaatg ctgcacaatg atgctagtga ccatggatgt agccgctggg        550
g                                                            551
```

<210> SEQ ID NO 13
<211> LENGTH: 48
<212> TYPE: DNA
<213> ORGANISM: Artificial sequence
<220> FEATURE:
<223> OTHER INFORMATION: Primer

<400> SEQUENCE: 13

```
ggattctaat acgactcact atagggctgc cattcacatt tccacgat         48
```

<210> SEQ ID NO 14
<211> LENGTH: 44
<212> TYPE: DNA
<213> ORGANISM: Artificial sequence
<220> FEATURE:
<223> OTHER INFORMATION: Primer

<400> SEQUENCE: 14

```
ctatgaaatt aaccctcact aaagggaccc cagcgcctac atcc             44
```

<210> SEQ ID NO 15
<211> LENGTH: 620
<212> TYPE: DNA
<213> ORGANISM: Artificial sequence
<220> FEATURE:
<223> OTHER INFORMATION: CDNA

<400> SEQUENCE: 15

```
tggtcgtggt cttgggggtg gtctttggga tcctcatcaa gcgacggcag         50
cagaagatcc ggaagtacac gatgcggaga ctgctgcagg aaacggagct        100
ggtggagccg ctgacaccta gcggagcgat gcccaaccag gcgcagatgc        150
ggatcctgaa agagacggag ctgaggaagg tgaaggtgct tggatctggc        200
```

-continued

```
gcttttggca cagtctacaa gggcatctgg atccctgatg gggagaatgt       250
gaaaattcca gtggccatca aagtgttgag ggaaaacaca tcccccaaag       300
ccaacaaaga aatcttagac gaagcatacg tgatggctgg tgtgggctcc       350
ccatatgtct cccgccttct gggcatctgc ctgacatcca cggtgcagct       400
ggtgacacag cttatgccct atggctgcct cttagaccat gtccgggaaa       450
accgcggacg cctgggctcc caggacctgc tgaactggtg tatgcagatt       500
gccaagggga tgagctacct ggaggatgtg cggctcgtac acagggactt       550
ggccgctcgg aacgtgctgg tcaagagtcc caaccatgtc aaaattacag       600
acttcgggct ggctcggctg                                         620
```

<210> SEQ ID NO 16
<211> LENGTH: 290
<212> TYPE: DNA
<213> ORGANISM: Artificial sequence
<220> FEATURE:
<223> OTHER INFORMATION: CDNA

<400> SEQUENCE: 16

```
gctgcctgac ggccaggtca tcaccattgg caatgagcgg ttccgctgcc        50
ctgaggcact cttccagcct tccttcctgg gcatggagtc ctgtggcatc       100
cacgaaacta ccttcaactc catcatgaag tgtgactgtg acatccgcaa       150
agacctgtac gccaacacag tgctgtctgg cggcaccacc atgtaccctg       200
gcattgccga caggatgcag aaggagatca ctgccctggc acccagcaca       250
atgaagatca agatcattgc tcctctgagc gcaagtactc                  290
```

<210> SEQ ID NO 17
<211> LENGTH: 7
<212> TYPE: PRT
<213> ORGANISM: Homo sapien

<400> SEQUENCE: 17

His Asp His His Ser His His
 1               5

<210> SEQ ID NO 18
<211> LENGTH: 13
<212> TYPE: PRT
<213> ORGANISM: Homo sapien

<400> SEQUENCE: 18

Ser Ile Phe Glu His Lys Ile Val Phe Arg Ile Asn Phe
 1               5                  10

<210> SEQ ID NO 19
<211> LENGTH: 22
<212> TYPE: PRT
<213> ORGANISM: Homo sapien

<400> SEQUENCE: 19

His Glu His His Ser Asp His Glu His His Ser Asp His Asp His
 1               5                  10                  15

His Ser His His Asn His Ala
                 20